(12) United States Patent
Maduskuie et al.

(10) Patent No.: US 6,620,823 B2
(45) Date of Patent: Sep. 16, 2003

(54) LACTAM METALLOPROTEASE INHIBITORS

(75) Inventors: Thomas P Maduskuie, Wilmington, DE (US); Jingwu Duan, Newark, DE (US); Stephen E Mercer, Greenville, DE (US)

(73) Assignee: Bristol-Myers Squibb Pharme Company, Princeton, NJ (US)

( * ) Notice: Subject to any disclaimer, the term of this patent is extended or adjusted under 35 U.S.C. 154(b) by 0 days.

(21) Appl. No.: 09/901,937

(22) Filed: Jul. 10, 2001

(65) Prior Publication Data

US 2002/0042398 A1 Apr. 11, 2002

Related U.S. Application Data

(60) Provisional application No. 60/217,477, filed on Jul. 11, 2000.

(51) Int. Cl.$^7$ ............... C07D 403/00; C07D 207/00; C07D 215/12; C07D 401/00; C07D 409/00
(52) U.S. Cl. ............ 514/314; 514/326; 514/422; 540/480; 546/176; 546/208; 548/517; 548/518; 548/527
(58) Field of Search ............... 546/176, 208; 548/517, 518, 527; 540/480; 514/314, 326, 422

(56) References Cited

U.S. PATENT DOCUMENTS

| | | | | |
|---|---|---|---|---|
| 3,813,387 A | * | 5/1974 | Pfirrmann et al. | 260/239.6 |
| 4,839,360 A | * | 6/1989 | Sato et al. | 514/252 |

FOREIGN PATENT DOCUMENTS

| | | |
|---|---|---|
| EP | 574758 A | 12/1993 |
| EP | 640594 A | 3/1995 |
| GB | 2268934 A | 1/1994 |
| JP | 50005379 A | 1/1975 |
| JP | 52156924 A | 12/1977 |
| WO | WO 9424140 A | 10/1994 |
| WO | WO 9509841 A | 4/1995 |
| WO | WO 9813340 A | 4/1998 |
| WO | WO 99/18074 * | 4/1999 |
| WO | WO 9918074 A | 4/1999 |
| WO | WO 9941246 A | 8/1999 |
| WO | WO 9965867 A | 12/1999 |

OTHER PUBLICATIONS

Shaffer, J. W. et al. "Substitution in the hydantoin ring. VII. N–3propinoic acid and its ethyl ester and N–3–(2–cyanoethyl) derivatives". J. Med. Chem. (1968), 11(3), 462–6, Chemical Abstract.

Zvilichovsky, G. et al. "Reaction of carbonyl compounds with 3,5–dihydroxy–4–phenylisoxazole. Novel type of non-catalyzed condensation and carbon–carbon bond formation". J. Org. Chem. (1973), 38(10), 1782–6, Chemical Abstract.

El–Kerdawy, M. M. et al. "Synthesis of certain hydrantoin derivatives as potential anticonvulsant agents". Egypt J. Chem. (1976), vol. Date 1974, 17(6), 845–52, Chemical Abstract.

Waser, Von P. G. et al. "Die entwicklung neuer antiepileptika. I: antikonvulsive wirkung von N–(p–sulfamoylphenyl-)–succinimid–Derivaten". Arzneimittel Forschung. Drug Research, 1977, vol. 27, 2 pp. 1942–1953, table 9.

Zvilichovsky, G. et al. "On the reaction of phenyldisic acids with α,β–unsaturated carbonyl compounds. Reversible non-catalyzed Michael addition and ring closure to derivatives of 2H, 7H–isoxazolo[3,2–b][1,3]oxazine". J. Heterocycl. Chem. (1980), 17(2) 299–304.

Maguire, J. H. et al. "Hypolipidemic activity of antiepileptic 5–phenylhydantoins in mice". Eur. J. Phamacol. (1985)m 117(1), 135–8, Chemical Abstract.

Shimizu, K. D. et al. "Synthesis, resolution and structure of axially chiral atropisomeric N–arylimides". Tetrahedron Letter, (2000), 41(29), 5431–5434.

Schiloegl, K. et al. "β–isocyanato fatty acid esters and of their reaction products–ureas, dihydrouracils, β–alanine peptides". Chemical Abstract.

Chia, C. "Acrylnitrile–(IV) synthesis of some β–(5,5,–disubstituted hydantoin)propionyl hydrazides and their acetone hydrazones". Chemical Abstract.

CAS Registry No.: 58256–33–0.
CAS Registry No. 332374–80–8.

* cited by examiner

*Primary Examiner*—Bruck Kifle
(74) *Attorney, Agent, or Firm*—David H. Vance; Jing S. Belfield

(57) ABSTRACT

The present application describes novel lactams and derivatives thereof of formula I:

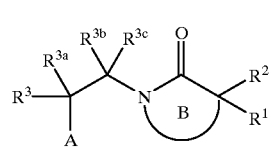

or pharmaceutically acceptable salt forms thereof, wherein ring B is a 4–8 membered cyclic amide comprising 0–3 additional heteroatoms selected from N, O, and S, which are useful as metalloprotease inhibitors.

18 Claims, No Drawings

LACTAM METALLOPROTEASE INHIBITORS

FIELD OF THE INVENTION

This invention relates generally to novel lactam metalloprotease inhibitors, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase has been identified that provides the specific cleavage product of proteoglycan, found in RA and OA patients (Lohmander L. S. et al. Arthritis Rheum. 36, 1993, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al, Lancet, 1994, 344, 1105), non-insulin dependent diabetes melitus. (Lohmander L. S. et al. Arthritis Rheum. 36, 1993, 1214–22) and Crohn's disease (Macdonald T. et al. Clin. Exp. Immunol. 81, 1990, 301).

Compounds which inhibit the production of TNF-α are therefore of therapeutic importance for the treatment of inflammatory disorders. Recently it has been shown that a matrix metalloproteinase or family of metalloproteinases, hereafter known as TNF-convertases (TNF-C), as well as other MP's are capable of cleaving TNF from its inactive to active form (Gearing et al Nature, 1994, 370, 555). This invention describes molecules that inhibit this conversion and hence the secretion of active TNF-α from cells. These novel molecules provide a means of mechanism based therapeutic intervention for diseases including but not restricted to septic shock, haemodynamic shock, sepsis syndrome, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteo and rheumatoid arthritis, multiple sclerosis, radiation damage, hyperoxic alveolar injury, periodontal disease, HIV and non-insulin dependent diabetes melitus.

Since excessive TNF production has been noted in several disease conditions also characterized by MP-mediated tissue degradation, compounds which inhibit both MPs and TNF production may also have a particular advantage in diseases where both mechanisms are involved.

There are several patents that disclose hydroxamate and carboxylate based MP inhibitors.

WO95/09841 describes compounds that are hydroxamic acid derivatives and are inhibitors of cytokine production.

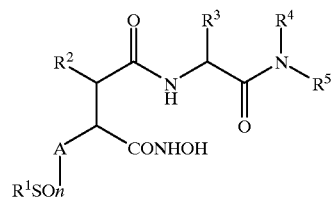

European Patent Application Publication No. 574,758 A1, discloses hydroxamic acid derivatives as collagenase inhibitors having the general formula:

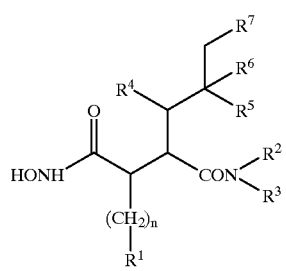

GB 2 268 934 A and WO 94/24140 claim hydroxamate inhibitors of MPs as inhibitors of TNF production.

The compounds of the current invention act as inhibitors of MPs, in particular aggrecanase and TNF. These novel molecules are provided as anti-inflammatory compounds and cartilage protecting therapeutics. The inhibition of aggrecanase, TNF-C, and other metalloproteinases by molecules of the present invention indicates they are anti-inflammatory and should prevent the degradation of cartilage by these enzymes, thereby alleviating the pathological conditions of osteo- and rheumatoid arthritis.

SUMMARY OF THE INVENTION

Accordingly, one object of the present invention is to provide novel lactams that are useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

It is another object of the present invention to provide novel lactams for use in therapy.

It is another object of the present invention to provide the use of novel lactams for the manufacture of a medicament for the treatment of an inflammatory disorder.

These and other objects, which will become apparent during the following detailed description, have been achieved by the inventors' discovery that compounds of formula I:

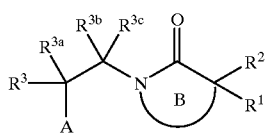

or pharmaceutically acceptable salt or prodrug forms thereof, wherein A, B, $R^1$, $R^2$, $R^3$, $R^{3a}$, $R^{3b}$, and $R^{3c}$ are defined below, are effective metalloprotease inhibitors.

DETAILED DESCRIPTION OF PREFERRED EMBODIMENTS

[1] Thus, in an embodiment, the present invention provides a novel compound of formula I:

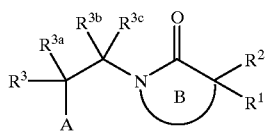

or a stereoisomer or pharmaceutically acceptable salt form thereof, wherein;

A is selected from $COR^5$, $-CO_2H$, $CH_2CO_2H$, $-CO_2R^6$, $-CONHOH$, $-CH_2CONHOH$, $-CONHOR^5$, $-CONHOR^6$, $-NHR^a$, $-N(OH)COR^5$, $-SH$, $-CH_2SH$, $-SO_2NHR^a$, $S(=NH)_2R^a$, $PO(OH)_2$, and $PO(OH)NHR^a$;

ring B is a 4–8 membered cyclic amide containing from 0–3 additional heteroatoms selected from O, $NR^a$, and $S(O)_p$, 0–1 additional carbonyl groups and 0–1 double bonds;

$R^1$ is $U-X-Y-Z-U^a13\ X^a-Y^a-Z^a$;

U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

X is absent or selected from $C_{1-10}$ alkylene, $C_{2-10}$ alkenylene, and $C_{2-10}$ alkynylene;

Y is absent or selected from O, $NR^a$, S(O)$_p$, and C(O);

Z is absent or selected from a $C_{3-13}$ carbocyclic residue substituted with 0–5 $R^b$ and a 5–14 membered heterocyclic system comprising carbon atoms and from 1–4 heteroatoms selected from the group consisting of N, O, and S and substituted with 0–5 $R^b$;

$U^a$ is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from $C_{1-10}$ alkylene, $C_{2-10}$ alkenylene, $C_{2-10}$ alkynylene;

$Y^a$ is absent or selected from O, $NR^a$, S(O)$_p$, and C(O);

$Z^a$ is selected from H, a $C_{3-13}$ carbocyclic residue substituted with 0–5 $R^c$ and a 5–14 membered heterocyclic system comprising carbon atoms and from 1–4 heteroatoms selected from the group consisting of N, O, and S and substituted with 0–5 $R^c$;

$R^2$ is selected from Q, $C_{1-10}$ alkylene-Q, $C_{2-10}$ alkenylene-Q, $C_{2-10}$ alkynylene-Q, (CRR')$_r$O(CRR')$_r$—Q, (CRR')$_r$NR$^a$(CRR')$_r$—Q, (CRR')$_r$NR$^a$C(O)(CRR')$_r$—Q, (CRR')$_r$C(O)NR$^a$(CRR')$_r$—Q, (CRR')$_r$C(O)(CRR')$_r$—Q, (CRR')$_r$C(O)O(CRR')$_r$—Q, (CRR')$_r$S(O)$_p$(CRR')$_r$—Q, (CRR')$_r$SO$_2$NR$^a$(CRR')$_r$—Q, (CRR')$_r$NR$^a$C(O)NR$^a$(CRR')$_r$—Q, (CRR')$_r$OC(O)NR$^a$(CRR')$_r$—Q, and (CRR')$_r$NR$^a$C(O)O(CRR')$_r$—Q;

R, at each occurrence, is independently selected from H, $CH_3$, $CH_2CH_3$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

alternatively, $R^1$ and $R^2$ combine to form a $C_{3-13}$ carbocyclic residue substituted with $R^{1'}$ and 0–3 $R^b$ or a 5–14 membered heterocyclic system comprising carbon atoms and from 1–4 heteroatoms selected from the group consisting of N, O, and S and substituted with $R^{1'}$ and 0–3 $R^b$;

Q is selected from H, a $C_{3-13}$ carbocyclic residue substituted with 0–5 $R^b$ and a 5–14 membered heterocyclic system comprising carbon atoms and from 1–4 heteroatoms selected from the group consisting of N, O, and S and substituted with 0–5 $R^b$;

$R^{1'}$ is $U^a-X^a-Y^a-Z^a$;

$R^3$ is selected from H, $C_{1-6}$ alkyl, and (3–10 membered carbocyclic or heterocyclic ring)(CRR')$_r$—, wherein the 3–10 membered carbocyclic or heterocyclic ring comprises carbon atoms and 0–3 ring heteroatoms selected from O, N, $NR^a$, and S(O)$_p$ and substituted with 0–2 $R^d$, provided that the cyclic moiety contains other than an N—S, O—S, O—O, or S—S bond;

$R^{3a}$ is selected from H, $C_{1-6}$ alkyl, phenyl, and benzyl;

$R^{3b}$ is selected from H, $C_{1-6}$ alkyl, and (3–10 membered carbocyclic or heterocyclic ring)(CRR')$_r$—, wherein the 3–10 membered carbocyclic or heterocyclic ring comprises carbon atoms and 0–3 ring heteroatoms selected from O, N, $NR^a$, and S(O)$_p$ and substituted with 0–2 $R^d$, provided that the cyclic moiety contains other than an N—S, O—S, O—O, or S—S bond;

$R^{3c}$ is selected from H, $C_{1-6}$ alkyl, phenyl, and benzyl;

alternatively one of $R^3$, $R^{3a}$, $R^{3b}$, and $R^{3c}$ maybe independently selected from (CRR')$_r$OR$^a$, (CRR')$_r$NR$^a$R$^{a'}$, $(CRR')_rC(O)R^a$, $(CRR')_rC(O)OR^a$, $(CRR')_rC(O)NR^aR^{a'}$, $(CRR')_rS(O)_pR^a$, and $(CRR')_rS(O)_pNR^aR^{a'}$, provided that in the group $(CRR')_rS(O)_pR^a$, $R^a$ is other than H;

alternatively, $R^3$ and $R^{3b}$ together with the carbon atoms to which they are attached combine to form a 3–10 membered carbocyclic or heterocyclic ring comprising carbon atoms and 0–3 ring heteroatoms selected from O, N, $NR^a$, and $S(O)_p$ and substituted with 0–2 $R^d$, provided that the cyclic moiety contains other than an N—S, O—S, O—O, or S—S bond;

alternatively, $R^3$ and $R^{3a}$ together with the carbon atom to which they are attached combine to form a 3–10 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

alternatively, $R^{3b}$ and $R^{3c}$ together with the carbon atom to which they are attached combine to form a 3–10 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

$R^a$, at each occurrence, is independently selected from H, $C_{1-4}$ alkyl, phenyl and benzyl;

$R^{a'}$, at each occurrence, is independently selected from H, $C_{1-4}$ alkyl, phenyl and benzyl;

$R^{a''}$, at each occurrence, is independently selected from H, $C_{1-4}$ alkyl, benzyl, $C_{3-7}$ carbocyclic group, or a 5–6 membered heteroaromatic ring containing 1–4 heteroatoms selected from the group consisting of N, O, and S;

alternatively, $R^a$ and $R^{a'}$ taken together with the nitrogen to which they are attached form a 5 or 6 membered ring comprising 0–1 additional heteroatoms selected from the group consisting of N, O, and S;

$R^b$, at each occurrence, is independently selected from $C_{1-6}$ alkyl, $OR^a$, Cl, F, Br, I, $=O$, CN, $NO_2$, $NR^aR^{a'}$, $C(O)R^{a''}$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, $=O$, CN, $NO_2$, $NR^aR^{a'}$, $C(O)R^a$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, —CH(=NOH), —C(=NOH)CH_3$, $(CRR')_sO(CRR')_sR^d$, $(CRR')_sS(O)_p(CRR')_sR^d$, $(CRR')_sNR^a(CRR')_sR^d$, phenyl, and a 5–14 membered heterocyclic group comprising 1–4 heteroatoms selected from the group consisting of N, O, and S;

$R^d$, at each occurrence, is independently selected from $C_{1-6}$ alkyl, $OR^a$, Cl, F, Br, I, $=O$, CN, $NO_2$, $NR^aR^{a'}$, $C(O)R^a$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, phenyl, and a 5–6 membered heterocyclic group comprising 1–4 heteroatoms selected from the group consisting of N, O, and S;

alternatively, when two $R^d$s are attached to adjacent atoms on $R^3$, $R^{3a}$, $R^{3b}$, or $R^{3c}$, they combine to form a 5–6 membered carbocyclic ring or a 5–6 membered heterocyclic ring comprising 1–4 heteroatoms selected from the group consisting of $NR^a$, O, and S;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is independently selected from phenyl substituted with 0–3 $R^b$, biphenyl substituted with 0–2 $R^b$, naphthyl substituted with 0–3 $R^b$ and a 5–10 membered heteroaryl system comprising 1–4 heteroatoms selected from the group consisting of N, O, and S and substituted with 0–3 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_{1-5}$ alkyl)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, —$CH(R^8)OC(=O)OR^9$, and

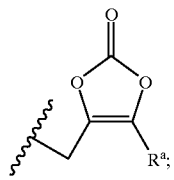

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^e$, $C_{3-8}$ cycloalkyl substituted with 1–2 $R^e$, and phenyl substituted with 0–2 $R^b$;

$R^e$, at each occurrence, is selected from $C_{1-4}$ alkyl, $C_{3-8}$ cycloalkyl, $C_{1-5}$ alkoxy, phenyl substituted with 0–2 $R^b$;

p, at each occurrence, is selected from 0, 1, and 2;

r, at each occurrence, is selected from 0, 1, 2, 3, 4, and 5;

r', at each occurrence, is selected from 0, 1, 2, 3, 4, and 5;

s, at each occurrence, is selected from 0, 1, 2, and 3; and, s', at each occurrence, is selected from 0, 1, 2, and 3.

[2] In a preferred embodiment, the present invention provides compounds, wherein:

A is selected from —$CO_2H$, $CH_2CO_2H$, —CONHOH, —$CONHOR^5$, —$CONHOR^6$, —$N(OH)COR^5$, —SH, and —$CH_2SH$;

ring B is a 4–6 membered cyclic amide containing from 0–3 additional heteroatoms selected from O, $NR^a$, and $S(O)_p$, 0–1 additional carbonyl groups and 0–1 double bonds;

$R^1$ is U—X—Y—Z—$U^a$—$X^a$—$Y^a$—$Z^a$;

U is absent or is selected from: O, $NR^a$, C(O), C(O)O, OC(O), $C(O)NR^a$, $NR^aC(O)$, $S(O)_p$, and $S(O)_pNR^a$;

X is absent or selected from $C_{1-6}$ alkylene, $C_{2-6}$ alkenylene, and $C_{2-6}$ alkynylene;

Y is absent or selected from O, $NR^a$, and C(O);

Z is absent or selected from a $C_{3-10}$ carbocyclic residue substituted with 0–5 $R^b$ and a 5–10 membered heterocyclic system comprising carbon atoms and from 1–4 heteroatoms selected from the group consisting of N, O, and S and substituted with 0–5 $R^b$;

$U^a$ is absent or is selected from: O, $NR^a$, C(O), C(O)O, OC(O), $C(O)NR^a$, $NR^aC(O)$, $S(O)_p$, and $S(O)_pNR^a$;

$X^a$ is absent or selected from $C_{1-6}$ alkylene, $C_{2-6}$ alkenylene, $C_{2-6}$ alkynylene;

$Y^a$ is absent or selected from O, $NR^a$, and C(O);

$Z^a$ is selected from H, a $C_{5-10}$ carbocyclic residue substituted with 0–5 $R^c$ and a 5–10 membered heterocyclic system comprising carbon atoms and from 1–4 heteroatoms selected from the group consisting of N, O, and S and substituted with 0–5 $R^c$;

$R^2$ is selected from Q, $C_{1-6}$ alkylene-Q, $C_{2-6}$ alkenylene-Q, $C_{2-6}$ alkynylene-Q, $(CRR')_rO(CRR')_r$—Q, $(CRR')_{r'}NR^a(CRR')_r$—Q, $(CRR')_rNR^aC(O)(CRR')_r$—Q, $(CRR')_rC(O)NR^a(CRR')_r$—Q, $(CRR')_rC(O)(CRR')_r$—Q, $(CRR')_{r'}C(O)O(CRR')_r$—Q, $(CRR')_rS(O)_p(CRR')_r$—Q, and $(CRR')_rSO_2NR^a(CRR')_r$—Q;

R, at each occurrence, is independently selected from H, $CH_3$, $CH_2CH_3$, and $CH=CH_2$;

R', at each occurrence, is independently selected from H, $CH_3$, and $CH_2CH_3$;

alternatively, $R^1$ and $R^2$ combine to form a $C_{3-10}$ carbocyclic residue substituted with $R^{1'}$ and 0–3 $R^b$ or a 5–10 membered heterocyclic system comprising carbon atoms and from 1–4 heteroatoms selected from the group consisting of N, O, and S and substituted with $R^{1'}$ and 0–3 $R^b$;

Q is selected from H, a $C_{5-10}$ carbocyclic residue substituted with 0–5 $R^b$ and a 5–10 membered heterocyclic system comprising carbon atoms and from 1–4 heteroatoms selected from the group consisting of N, O, and S and substituted with 0–5 $R^b$;

$R^{1'}$ is $U^a$—$X^a$—$Y^a$—$Z^a$;

$R^3$ is selected from H, $C_{1-6}$ alkyl, and (5–10 membered carbocyclic or heterocyclic ring)$(CRR')_r$—, wherein the 5–10 membered carbocyclic or heterocyclic ring comprises carbon atoms and 0–3 ring heteroatoms selected from O, N, $NR^a$, and $S(O)_p$ and substituted with 0–2 $R^d$, provided that the cyclic moiety contains other than an N—S, O—S, O—O, or S—S bond;

$R^{3a}$ is selected from H, $C_{1-6}$ alkyl, phenyl, and benzyl;

$R^{3b}$ is selected from H, $C_{1-6}$ alkyl, and (5–10 membered carbocyclic or heterocyclic ring) $(CRR')_r$—, wherein the 5–10 membered carbocyclic or heterocyclic ring comprises carbon atoms and 0–3 ring heteroatoms selected from O, N, $NR^a$, and $S(O)_p$ and substituted with 0–2 $R^d$, provided that the cyclic moiety contains other than an N—S, O—S, O—O, or S—S bond;

$R^{3c}$ is selected from H, $C_{1-6}$ alkyl, phenyl, and benzyl;

alternatively one of $R^3$, $R^{3a}$, $R^{3b}$, and $R^{3c}$ maybe independently selected from $(CRR')_rOR^a$, $(CRR')_rNR^aR^{a'}$, $(CRR')_rC(O)R^a$, $(CRR')_rC(O)OR^a$, $(CRR')_rC(O)NR^aR^{a'}$, $(CRR')_rS(O)_pR^a$, and $(CRR')_rS(O)_pNR^aR^{a'}$, provided that in the group $(CRR')_rS(O)_pR^a$, $R^a$ is other than H;

alternatively, $R^3$ and $R^{3b}$ together with the carbon atoms to which they are attached combine to form a 4–10 membered carbocyclic or heterocyclic ring comprising carbon atoms and 0–3 ring heteroatoms selected from O, N, $NR^a$, and $S(O)_p$ and substituted with 0–2 $R^d$, provided that the cyclic moiety contains other than an N—S, O—S, O—O, or S—S bond;

alternatively, $R^3$ and $R^{3a}$ together with the carbon atom to which they are attached combine to form a 4–10 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

alternatively, $R^{3b}$ and $R^{3c}$ together with the carbon atom to which they are attached combine to form a 4–10 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

$R^b$, at each occurrence, is independently selected from $C_{1-6}$ alkyl, $OR^a$, Cl, F, Br, I, =O, CN, $NO_2$, $NR^aR^{a'}$, $C(O)R^{a'}$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, —CH(=NOH), —C(=NOH)$CH_3$, $(CRR')_sO(CRR')_sR^d$, $(CRR')_sS(O)_p(CRR')_sR^d$, $(CRR')_sNR^a(CRR')_sR^d$, phenyl, and a 5–10 membered heterocyclic group comprising 1–4 heteroatoms selected from the group consisting of N, O, and S;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, phenyl, and a 5–6 membered heterocyclic group comprising 1–4 heteroatoms selected from the group consisting of N, O, and S;

alternatively, when two $R^d$s are attached to adjacent atoms on $R^3$, $R^{3a}$, $R^{3b}$, or $R^{3c}$, they combine to form a 5–6 membered carbocyclic ring or a 5–6 membered heterocyclic ring comprising 1–4 heteroatoms selected from the group consisting of $NR^a$, O, and S;

r, at each occurrence, is selected from 0, 1, 2, 3, and 4;

r', at each occurrence, is selected from 0, 1, 2, 3, and 4;

s, at each occurrence, is selected from 0, 1, and 2; and, s', at each occurrence, is selected from 0, 1, and 2.

[3] In another preferred embodiment, the present invention provides compounds, wherein:

A is selected from —$CO_2H$, $CH_2CO_2H$, —CONHOH, —CONHOR$^5$, and —N(OH)COR$^5$;

ring B is a 5–6 membered cyclic amide containing from 0–2 additional heteroatoms selected from O, $NR^a$, and $S(O)_p$, 0–1 additional carbonyl groups and 0–1 double bonds;

$R^1$ is U—X—Y—Z—$U^a$—$X^a$—$Y^a$—$Z^a$;

U is absent or is selected from: O, $NR^a$, C(O), C(O)$NR^a$, and $S(O)_p$;

X is absent or is $C_{1-4}$ alkylene;

Y is absent or selected from O and $NR^a$;

Z is absent or selected from a $C_{5-6}$ carbocyclic residue substituted with 0–3 $R^b$ and a 5–6 membered heterocyclic system comprising carbon atoms and from 1–4 heteroatoms selected from the group consisting of N, O, and S and substituted with 0–3 $R^b$;

$U^a$ is absent or is selected from: O, $NR^a$, C(O), C(O)$NR^a$, and $S(O)_p$;

$X^a$ is absent or selected from $C_{1-6}$ alkylene and $C_{2-6}$ alkenylene;

$Y^a$ is absent or selected from O and $NR^a$;

$Z^a$ is selected from H, a $C_{5-10}$ carbocyclic residue substituted with 0–3 $R^c$ and a 5–10 membered heterocyclic system comprising carbon atoms and from 1–4 heteroatoms selected from the group consisting of N, O, and S and substituted with 0–3 $R^c$;

$R^2$ is selected from Q, $C_{1-6}$ alkylene-Q, $C_{2-6}$ alkenylene-Q, $(CRR')_r O(CRR')_{r'}$—Q, $(CRR')_r NR^a(CRR')_{r'}$—Q, and $(CRR')_r C(O)(CRR')_{r'}$—Q;

R, at each occurrence, is independently selected from H, $CH_3$, and $CH_2CH_3$;

R', at each occurrence, is independently selected from H and $CH_3$;

alternatively, $R^1$ and $R^2$ combine to form a $C_{5-6}$ carbocyclic residue substituted with $R^{1'}$ and 0–3 $R^b$ or a 5–6 membered heterocyclic system comprising carbon atoms and from 1–4 heteroatoms selected from the group consisting of N, O, and S and substituted with $R^{1'}$ and 0–3 $R^b$;

Q is selected from H, a $C_{5-6}$ carbocyclic residue substituted with 0–5 $R^b$ and a 5–6 membered heterocyclic system comprising carbon atoms and from 1–4 heteroatoms selected from the group consisting of N, O, and S and substituted with 0–5 $R^b$;

$R^{1'}$ is $U^a$—$X^a$—$Y^a$—$Z^a$;

$R^3$ is selected from H, $C_{1-6}$ alkyl, and (5–6 membered carbocyclic or heterocyclic ring)$(CH_2)_r$—, wherein the 5–6 membered carbocyclic or heterocyclic ring comprises carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

$R^{3a}$ is selected from H, $C_{1-6}$ alkyl, phenyl, and benzyl;

$R_{3b}$ is selected from H, $C_{1-6}$ alkyl, and (5–6 membered carbocyclic or heterocyclic ring)$(CH_2)_r$—, wherein the 5–6 membered carbocyclic or heterocyclic ring comprises carbon atoms and 0–2 ring heteroatoms selected from O, N, $NR^a$, and $S(O)_p$ and substituted with 0–2 $R^d$, provided that the cyclic moiety contains other than an, N—S, O—S, O—O, or S—S bond;

$R^{3c}$ is selected from H, $C_{1-6}$ alkyl, phenyl, and benzyl;

alternatively one of $R^3$, $R^{3a}$, $R^{3b}$, and $R^{3c}$ is independently selected from $(CRR')_r OR^a$, $(CRR')_r NR^a R^{a'}$, $(CRR')_r C(O)R^a$, $(CRR')_r C(O)OR^a$, $(CRR')_r C(O)NR^a R^{a'}$, $(CRR')_{r'} S(O)_p R^a$, and $(CRR')_r S(O)_p NR^a R^{a'}$, provided that in the group $(CRR')_r S(O)_p R^a$, $R^a$ is other than H;

alternatively, $R^3$ and $R^{3b}$ together with the carbon atoms to which they are attached combine to form a 4–8 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

alternatively, $R^3$ and $R^{3a}$ together with the carbon atom to which they are attached combine to form a 5–8 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

alternatively, $R^{3b}$ and $R^{3c}$ together with the carbon atom to which they are attached combine to form a 5–8 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

$R^c$, at each occurrence, is independently selected from $C_{1-6}$ alkyl, $OR^a$, Cl, F, Br, I, =O, CN, $NO_2$, $NR^a R^{a'}$, $C(O)R^a$, $C(O)OR^a$, $C(O)NR^a R^{a'}$, $NR^a C(O)NR^a R^{a'}$, $S(O)_2 NR^a R^{a'}$, $S(O)_p R^a$, $CF_3$, $CF_2 CF_3$, —CH(=NOH), —C(=NOH)$CH_3$, and phenyl;

r, at each occurrence, is selected from 0, 1, 2, and 3; and, r', at each occurrence, is selected from 0, 1, 2, and 3.

[4] In another preferred embodiment, the present invention provides compounds, wherein:

A is selected from —$CO_2H$, $CH_2CO_2H$, —CONHOH, —$CONHOR^5$, and —N(OH)$COR^5$;

ring B is a 5 membered cyclic amide containing from 0–1 additional heteroatoms selected from O, $NR^a$, and $S(O)_p$, 0–1 additional carbonyl groups and 0–1 double bonds;

$R^1$ is U—X—Y—Z—$U^a$—$X^a$—$Y^a$—$Z^a$;

U is absent;

X is absent;

Y is absent;

Z is absent or selected from phenyl substituted with 0–2 $R^b$ and a 5–6 membered heteroaryl comprising carbon atoms and from 1–4 heteroatoms selected from the group consisting of N, O, and S and substituted with 0–3 $R^b$;

$U^a$ is absent or is O;

$X^a$ is absent or selected from $C_{1-4}$ alkylene and $C_{2-4}$ alkenylene;

$Y^a$ is absent or is O;

$Z^a$ is selected from H, a $C_{6-10}$ aryl residue substituted with 0–3 $R^c$ and a 5–10 membered heteroaryl comprising carbon atoms and from 1–4 heteroatoms selected from the group consisting of N, O, and S and substituted with 0–3 $R^c$;

$R^2$ is selected from $C_{1-6}$ alkylene, $(CRR')_r OH$, and $(CRR')_r NR^a H$;

$R^3$ is selected from H, $C_{1-6}$ alkyl, and (5–6 membered carbocyclic or heterocyclic ring)$(CH_2)_r$—, wherein the 5–6 membered carbocyclic or heterocyclic ring comprises carbon atoms and 0–1 ring heteroatoms selected from O, N, $NR^a$, and $S(O)_p$ and substituted with 0–2 $R^d$;

$R^{3a}$ is selected from H, $C_{1-6}$ alkyl, phenyl, and benzyl;

$R^{3b}$ is selected from H, $C_{1-6}$ alkyl, and (5–6 membered carbocyclic or heterocyclic ring)$(CH_2)_r$— wherein the 5–6 membered carbocyclic or heterocyclic ring comprises carbon atoms and 0–1 ring heteroatoms selected from O, N, $NR^a$, and $S(O)_p$ and substituted with 0–2 $R^d$;

$R^{3c}$ is selected from H, $C_{1-6}$ alkyl, phenyl, and benzyl;

alternatively, $R^3$ and $R^{3b}$ together with the carbon atoms to which they are attached combine to form a 4, 5, 6, 7 or 8 membered carbocyclic or heterocyclic ring comprising carbon atoms and 0–1 ring heteroatoms selected from O, N, $NR^a$, and $S(O)_p$ and substituted with 0–2 $R^d$;

alternatively, $R^3$ and $R^{3a}$ together with the carbon atom to which they are attached combine to form a 5–6 membered carbocyclic or heterocyclic ring comprising carbon atoms and 0–1 ring heteroatoms selected from O, N, $NR^a$, and $S(O)_p$ and substituted with 0–2 $R^d$;

alternatively, $R^{3b}$ and $R^{3c}$ together with the carbon atom to which they are attached combine to form a 5–6 membered carbocyclic or heterocyclic ring comprising carbon atoms and 0–1 ring heteroatoms selected from O, N, $NR^a$, and $S(O)_p$ and substituted with 0–2 $R^d$;

R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, and phenyl;

r, at each occurrence, is selected from 0, 1, and 2; and, r', at each occurrence, is selected from 0, 1, and 2.

[5] In another preferred embodiment, the present invention provides compounds, wherein:

(1S-cis)-2-[3-amino-3-[4-[2-methyl-4-quinolinyl) methoxy]phenyl]-2-oxo-1-pyrrolidinyl]-N-hydroxycyclohexanecarboxamide bis(trifluoroacetate) (salt);

(1R-trans)-2-[3-amino-3-[4-[(2-methyl-4-quinolinyl) methoxy]phenyl]-2-oxo-1-pyrrolidinyl]-N-hydroxycyclohexanecarboxamide bis(trifluoroacetate) (salt);

(1R-trans)-2-[3-amino-3-[4-[(2-methyl-4-quinolinyl) methoxy]phenyl]-2-oxo-1-pyrrolidinyl] cyclohexanecarboxylic acid bis(trifluoroacetate) (salt);

(1S-cis)-2-[(3S)-3-amino-3-[4-[(2-methyl-4-quinolinyl) methoxy]phenyl]-2-oxo-1-pyrrolidinyl] cyclopentanecarboxylic acid bis(trifluoroacetate) (salt);

(1S-cis)-2-[(3S)-3-amino-3-[4-[(2-methyl-4-quinolinyl) methoxy]phenyl]-2-oxo-1-pyrrolidinyl]-N-hydroxycyclopentanecarboxamide bis(trifluoroacetate) (salt);

(1R-trans)-2-[(3S)-3-amino-3-[4-[(2-methyl-4-quinolinyl) methoxy]phenyl]-2-oxo-1-pyrrolidinyl]-N-hydroxycyclopentanecarboxamide bis(trifluoroacetate) (salt);

(1S-cis)-2-[(3S)-3-amino-3-[4-[(2-methyl-4-quinolinyl) methoxy]phenyl]-2-oxo-1-pyrrolidinyl]-N-hydroxy-4,4-dimethylcyclopentanecarboxamide bis(trifluoroacetate) (salt);

(1S-cis)-1-[(3S)-3-amino-3-[4-[(2-methyl-4-quinolinyl) methoxy]phenyl]-2-oxo-1-pyrrolidinyl]-2,3-dihydro-N-hydroxy-1H-indene-2-carboxamide bis(trifluoroacetate) (salt);

(3R-trans)-4-[(3S)-3-amino-3-[4-[(2-methyl-4-quinolinyl) methoxy]phenyl]-2-oxo-1-pyrrolidinyl]tetrahydro-N-hydroxy-3-furancarboxamide bis(trifluoroacetate) (salt);

(βR)-3-amino-N-hydroxy-β-(2-methylpropyl)-3-[4-[(2-methyl-4-quinolinyl) methoxy]phenyl]-2-oxo-1-pyrrolidinepropanamide bis(trifluoroacetate) (salt);

(βR)-3-amino-β-(2-methylpropyl)-3-[4-[(2-methyl-4-quinolinyl) methoxy]phenyl]-2-oxo-1-pyrrolidinepropanoic acid bis(trifluoroacetate) (salt); and, 3-amino-N-hydroxy-α,α-dimethyl-3-[4-[(2-methyl-4-quinolinyl) methoxy]phenyl]-2-oxo-1-pyrrolidinepropanamide bis(trifluoroacetate) (salt);

or a pharmaceutically acceptable salt form thereof.

In another embodiment, the present invention provides a novel pharmaceutical composition, comprising: a pharmaceutically acceptable carrier and a therapeutically effective amount of a compound of formula I or a pharmaceutically acceptable salt form thereof.

In another embodiment, the present invention provides a novel method for treating an inflammatory disorder, comprising: administering to a patient in need thereof a therapeutically effective amount of a compound of formula I or a pharmaceutically acceptable salt form thereof.

In another embodiment, the present invention provides a novel method of treating a condition or disease mediated by MPs, TNF, aggrecanase, or a combination thereof in a mammal, comprising: administering to the mammal in need of such treatment a therapeutically effective amount of a compound of formula I or a pharmaceutically acceptable salt form thereof.

In another embodiment, the present invention provides a novel method of treating a condition or disease wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel lactams for use in therapy.

In another embodiment, the present invention provides the use of novel lactams for the manufacture of a medicament for the treatment of an inflammatory disorder.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbonyl group or double bond be part (i.e., within) of the ring.

When any variable (e.g., R$^b$) occurs more than one time in any constituent or formula for a compound, its definition at each occurrence is independent of its definition at every other occurrence. Thus, for example, if a group is shown to be substituted with 0–2 R$^6$, then said group may optionally be substituted with up to two R$^6$ groups and R$^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic group" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that the heterocycle contains other than an N—O, N—S, O—S, O—O, or S—S bond. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benztriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

A series of γ-lactams of formula 10 are prepared by the methods outlined in Schemes 1 and 2. $R^1$-substituted methyl acetate 1 is deprotonated to form the enolate using bases such as sodium bis(trimethylsilyl)amide, lithium N,N-diisopropylamide, and sodium hydride. Alkylation with $R^2$—X provides 2. Further alkylation with allyl bromide under similar basic conditions gives ester 3. The olefin in 3 is then cleaved by ozonolysis or by dihydroxylation ($OsO_4$/NMO) followed by diol cleavage ($NaIO4$) to give aldehyde 4. Treatment of the aldehyde 4 and the appropriately substituted β-amino acid 5 with zinc in acetic acid at elevated temperature leads to reductive amination and lactamization to give γ-lactam 7. The γ-lactamization gives a mixture of two diastereomers epimeric at the quaternary center. The diastereomers of 7 are either separated or taken to the next step as a mixture.

Alternatively, aldehyde 4 is converted to lactam 7 through a stepwise sequence. Condensation of 4 with the β-amino ester 5 through reductive amination provides secondary amine 6. The reductive amination can be affected with reagents such as sodium borohydride, sodium cyanoborohydride, and sodium triacetoxyborohydride. Amine 6 is converted to 7 via thermally induced lactamization or methyl ester hydrolysis followed by amide bond formation using reagents such as BOP.

Lactam 7 can also be prepared from ester 3 through the carboxylic acid 8. Acid 8 and β-amino ester 5 can be coupled using standard peptide coupling reagents well known in the literature such as DCC, BOP, and TBTU (Bodanszky, M. in Peptide Chemistry A Practical Textbook, 2nd ed. Springer-Verlag, New York, 1993). Olefin degradation ($O_3$/$PPh_3$, or $OsO_4$/$NaIO_4$) and deoxygenation ($Et_3SiH$/$CF_3COOH$) gives lactam 7.

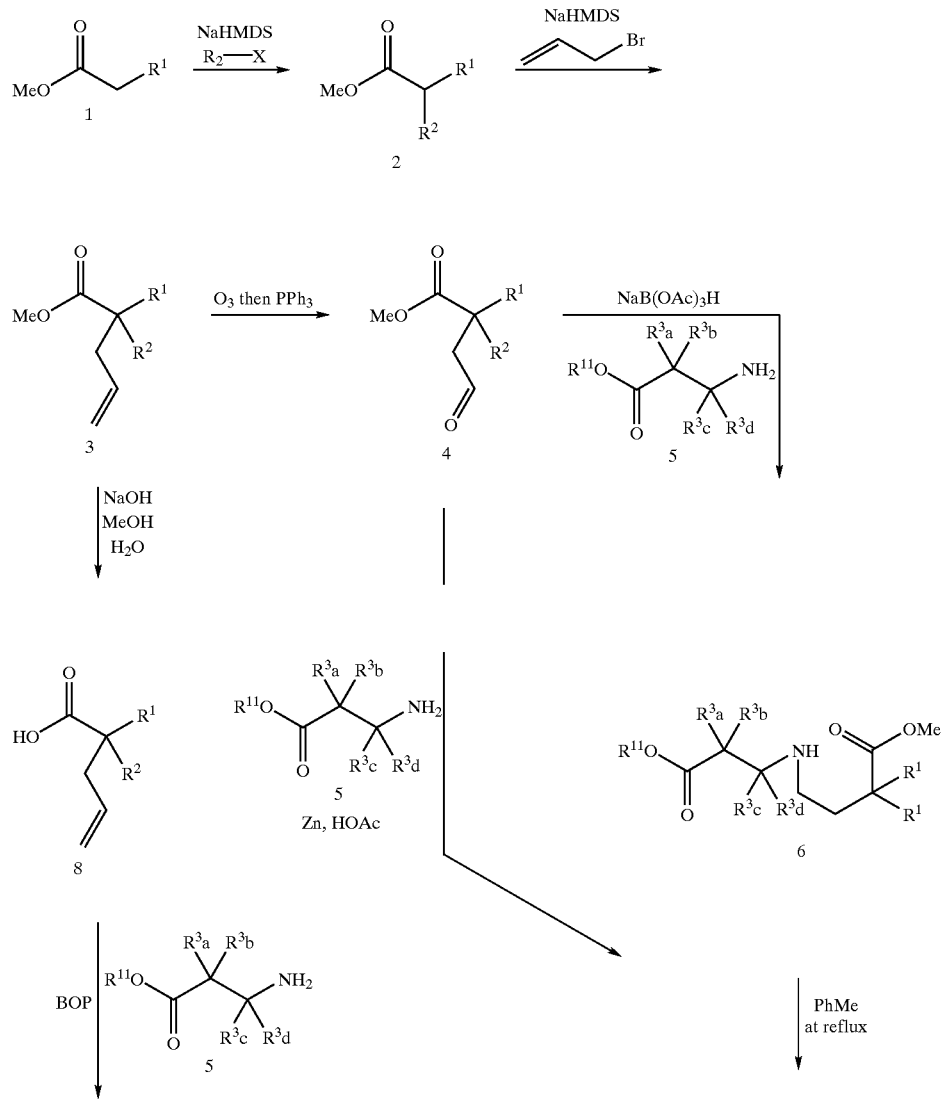

Scheme 1

-continued

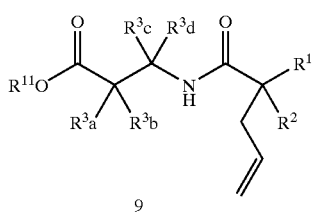

1) O₃ then PPh₃
2) Et₃SiH, CF₃COOH

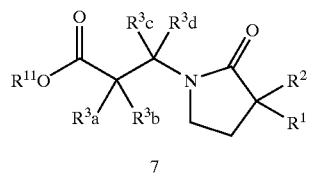

Many of the β-amino acid derivatives 5 are commercially available or are prepared from the commercial material by simple protecting group manipulations. Alternatively the β-amino acids can be prepared by a variety of methods discussed in "Entioselective Synthesis of β-Amino Acids" editied by Eusebio Juraisti, Wiley-VCH publisher. Others are synthesized by methods outlined in Scheme Ia. The cyano acetate compound 301 may be reacted with reagents such as LDA to generate the enolate which may be alkylated with an electrophile such as an alkyl halide or tosylate to give intermediate 302. The nitrile can be reduced with reagents such as LAH or Raney nickel or hygrogenation over PtO2 to give the β-amino acid 303.

Alternatively the β-amino acid like compound 307 can be prepared starting with a protected ester like Evans oxazolidinone. Generating the enolate with bases like LDA and reacting this with a bromoacetate to give compounds like 305. Hydrolysis of the oxazolidinone will give the carboxylic acid 306 and this can be transformed into the amine by a Curtius like reaction.

β-amino acids can also be prepared from the starting ketoester compound 308, reacting this with an amine like benzyl anime to prepare the enamine 309. The enamine can be reduced by a number of methods like hygrogenation over Pd/C or stepwise with sodium triacetoxyborohydride to give the saturated intermediate and then hydrogenation with Pd/C to prepare compounds like 310. Alternatively, the β-amino acid 310 can be prepared by reacting the α–β unsaturated ester in a Michael like fashion with an amine like benzyl amine or azide to give the amine compound 312. The compound 312 can be reduced by hydrogenation conditions well known in the literature to give compound 310.

These reactions can be carried out in such a way as to prepare enantiospecfic β-amino acids (G. Bartoli, C. Cimarelli, E. Marcantoni, G. Palmieri, M. Petrini, *J. Org. Chem.* 1994, 59, 5328–5335 and C. Cimerilli, G. Palmieri, *J. Org. Chem.* 1996, 61, 5557–5563.) or the isomers may be separated by chiral column HPLC.

Scheme Ia

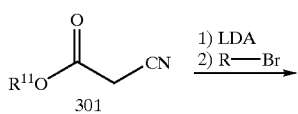

-continued

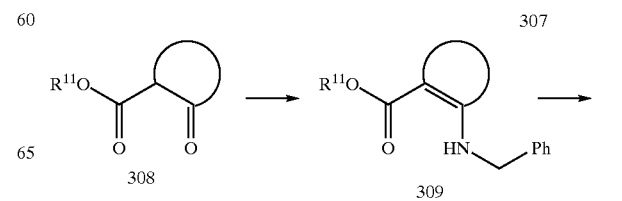

-continued

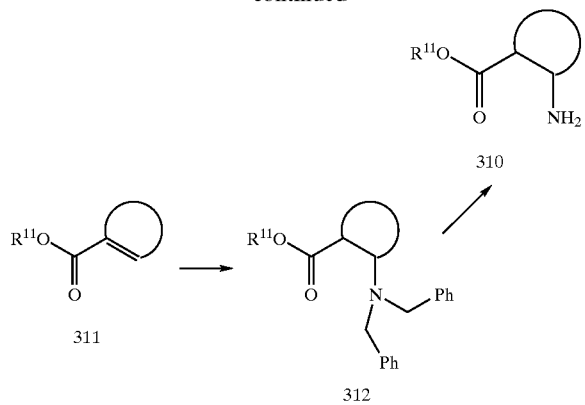

The methyl ester of 7 ($R^{11}$=Me) is converted to hydroxamic acid 10 by treatment with hydroxylamine under basic conditions (KOH or NaOMe) in methanol (Scheme 2) The methyl ester 7 ($R^{11}$=Me) can also be converted to benzyl protected hydroxamic acid with O-benzylhydroxylamine using Weinreb's trimethylalluminum conditions (Levin, J. I.; Turos, E.; Weinreb, S. M. *Syn. Commun.* 1982, 12, 989) or Roskamp's bis[bis(trimethylsilyl)amido]tin reagent (Wang, W. -B.; Roskamp, E. J. *J. Org. Chem.* 1992, 57, 6101). Hydrogenolysis then provides the hydroxamic acid 10. Alternatively, 10 can be prepared through the carboxylic intermediate 11. Carboxylic acid 11 is converted to 10 via coupling with hydroxylamine or NH2OBn followed by deprotection.

A variety of ethers of 4-hydroxyphenyllactam 13 are prepared using intermediate 7 when $R^1$ is benzyloxyphenyl group (Scheme 3). Removal of benzyl protecting group followed by alkylation with $R^4$—X produces 13. The alkylation can be affected with bases such as $K_2CO_3$, $Cs_2CO_3$, NaH, and t-BuOK. Alternatively compounds like 13 can also be prepared with $R^4$OH under Mitsunobu conditions.

$R^4$ can be appended to the aromatic ring of compound 12 by converting the phenol to the aryl triflate with methods like triflic anhydride and DIEA in an appropriate solvent. The aryl triflate is reacted with an organometallic under Stille or Suzuki conditions in the presence of palladium(0) catalyst to give compound 200. Alternatively, compound 12 reacts with lower or higher-order cuprates to give compound 200 as well.

Compounds like 201 can be prepared by reacting the phenol compound 12 with acyl halides or isocyantes in appropriate solvents and temperatures. The biaryl ethers compound 202 can be prepared by treating compound 12 with aryl boronic acids in the presence of a copper catalyst.

Compounds of Scheme 3 can be converted to their corresponding hydroxamic acids following the methods outlined in Scheme 2.

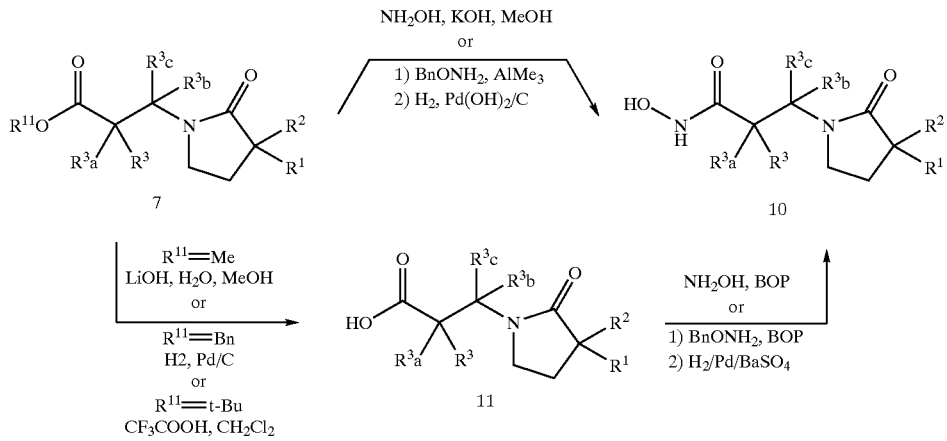

Scheme 2

Scheme 3

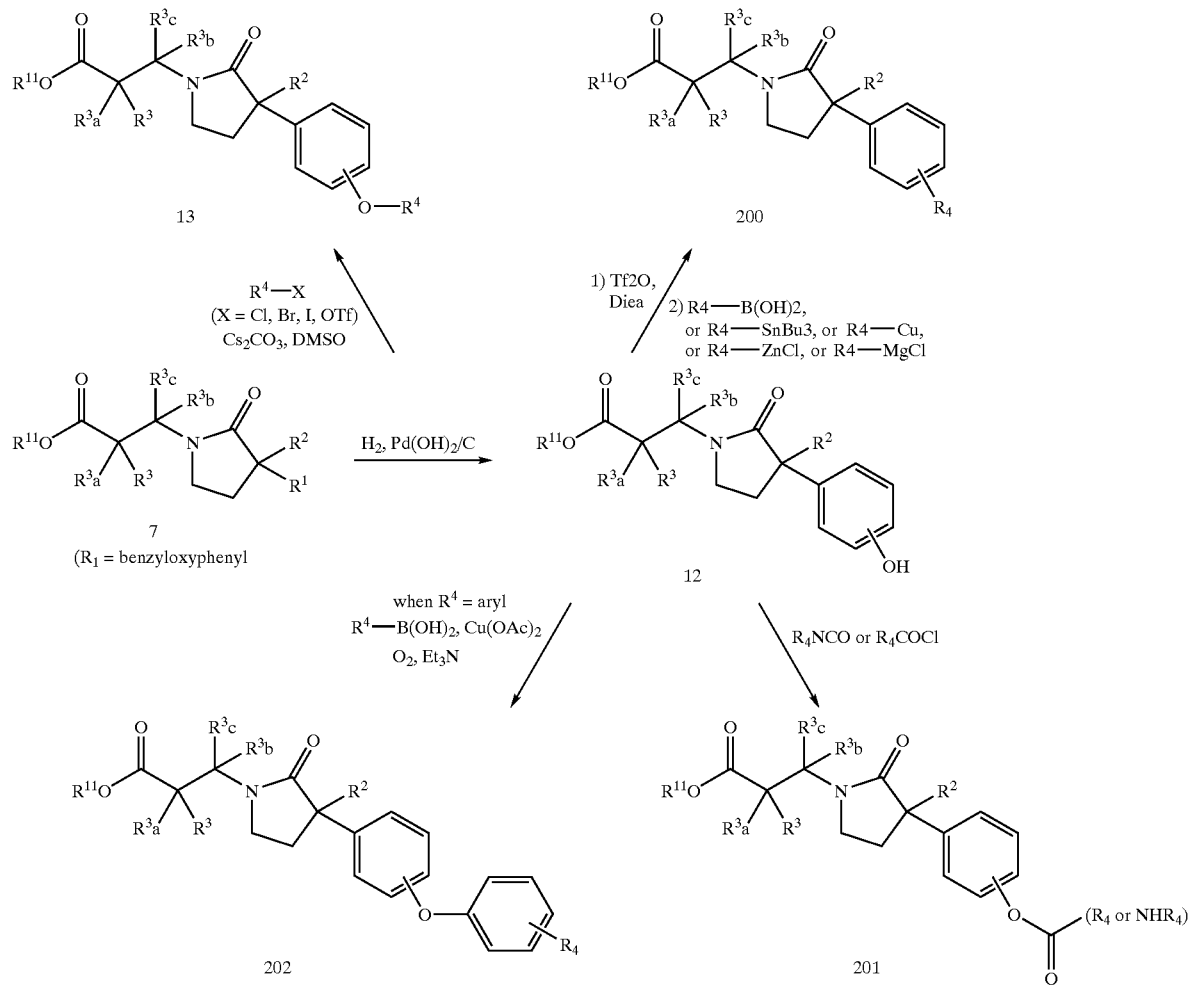

Another series of phenyllactams of formula 15 is prepared following the sequence outlined in Scheme 4. Starting from 7 when $R^1$ is phenyl methyl group, radical bromination with N-bromosuccinimide gives bromide 14. Alkylation of 14 with $R^4$—OH or $R^4$—NH2 under basic conditions gives 15a and 15b respectively. Ester 15 is converted to the hydroxamic acid following the sequences outlined in Scheme 2.

Scheme 4

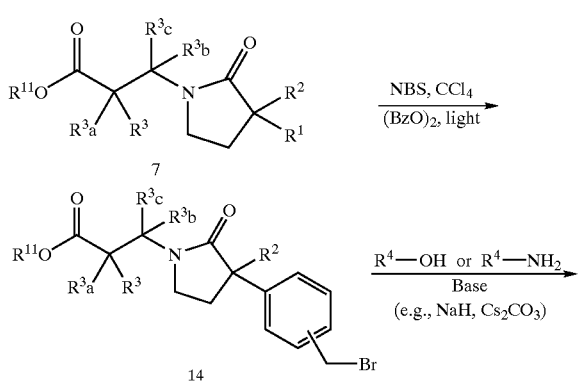

Another series of phenyl lactams of Formula 10 like those described in Scheme 5 can be prepared from compound 7 where R1 is nitrophenyl. The nitro group can be reduced to the aniline compound 210 by methods well known in the literature. The amine compound 211 can be prepared by reaction of compound 210 with an appropriately substituted aldehyde to give the imine that can be reduced by reagents such as sodium borohydride or sodium triacetoxyborohydride. Alternatively, the aniline compound 210 can be reacted with an appropriately substituted compound containing a leaving group like bromide or tosylate to give amine compound 211.

The sulfonamide compound 212 can be prepared by reaction of the aniline 210 with a substituted sulfonylchloride by methods well known in the literature. The amide compound 213 can be prepared by reacting the aniline 210 with an acid chloride or carboxylic acid with a coupling reagent used to make amide bonds previously described. The urea or carbamate compound 213 can be prepared from reacting the aniline 210 with an appropriately substituted isocyanate or chloroformate respectively. The compounds of Scheme 5 can be converted to their corresponding hydroxamic acids by methods described in Scheme 2.

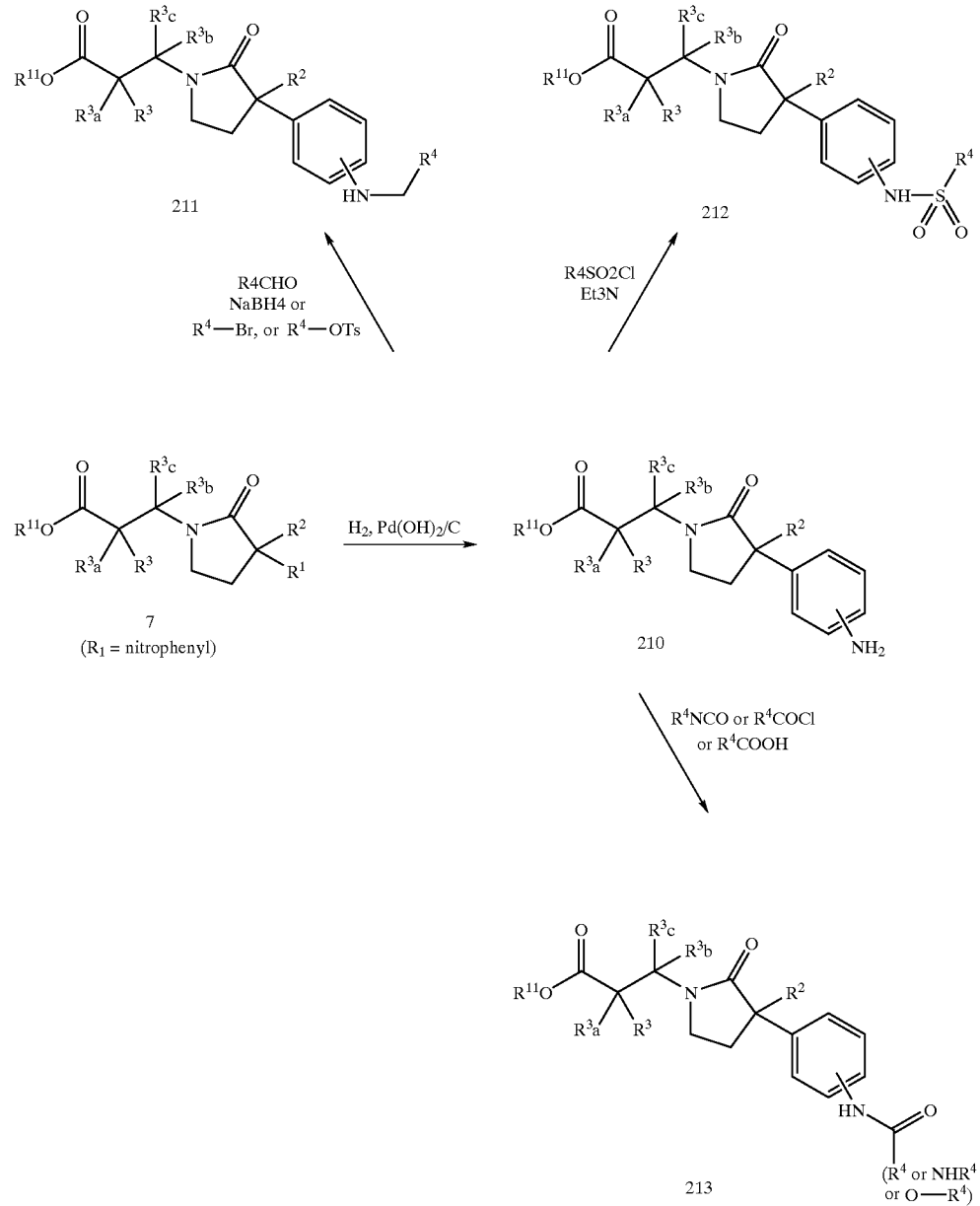

Scheme 5

A variety of heterocyclic substituted lactams are prepared from 7 when $R^1$ is carbobenzyloxy group. As a representative example, scheme 6 illustrates the synthesis of the benzimidazole series. Following hydrogenolysis of 7, the resultant acid 18 is coupled with diamine 19 with coupling reagents such as BOP—Cl. Upon heating of 20 in acetic acid, benzimidazole 21 is formed. Ester 21 is converted to the hydroxamic acid following the sequences outlined in Scheme 2.

Scheme 6

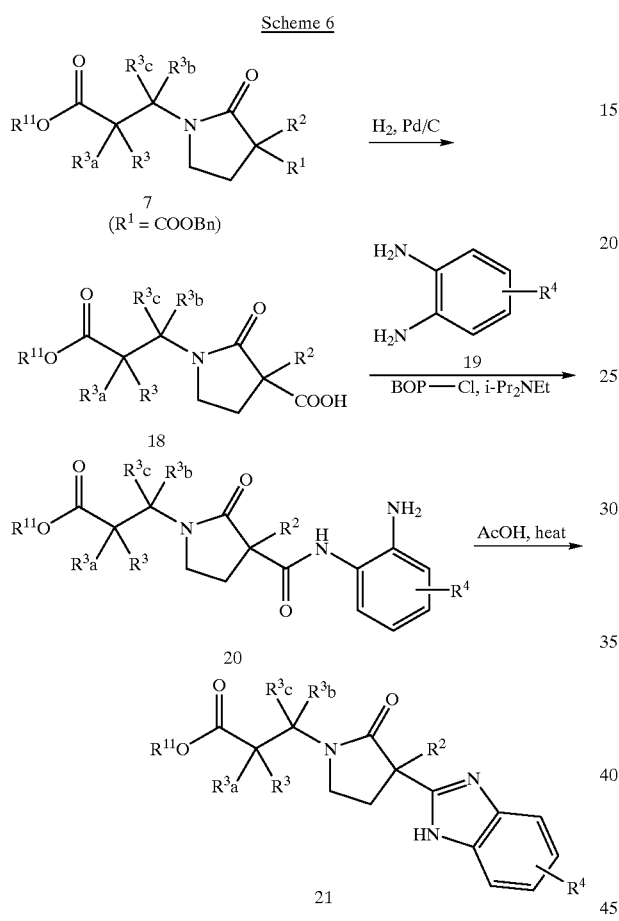

A series of isoxazole-substituted lactams of formula 26 is prepared using common intermediate 18 following the sequence outlined in Scheme 7. The carboxylic acid 18 is converted to aldehyde 23 by hydroboration and Swern oxidation. Oxime formation, in situ oxidation and [3+2] dipolar cycloaddition with acetylene 25 provides isoxazole 26. Ester 26 is converted to the hydroxamic acid following the sequences outlined in Scheme 2.

Scheme 7

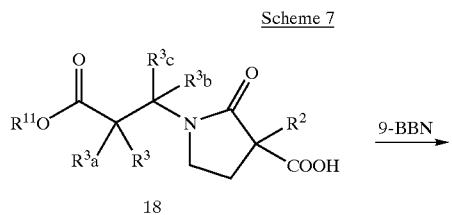

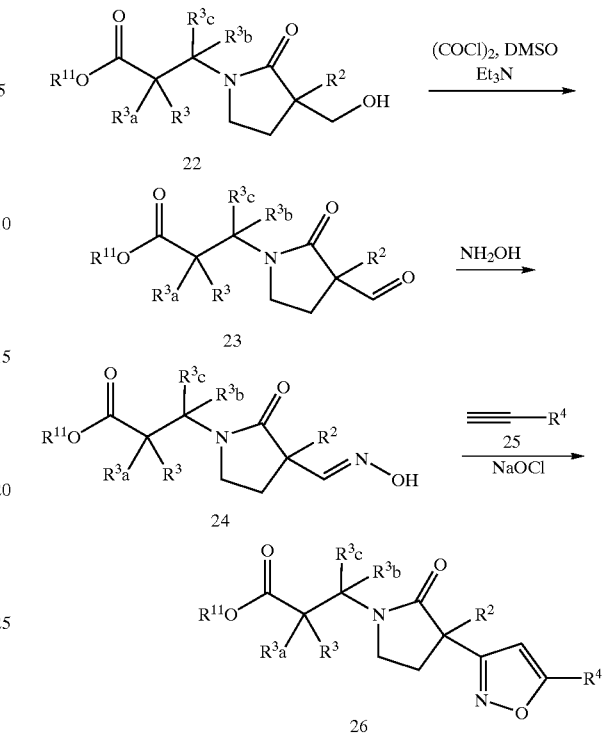

Another series of lactams of formula 30 with an oxadiazole substituent at the α position is prepared using common intermediate 18 following the sequence outlined in Scheme 8. Acid 18 is first coupled with hydrazine to give 27. Condensation with aldehyde 28 and oxidative cyclization with PhI(OAc)$_2$ provided oxadiazole 30 (Yang, R. Y.; Dai, L. X. *J. Org. Chem.* 1993, 58, 3381). Ester 30 is converted to the hydroxamic acid following the sequences outlined in Scheme 2.

Scheme 8

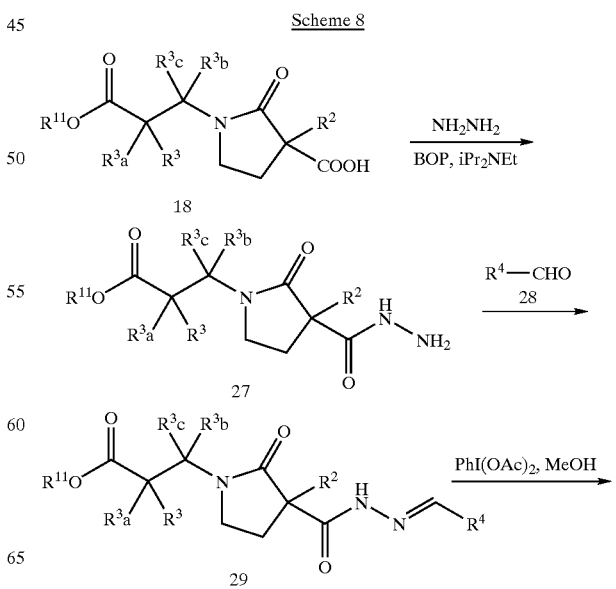

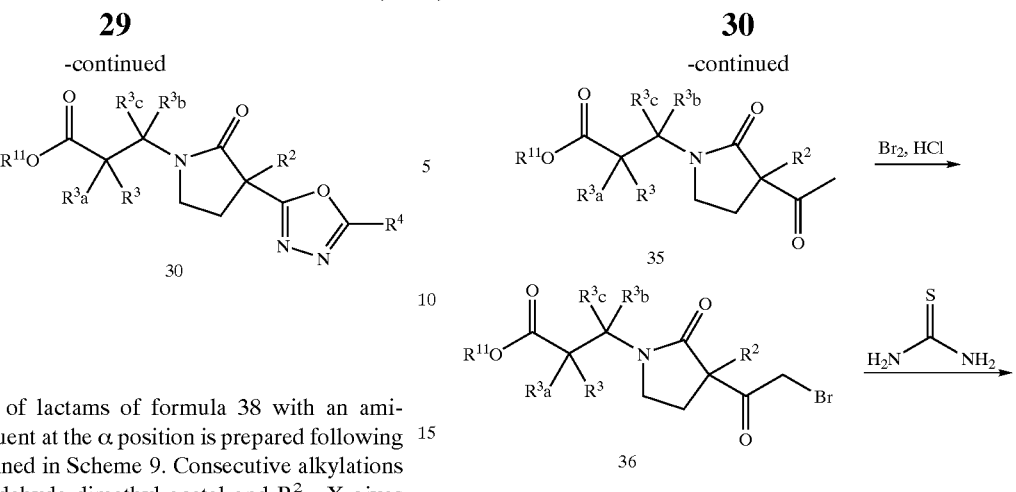

Another series of lactams of formula 38 with an aminothiazole substituent at the α position is prepared following the sequence outlined in Scheme 9. Consecutive alkylations with bromoacetaldehyde dimethyl acetal and R²—X gives 33. Reaction of 33 with β-amino acid 5 using zinc in acetic acid provides lactam 34. Bromoketone 36 is obtained from 34 by Wacker oxidation and bromination. Treatment of bromoketone 36 with thiourea produces aminothiazole 37 (Markees, D. G.; Burger, A. *J. Am. Chem. Soc.* 1948, 70, 3329). Alkylation with R⁴—X then provides 38. Ester 38 is converted to the hydroxamic acid following the sequences outlined in Scheme 2.

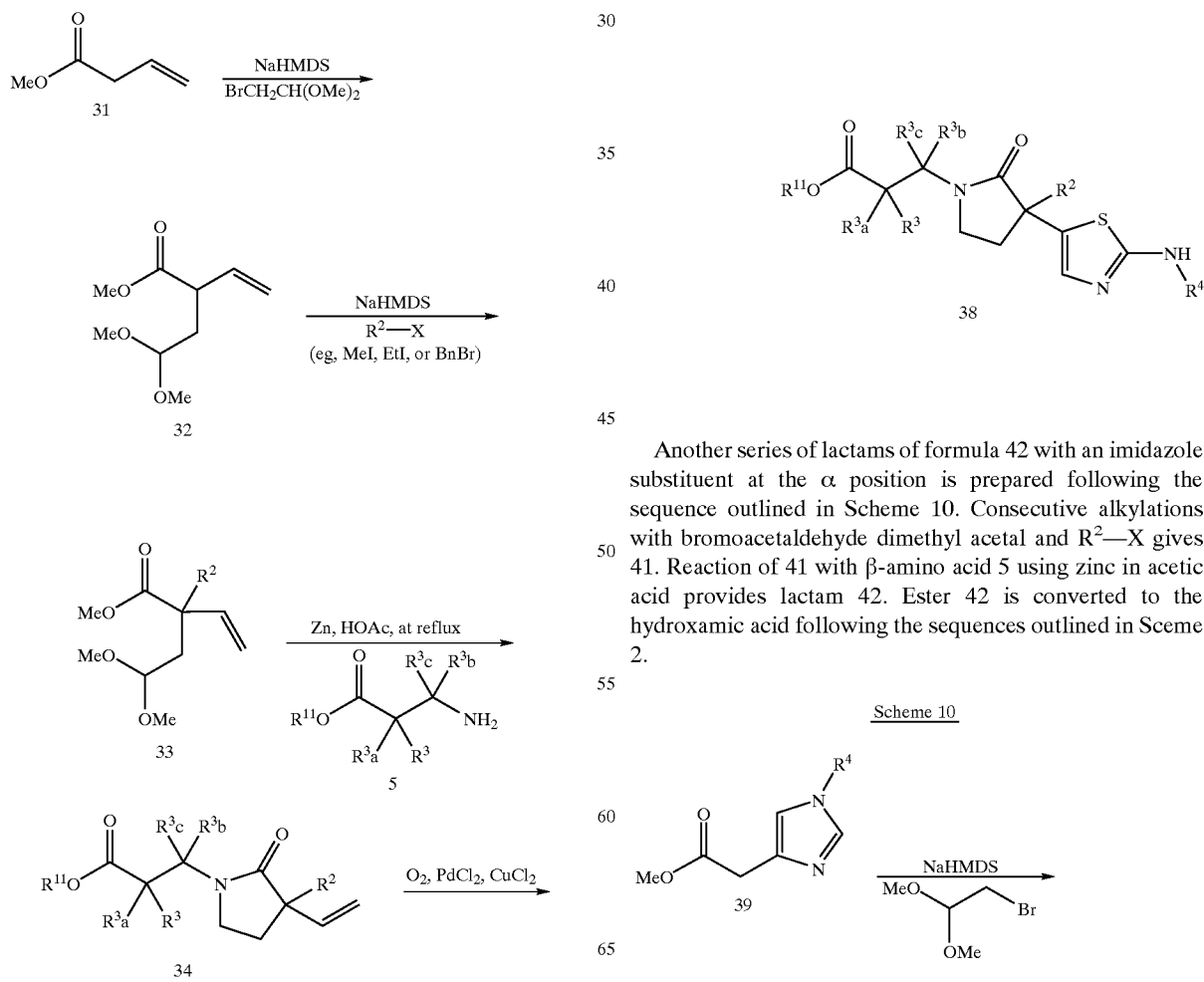

Another series of lactams of formula 42 with an imidazole substituent at the α position is prepared following the sequence outlined in Scheme 10. Consecutive alkylations with bromoacetaldehyde dimethyl acetal and R²—X gives 41. Reaction of 41 with β-amino acid 5 using zinc in acetic acid provides lactam 42. Ester 42 is converted to the hydroxamic acid following the sequences outlined in Sceme 2.

Scheme 10

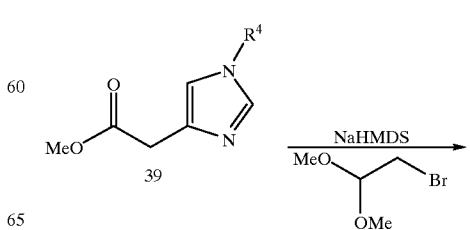

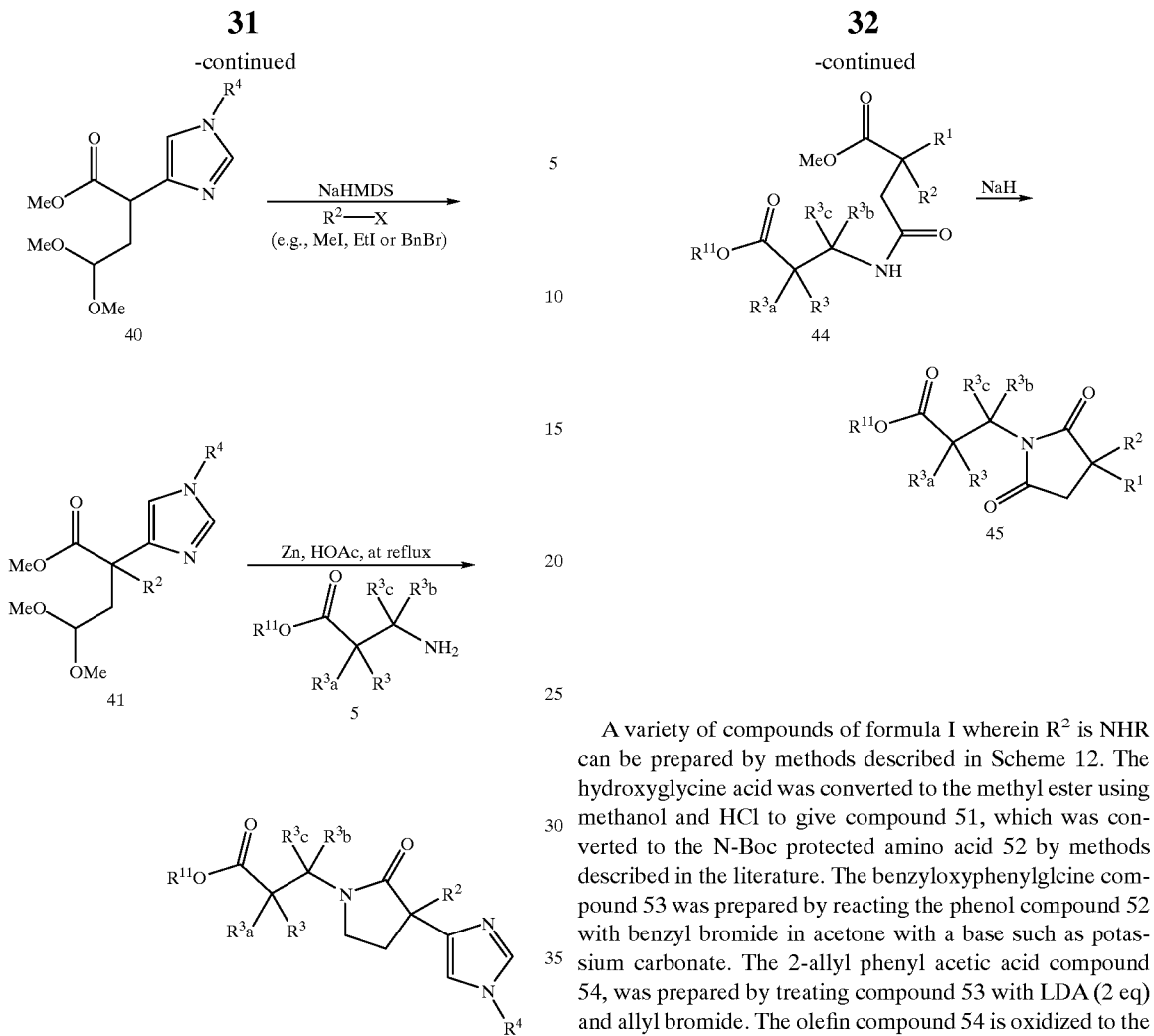

A series of succinimides of formula 42 is prepared from intermediate 4 (Scheme 11). The synthesis entails oxidation to carboxylic acid 43, coupling with β-amino acid 5, and succinimide formation. Ester 45 is converted to the hydroxamic acid following the sequences outlined in Scheme 2.

Scheme 11

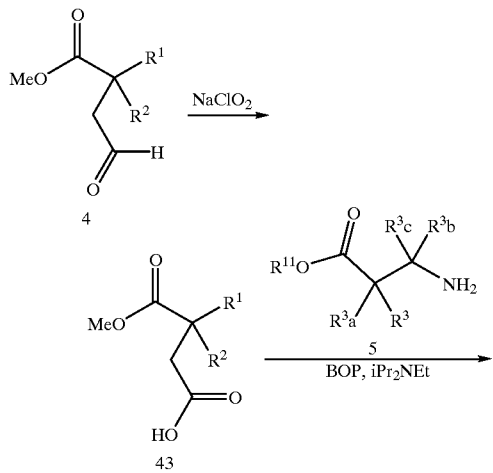

A variety of compounds of formula I wherein $R^2$ is NHR can be prepared by methods described in Scheme 12. The hydroxyglycine acid was converted to the methyl ester using methanol and HCl to give compound 51, which was converted to the N-Boc protected amino acid 52 by methods described in the literature. The benzyloxyphenylglcine compound 53 was prepared by reacting the phenol compound 52 with benzyl bromide in acetone with a base such as potassium carbonate. The 2-allyl phenyl acetic acid compound 54, was prepared by treating compound 53 with LDA (2 eq) and allyl bromide. The olefin compound 54 is oxidized to the aldehyde compound 55 using ozone and triphenylphosphine, then reacted with an appropriate amine to give the imine, which can be reduced with reagents similar to sodium triacetoxyborohydride, to give the amine compound 56. The γ-lactam compound 57 is prepared by heating the amine compound 56 in an appropriate solvent such as toluene. The benzyl ether is removed by methods well known in the literature such as hydrogenation using palladium on carbon in hydrogen, to give compound 58. The compound 59 is prepared by reacting the phenol 58 with an appropriately substituted halide or the like in acetone with a base such as potassium carbonate. The hydroxamic acid compound 61 was prepared from compound 59 by methods well known in the literature for removing N-Boc groups and conversion of the methyl ester previously described. Alternatively the amine compound 60 can be treated with appropriately substituted acid chloride, isocyanate, carboxylic acid with coupling agents such as carbonyldiimidazole or the like, that are well known in the literature for making amide bonds. Alternatively the amine of compound 60 can be converted to an isocyanate by a variety of methods known in the literature like using phosgene and a base such as sodium carbonate, and reacting this with an appropriately substituted amine, to give compound 62. The hydroxamic acid was prepared by methods previously described.

Scheme 12
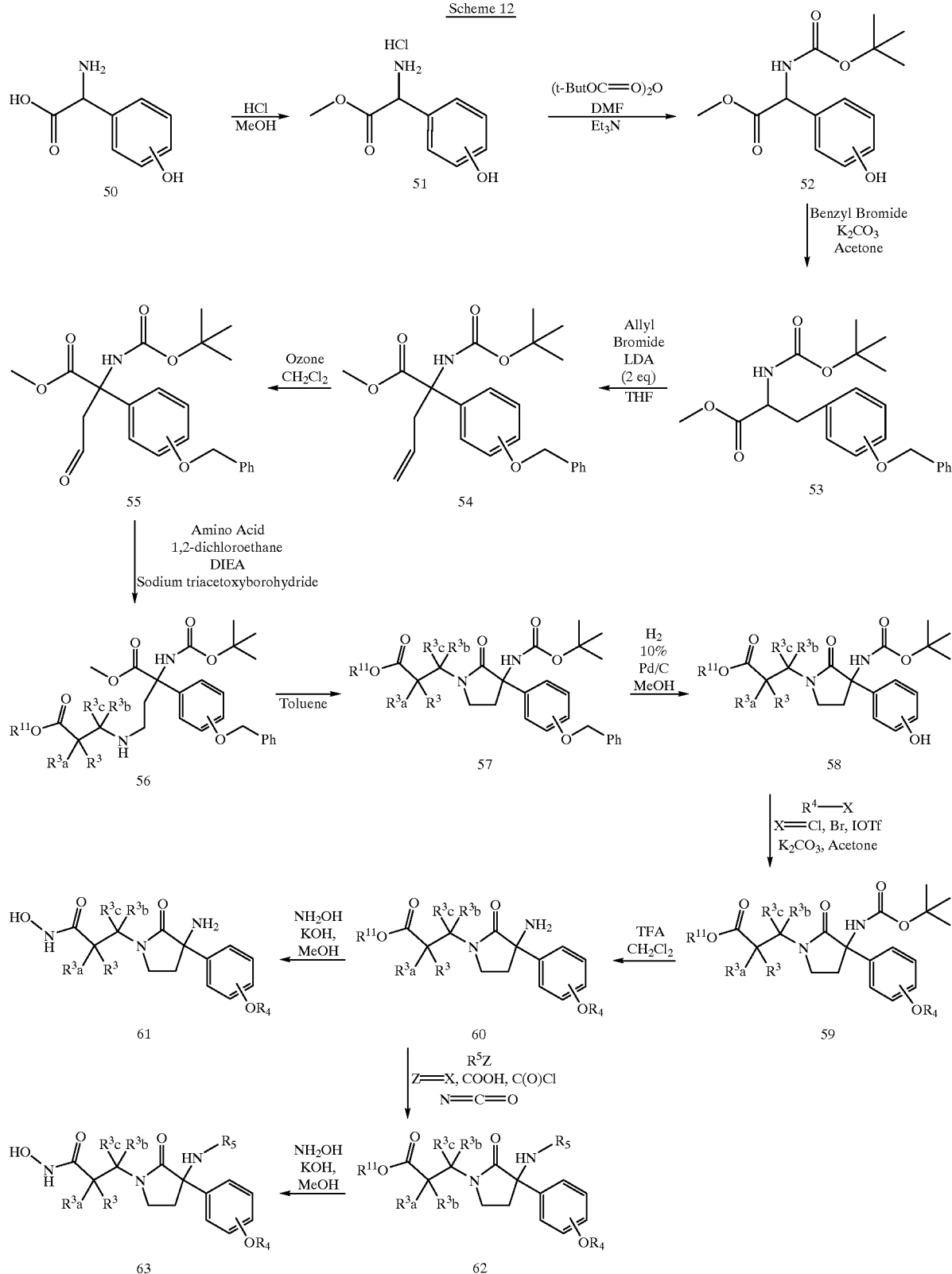
A variety of compounds of formula I wherein the lactam is a six member ring can be prepared by methods described in Scheme 13. The ester compound 64 is converted to the acid compound 65 by methods well known in the literature, such as lithium hydroxide in methanol water, then coupled to an appropriately substituted amine by methods well described in the literature for making amide bonds, such as TBTU and N-methyl morpholine in DMF, to give compound 66. The hydroxy compound 67 was prepared from the olefin compound 66 by reduction with 9-BBN and oxidative workup with hydrogen peroxide. The δ-lactam 69 is prepared by converting the hydroxy of compound 67 to a leaving group by methods well known in the literature such as carbon tetrabromide and triphenylphosphine in methylene chloride. The bromide compound 68 was reacted with a base such as sodium hydride in THF to give the δ-lactam 69. The hydroxamic acid compound 70 was prepared by methods previously described.

Scheme 13
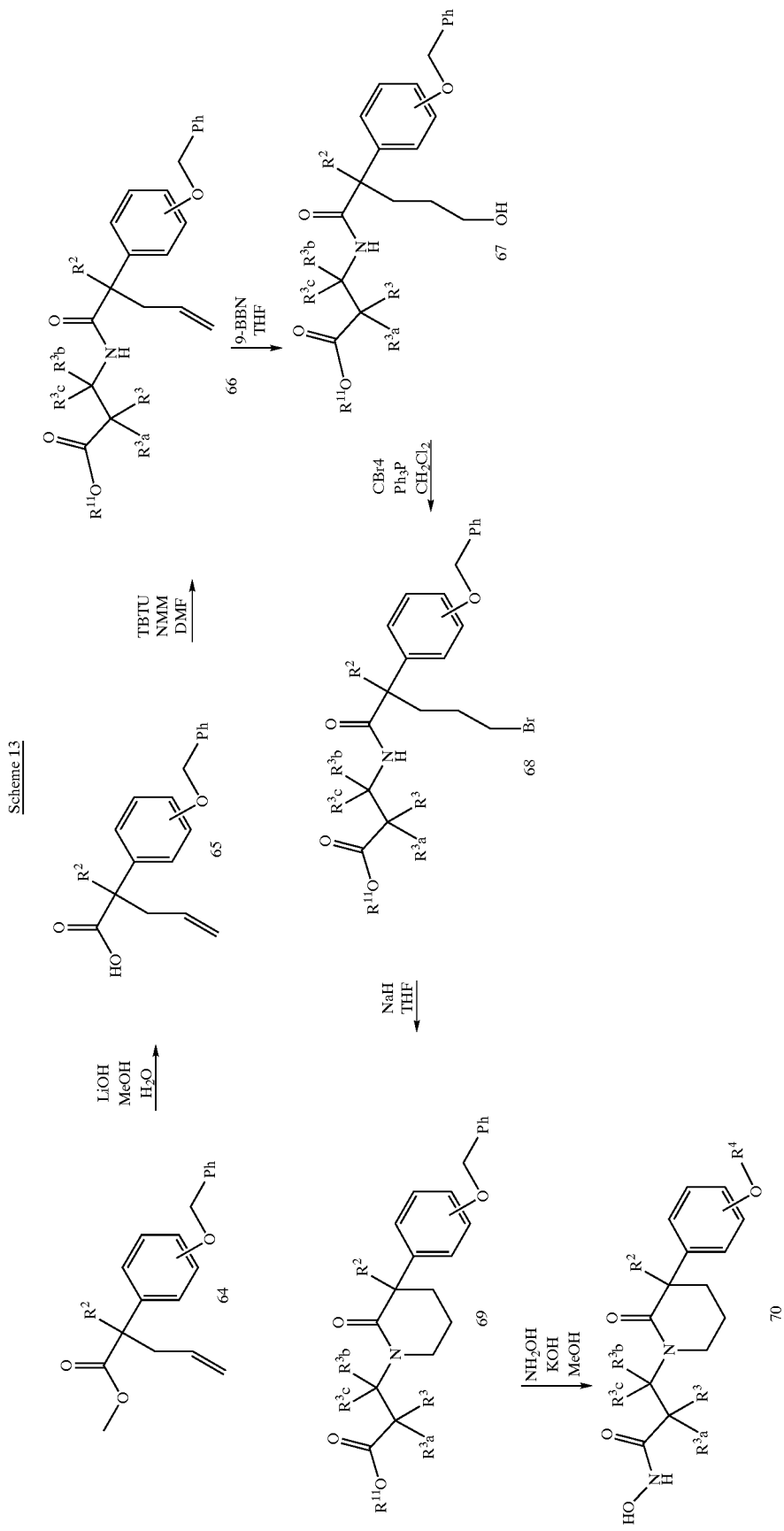

A variety of compounds of formula I wherein the lactam is a four member ring can be prepared by methods described in Scheme 14. The ester compound 71 was converted to the acid compound 72 and coupled to an appropriately substituted amine by methods well known in the literature and previously described. The β-lactam 75 is prepared by converting the hydroxy of compound 73 to a leaving group by methods well known in the literature, such as methanesulfonyl chloride and potassium carbonate in pyridine. The methanesulfonate compound 74 was reacted with a base such as potassium carbonate in acetone to give the β-lactam 75. The hydroxamic acid compound 77 was prepared by methods previously described.

Scheme 14
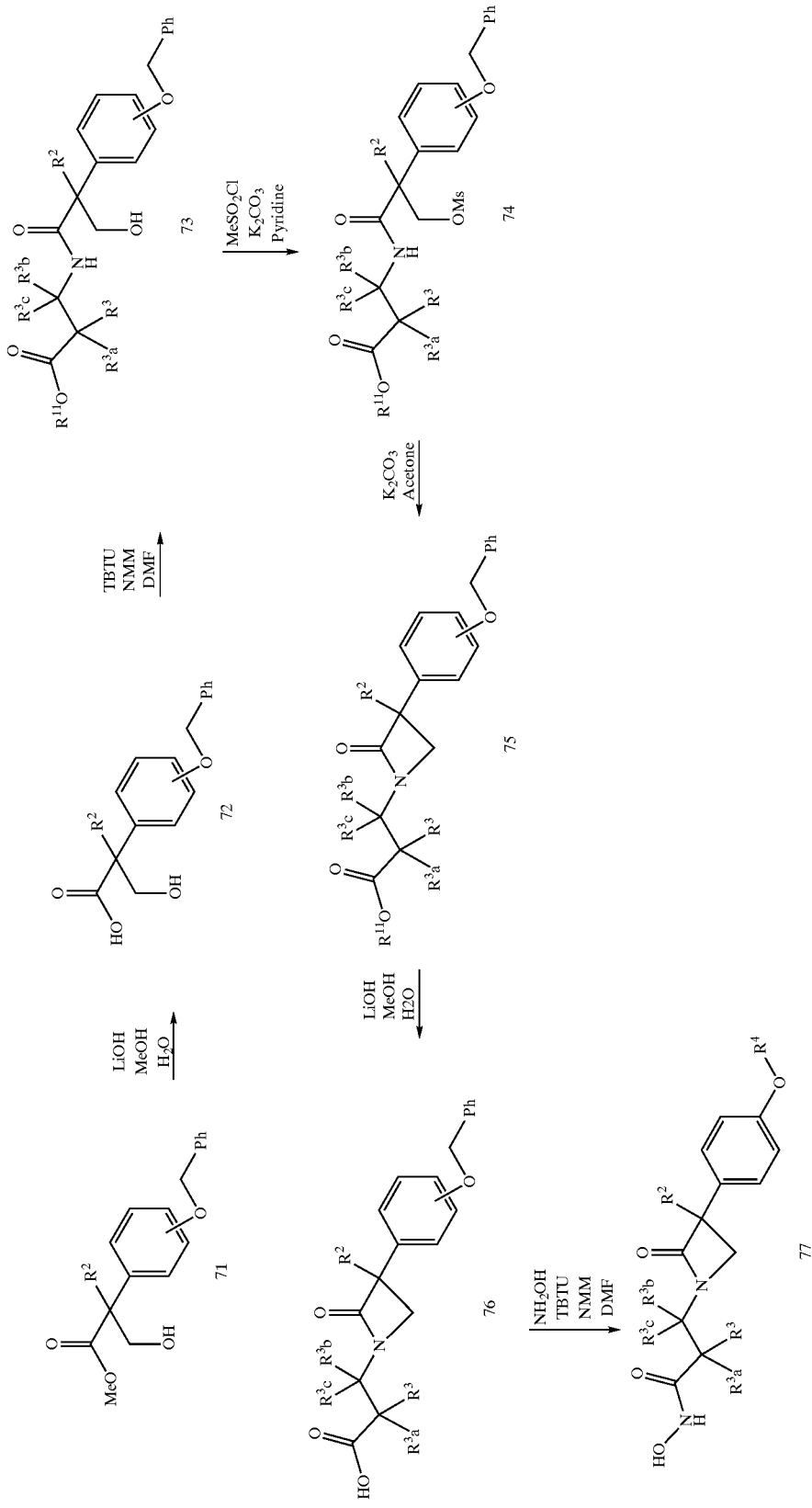

A variety of compounds of formula I wherein the lactam is replaced with a hydantoin ring can be prepared by methods described in Scheme 15. The amine compound 78 was prepared from the N-Boc compound 54 by methods previously described for the removal of Boc protecting groups. The urea compound 79 was prepared by converting the amine compound 78 to an isocyanate by methods well known in the literature and previously described, such as triphosgene and DIEA in methylene chloride and reacting this with an appropriately substituted amine. Alternatively, the amine 78 can be reacted with an isocyanate that is commercially available or can be prepared as described above. The hydantoin compound 80 was prepared by reacting the urea compound 79 with potassium carbonate in acetone. The final hydroxamic acid compound 81 was prepared by methods well documented previously.

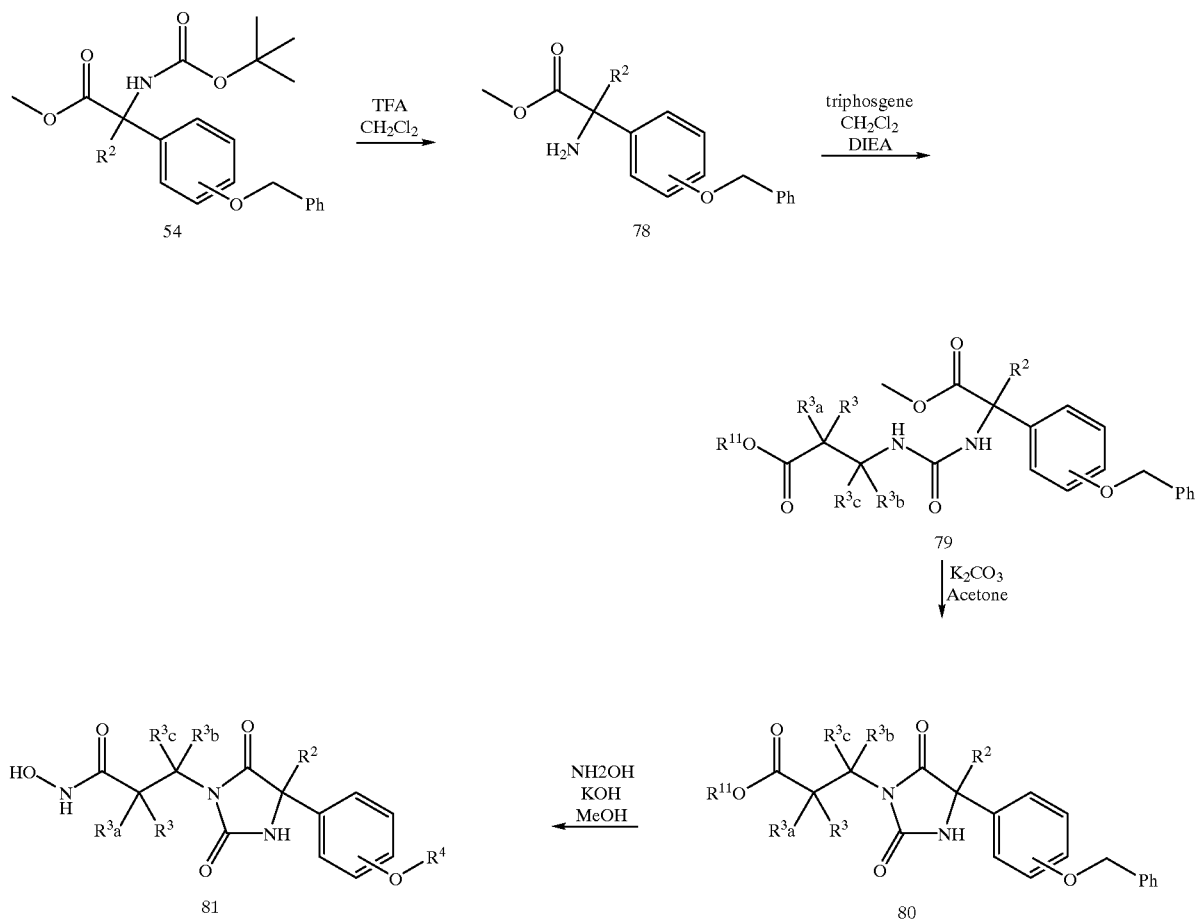

Scheme 15

A variety of compounds of formula I wherein the lactam is replaced with a imidazolinone can be prepared by methods described in Scheme 16. Compound 84 was prepared from the phenylglycine compound 82, by hydrolysis to the acid and coupling to an appropriately substituted amine as well described in the literature and previously detailed. The N-Boc group is removed by conventional methods previously described to give the amine compound 85. The heterocyclic compound 86 was prepared by reacting the amine compound 85 with paraformaldehyde in toluene at elevated temperatures. The final hydroxamic acid compound 87 was prepared by methods well documented previously.

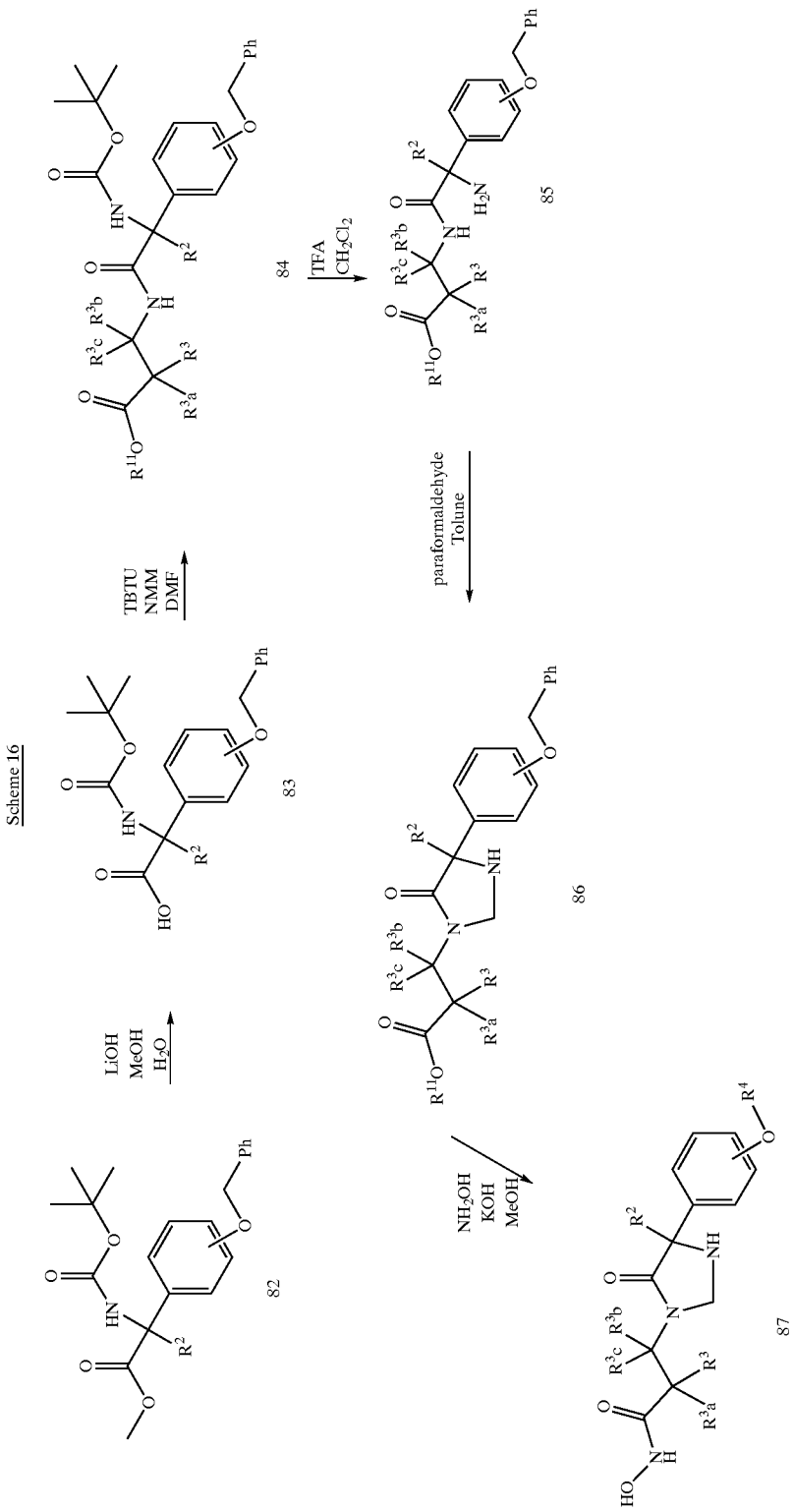

A variety of compounds of formula I wherein $R^2$ is $CH_2NHR$ can be prepared by methods described in Scheme 17. The cyanoacetate compound 89 was prepared by reacting the hydroxyphenylacetonitrile with benzyl bromide in acetone with potassium carbonate to give compound 88, which was in turn reacted with sodium ethoxide and diethylcarbonate in toluene at elevated temperatures. The allyl cyanoacetate compound 90 was prepared from the cyanoacetate compound 89 by generating the anion with a base such as sodium hydride and reacting this with allyl bromide in DMF. The nitrile lactam compound 94 was prepared by a sequence of steps previously described in several other Schemes. The N—Boc methyleneamine compound 96 was prepared by reduction of the nitrile lactam compound 94, using palladium on carbon with HCl in methanol, to give the amino compound 95 which was then protected by conventional methods with a Boc group to give compound 96. The final hydroxamic acid compounds 99 and 101 were prepared by methods previously described.

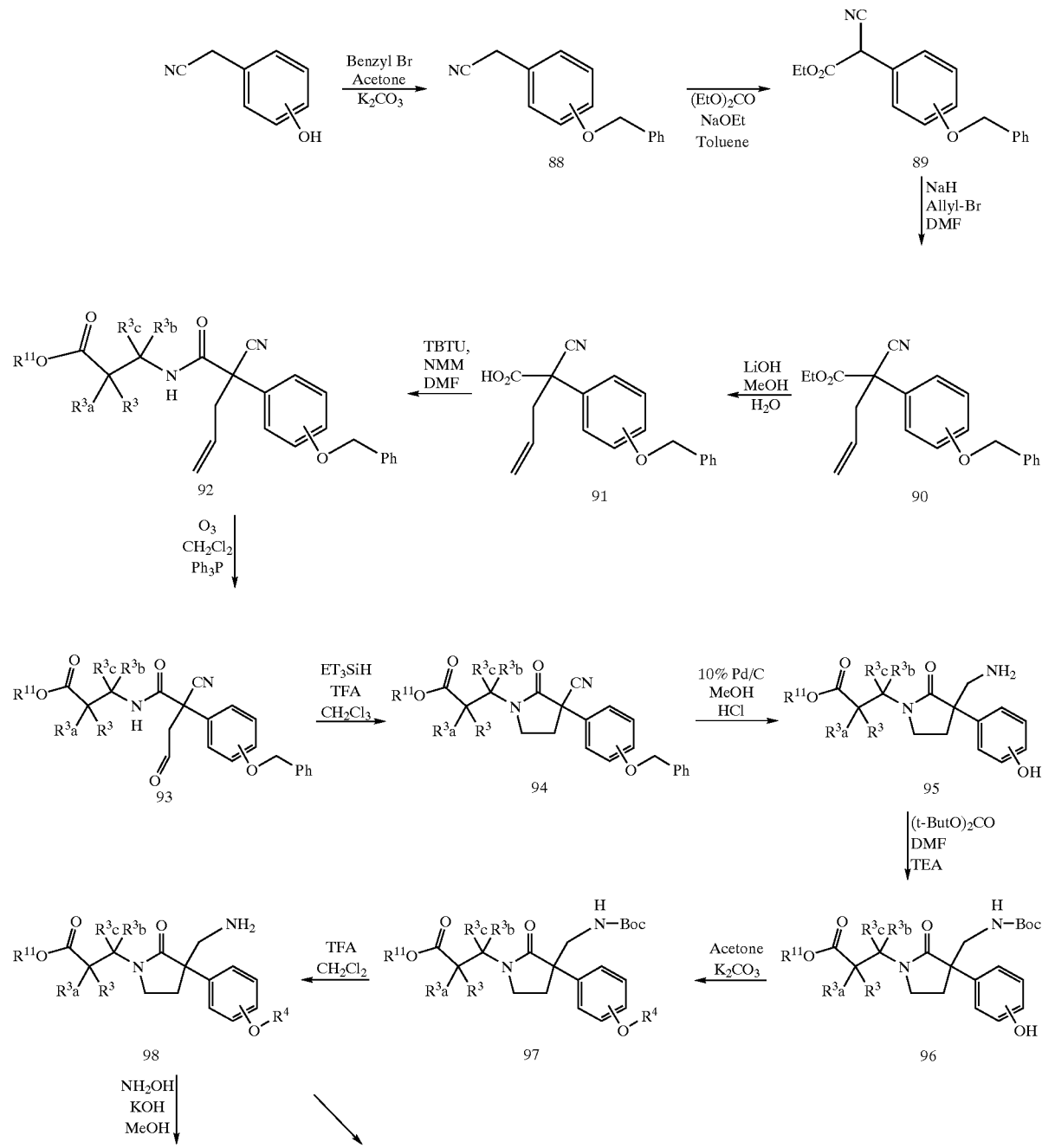

Scheme 17

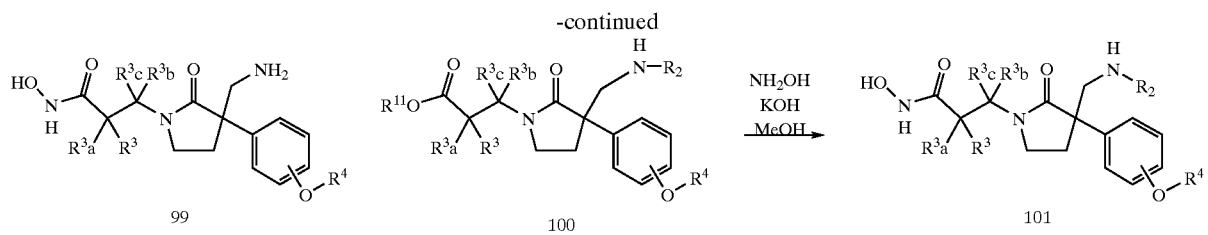

A variety of compounds of formula I wherein $R^2$ is $CH_2OH$ can be prepared by methods described in Scheme 18. The allyl compound 104 was prepared from hydroxyphenyl acetate, by reaction with benzyl bromide and potassium carbonate in acetone as previously described and then treating the benzyloxy phenyl acetate compound 103 with LDA and allyl bromide in THF. The methylene hydroxy compound 105 was prepared by treating the benzyloxy phenyl acetate compound 104 with paraformaldehyde and sodium methoxide in DMSO. The hydrolysis of the ester and coupling of the carboxylic acid to an appropriately substituted amine was described earlier to give the compound 107. The protected O-silyl compound 108 was prepared by methods well described in the literature, then oxidation to the aldehyde compound 109 with ozone was described previously. The lactam compound 110 was prepared from the aldehyde compound 109 by treatment with triethylsilane and TFA in methylene chloride at ambient temperatures. The final hydroxamic acid compound 112 was prepared by methods previously described.

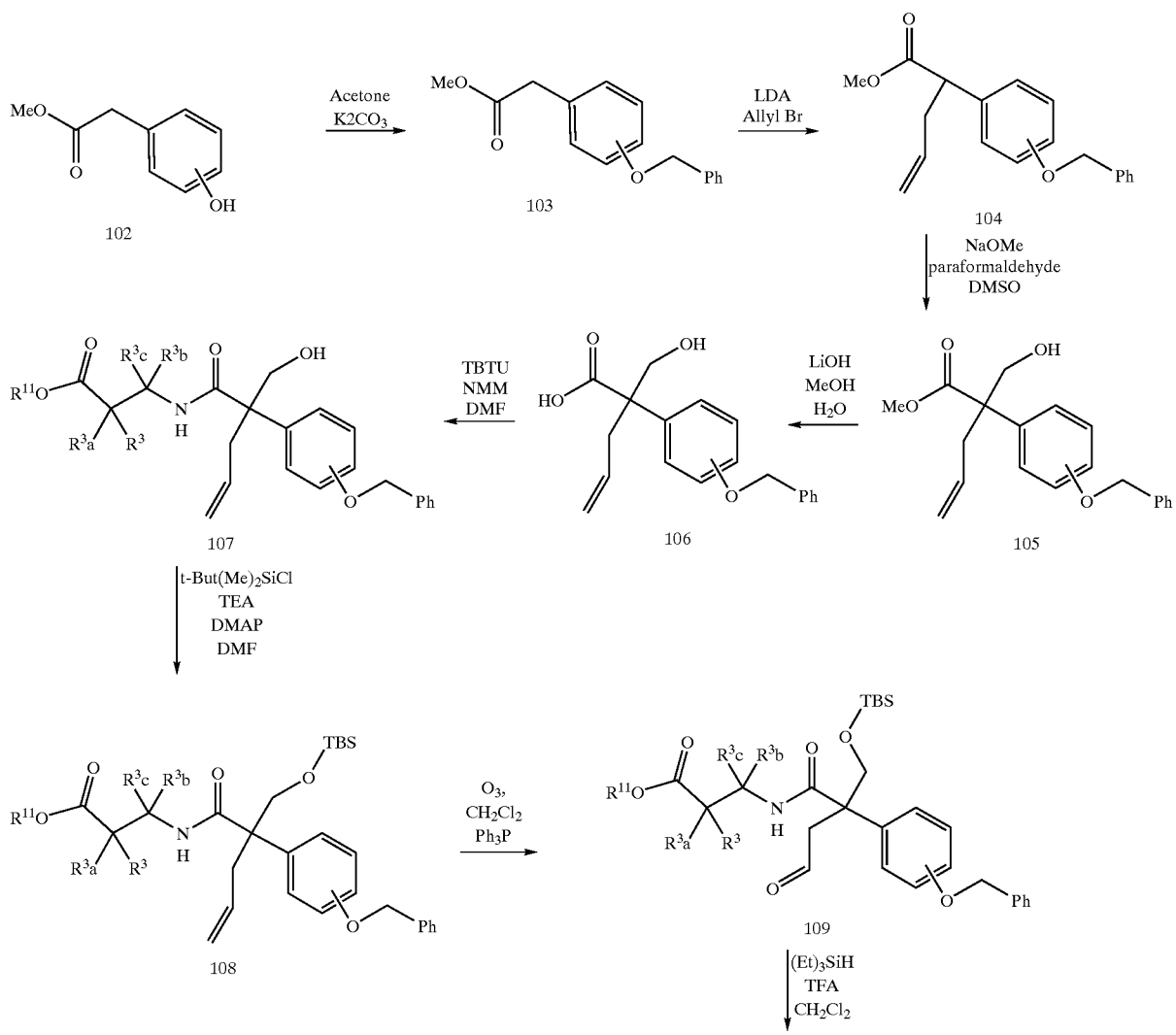

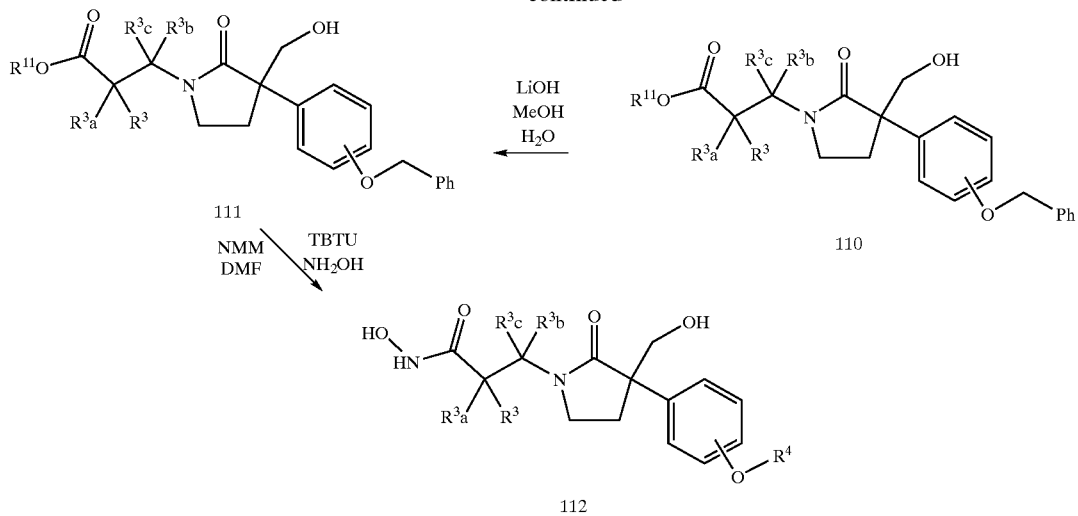

A variety of compounds of formula I wherein $R^1$ is a heterocycle, such as thiophene, can be prepared by methods described in Scheme 19. The thiophene substituted compound 115 was prepared by treating the thiophene acetate compound 113 with LDA and allyl bromide to give compound 114, and subsequently with LDA and methyl iodide in THF. The thiophene compound 117 was prepared by methods previously detailed for ester hydrolysis to the acid and coupling the carboxylic acid to an amine. The oxidation of the olefin compound 117, to the aldehyde compound 118, was performed by the action of osmium tetraoxide and NMMO, to give the diol, then treatment with NaIO4. The formation of the lactam ring compound 119 was previously described using triethylsilane and TFA in methylene chloride. The aldehyde thiophene compound 120 was prepared by chemistry well described in the literature, using phosphorus oxychloride in DMF. The aldehyde compound 120 was reacted with sodium borohydride in methanol to give alcohol compound 121 that was reacted with carbon tetrabromide and triphenyl phosphine to give the bromide compound 122. The bromide was treated with phenol and potassium carbonate in acetone to give the phenyl ether compound 123. The final hydroxamic acid compound 124 was prepared by methods previously described.

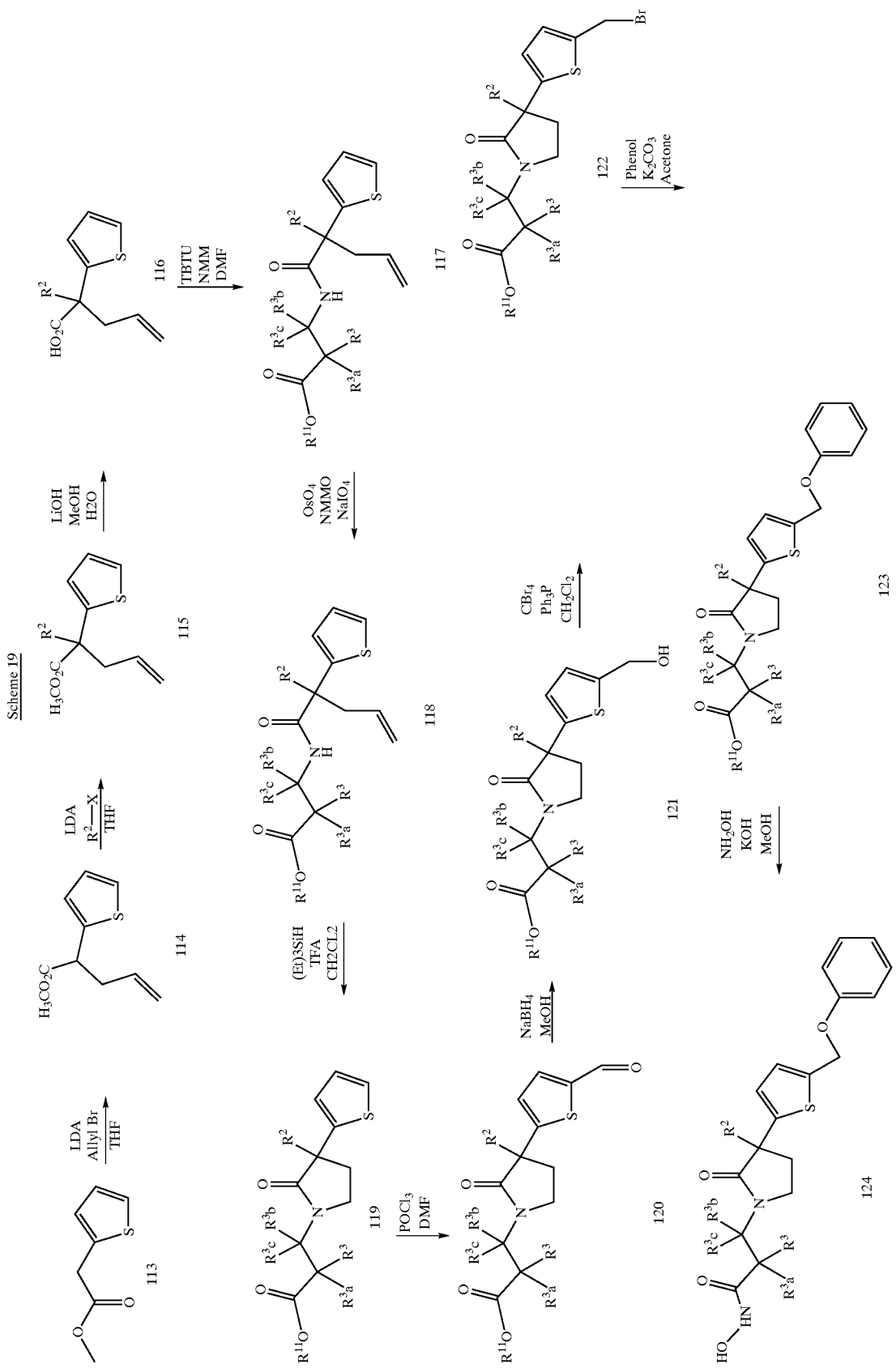

Another series of lactams of formula 135 is prepared following the sequence outlined in Scheme 20. Ester 124 is alkylated with t-butyl bromoacetate to give 126. Ester 126 is converted to 132 following previously described sequence. Removal of t-butyl group and coupling with NH$_2$R' under literature well known conditions gives 134. Ester 134 is converted to the hydroxamic acid following the sequences outlined in Scheme 2.

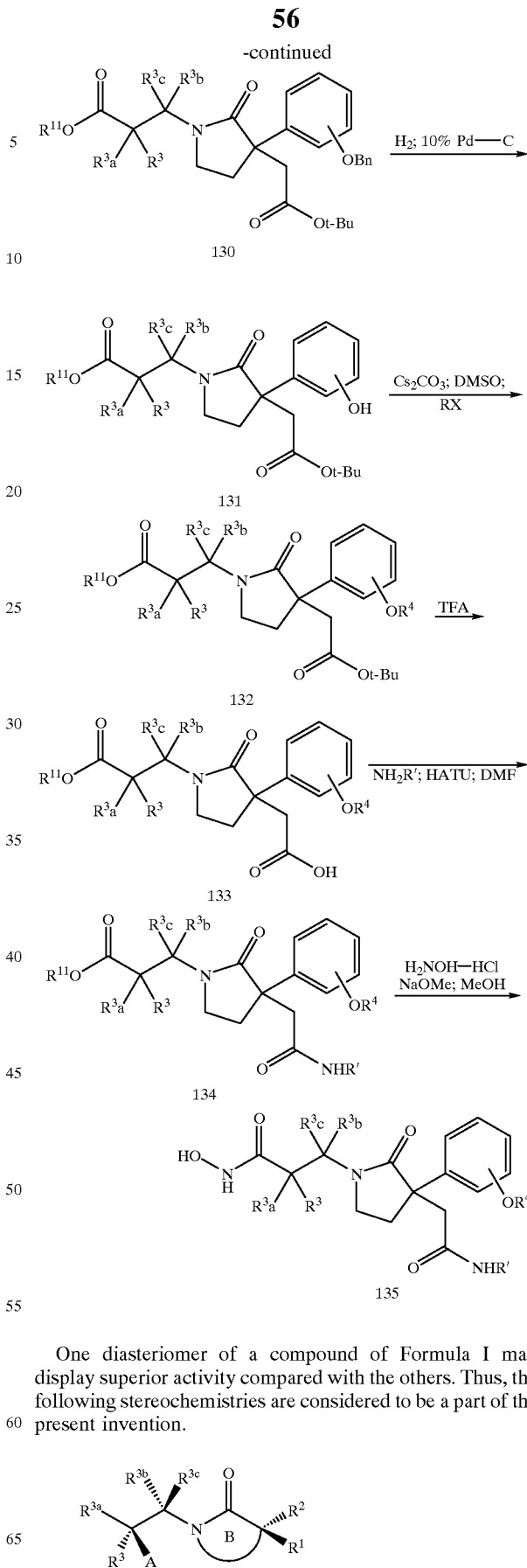

One diasteriomer of a compound of Formula I may display superior activity compared with the others. Thus, the following stereochemistries are considered to be a part of the present invention.

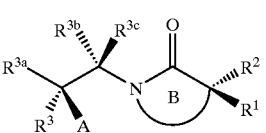

-continued

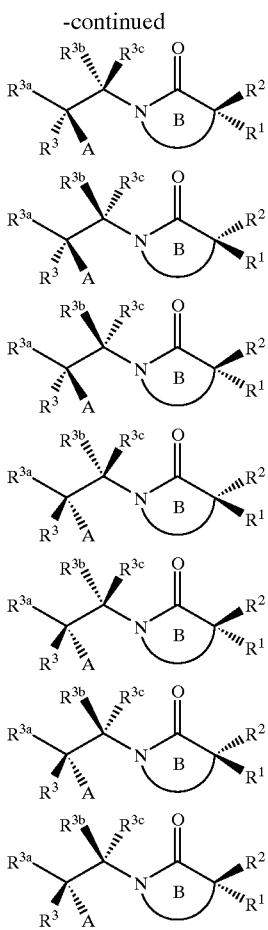

When required, separation of the racemic material can be achieved by HPLC using a chiral column or by a resolution using a resolving agent such as camphonic chloride as in Steven D. Young, et al, *Antimicrobial Agents and Chemotheraphy* 1995, 2602–2605. A chiral compound of Formula I may also be directly synthesized using a chiral catalyst or a chiral ligand, e.g., Andrew S. Thompson, et al, *Tet. Lett.* 1995, 36, 8937–8940.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "a", "b", "R" and "S" are stereochemical designations familiar to those skilled in the art.

Example 1

(1S-cis)-2-[3-amino-3-[4-[(2-methyl-4-quinolinyl)methoxy]phenyl]-2-oxo-1-pyrrolidinyl]-N-hydroxycyclohexanecarboxamide bis (trifluoroacetate) (salt)

(1a) Potassium t-Butoxide 1M in THF (80 mL) was added slowly to a solution of p-hydroxyphenyl glycine benzylimine (10.7 g, 36.2 mmol) in THF (250 mL) cooled to 0° C. under a nitrogen atmosphere. The reaction was stirred for 1 h, then allyl bromide (4.38 g, 36.2 mmol) was added slowly giving a slurry. The reaction was stirred for an additional hour then 4-chloromethyl 2-methyl quinoline (6.93 g, 36.1 mmol) and tetrabutyl ammonium iodide (20 mol %) was added. The reaction mixture was allowed to warm to 40° C. for 2 h then allowed to stir at RT overnight. 1N HCl (80 mL) and water (100 mL) were added to the reaction, stirred for 1 h and washed with ethyl ether (2×100 mL). The organic layer was back washed with 1N HCl (50 mL). The combined aqueous layers were neutralized with sodium hydroxide (50%) and extracted with ethyl acetate (3×150 mL). The combined ethyl acetate layers were dried over magnesium sulfate and concentrated to give a dark oil. The oil was taken up in 125 mL ethanol and methanesulfonic acid (2 eq) was added. This was stirred at RT to give a precipitate. The solids were collected and dried to give 2-allyl p-hydroxyphenyl glycine (12.1 g, 70%) as a yellow powder MS (M+H)$^+$=391.

(1b) Di-Boc (5.16 g, 23.68 mmol) was added to a solution of 2-allyl p-hydroxy phenyl glycine (1a) (11.5 g, 19.74 mmol), THF (100 mL), water (60 mL) and potassium carbonate (11.0 g, 78.9 mmol) at RT. The reaction was warmed to 60° C. for 48 h. The reaction was allowed to cool, diluted with ethyl acetate, washed with water, brine dried over magnesium sulfate and concentrated in vacuo. The product was purified by flash column chromatography on silica gel eluting hexane: ethyl acetate (60:40) to give the Boc protected phenyl glycine (7.5 g, 78%) as a white foam MS (M+H)$^+$=491.

(1c) Osmium tetraoxide (20 mol %) was added to a solution of the protected olefin (1b) (5.0 g, 10.2 mmol) and NMMO (1.79 g, 15.3 mmol) in THF (75 mL) and water (20 mL). The reaction was stirred vigorously overnight, diluted with ethyl acetate (100 mL), washed with 10% NaHSO3 (75 mL), brine, dried over magnesium sulfate and concentrated to give the intermediate diol. The diol was taken up in methylene chloride (75 mL) and sodium periodate 4.36 g, 20.4 mmol) in water (30 mL) was added. The reaction was stirred for 3 h and was diluted with methylene chloride (75 mL) and washed with water, brine, dried over magnesium sulfate and concentrated in vacuo to give the aldehyde (4.9 g, 97%) as a white foam MS (M+H)$^+$=493.

(1d) The aldehyde (1c) (0.5 g, 1.02 mmol) was combined with methyl cis 2-amino cyclohexane carboxylate (0.24 g, 1.21 mmol) and diisopropyl ethyl amine (0.39 mL, 2.24 mmol) in 1,2 dichloroethane (10 mL) at RT. The reaction was stirred for ½ h and the sodium triacetoxyborohydride was added. The reaction was stirred for 4 h, diluted with ethyl acetate, washed with brine, dried over magnesium sulfate and concentrated to give an oil. The crude amine was taken up in toluene (25 mL) under nitrogen and heated to reflux overnight. The reaction was concentrated and purified by flash chromatography on silica gel eluting methylene chloride: ethyl acetate (60:40) to give the lactam (0.34 g, 56%) as a glass MS (M+H)$^+$=588.

(1e) A solution of lithium hydroxide monohydrate (0.11 g, 2.7 mmol) in water (3 mL) was added to a solution of the lactam (1d) (0.32 g, 0.54 mmol) in methanol (15 mL) at RT. The reaction was warmed to 60° C. for 4 h, allowed to cool and was made acidic (pH 6) with acetic acid. The reaction was partitioned between ethyl acetate and water. The organic layer was washed with brine, dried over magnesium sulfate and concentrated to give the carboxylic acid (0.28 g, 91%) as off white foam MS (M+H)$^+$=574.

(1f) Isobutyl chloroformate (0.08 g, 0.58 mmol) was added to a solution of the carboxylic acid (1e) (0.28 g, 0.49 mmol), diisopropyl ethyl amine (0.19 g, 1.47 mmol) cooled to −30° C. under a nitrogen atmosphere. The reaction was stirred for ½ h and the hydroxylamine hydrochloride (0.068 g, 0.98 mmol) dissolved in DMF (2 mL) and diisopropyl ethyl amine (0.19 g, 1.47 mmol) was added. The reaction was stirred for 1 h, taken up in ethyl acetate washed with brine, dried over magnesium sulfate and concentrated to give the hydroxamic acid (0.28 g, 100%) as an oil MS $(M+H)^+$=589.

(1g) The Boc protected (1f) (0.28 g, 0.49 mmol) was taken up in methylene chloride (2 mL) and trifluoroacetic acid (2 mL) under nitrogen at RT. The reaction was stirred for 2 h, concentrated in vacuo and purified by reverse phase HPLC on a Vydac C-18 column, eluting with an acetontrile:water-:TFA gradient to give the title compound (0.11 g, 45%) as a white amorphous solid MS $(M+H)^+$=489.

Example 2

(1S-trans)-2-[3-amino-3-[4-[(2-methyl-4-quinolinyl) methoxy]phenyl]-2-oxo-1-pyrrolidinyl]-N-hydroxycyclohexanecarboxamide bis (trifluoroacetate) (salt)

(2a) Following the procedures analogous to that used for the preparation of example (1a–1d), but using methyl trans-2-aminocyclohexanecarboxylate in step (1d) the protected lactam was prepared (0.22 g, 81%) as a white foam. MS $(M+H)^+$=588.

(2b) Following the procedures analogous to that used for (1g) but using the Boc protected lactam (2a) (0.22 g, 0.37 mmol) the cyclohexane methyl ester (0.21 g, 80%) was prepared as a glass MS $(M+H)^+$=488.

(2c) A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M. The freshly prepared 1.76 M solution of hydroxylamine (1 mL) was added to the methyl ester from (2b) (0.05 g, 0.07 mmol) in methanol (1 mL) at RT. After 1 h at this temperature the reaction was complete. It was acidified to pH 6–7 with TFA and concentrated. The product was purified by reverse phase HPLC on a Vydac C-18 semiprep column eluting an acetonitrile:water:TFA gradient, to give the hydroxamic acid product (0.03 g, 60%) as a white amorphous solid. MS $(M+H)^+$=489, MS $(M-NH_2)^+$=472

Example 3

(1S-trans)-2-[3-amino-3-[4-[(2-methyl-4-quinolinyl) methoxy]phenyl]-2-oxo-1-pyrrolidinyl] cyclohexanecarboxylic acid bis(trifluoroacetate) (salt)

(3a) Following the procedures analogous to that used for the preparation of example (1a–e and 1g), but using methyl trans-2-aminocyclohexanecarboxylate in step (1d) and the title compound was prepared. The product was purified by reverse phase HPLC on a Vydac C-18 semiprep column eluting an acetonitrile:water:TFA gradient, to give the carboxylic acid product (0.12 g, 34%) as a white amorphous solid. MS $(M+H)^+$=474, MS $(M-NH_2)^+$=457.

Example 4

(1S-cis)-2-[(3S)-3-amino-3-[4-[(2-methyl-4-quinolinyl) methoxy]phenyl]-2-oxo-1-pyrrolidinyl] cyclopentanecarboxylic acid bis(trifluoroacetate) (salt)

(4a) Following the procedures analogous to that used for the preparation of example (1a–d), but using methyl cis-2-aminocyclopentanecarboxylate in step (1d) the protected cylopentyl γ-lactam compound (2.1 g, 50%) was prepared as a white foam MS $(M+Na)^+$=596.

(4b) The protected cylopentyl γ-lactam compound (1.9 g, 3.3 mmol) was dissolved in concentrated hydrochloric acid (30 mL) and heated to 60° C. for 6 h. The reaction was allowed to cool to RT taken up in acetonitrile (50 mL) and reconcentrated (3×) to give a yellow powder. The crude compound (0.20 g) was purified by reverse phase HPLC on a Vydac C-18 semiprep column eluting an acetonitrile:water:TFA gradient, to give the title carboxylic acid product (0.12 g, 60%) as a white amorphous solid MS $(M+H)^+$=460.

Example 5

(1S-cis)-2-[(3S)-3-amino-3-[4-[(2-methyl-4-quinolinyl) methoxy]phenyl]-2-oxo-1-pyrrolidinyl]-N-hydroxycyclopentanecarboxamide bis (trifluoroacetate) (salt)

(5a) The carboxylic acid compound from (4b) (1.4 g, 2.63 mmol) was combined with the BOP coupling agent (1.7 g, 3.9 mmol), hydroxylamine hydrochloride (1.8 g, 26 mmol) and diisopropyl ethyl amine (6.8 mL, 39 mmol) in DMF (50 mL) under nitrogen at RT. The reaction was stirred for 24 h, concentrated in vacuo to give an oil. The oil was triturated in acetonitrile (50 mL) and TFA (3 mL) to give a powder. The solids were taken up in water, washed with ethyl acetate (2×), and the pH was adjusted to 7.5 to give a precipitate. The solids were collected and dried to give the title compound (0.95 g, 77%) as an off white solid MS $(M+H)^+$=475.

Example 6

(1R-trans)-2-[(3S)-3-amino-3-[4-[(2-methyl-4-quinolinyl) methoxy]phenyl]-2-oxo-1-pyrrolidinyl]-N-hydroxycyclopentanecarboxamide bis (trifluoroacetate) (salt)

(6a) Following the procedures analogous to that used for the preparation of example (4a), and (2b,2c) the racemized hydroxamic compound was prepared. The crude trans compound was purified by reverse phase HPLC on a Vydac C-18 semiprep column eluting an acetonitrile:water:TFA gradient, to give the title hydroxamic acid product (0.08 g, 32%) as a white amorphous solid MS $(M+H)^+$=475.

Example 7

(1S-cis)-2-[(3S)-3-amino-3-[4-[(2-methyl-4-quinolinyl) methoxy]phenyl]-2-oxo-1-pyrrolidinyl]-N-hydroxy-4,4-dimethylcyclopentanecarboxamide bis(trifluoroacetate) (salt)

(7a) Triethyl amine (1.1 mL, 7.89 mmol) was added slowly to a clear solution of dimedone (1.0 g, 7.13 mmol) and trisylazide (3.3 g, 10.69 mmol) in methylene chloride (30 mL), cooled in an ice bath under a nitrogen atmosphere. The reaction was allowed to stir for 1 h and warmed to RT for an additional 3 h. The reaction was concentrated to give an oil. The product was purified by flash chromatography on silica gel eluting hexane:ethyl acetate (70:30) to give the diazodimedone compound (1.1 g, 92%) as an oil MS $(M+CH_3CN)^+$=208.

(7b) The diazodimedone (7a) (1.1 g, 6.6 mmol) was dissolved in methanol (100 mL) in a quartz flask. The reaction was irradiated in a UV light chamber for 3 h. The reaction was concentrated to give the methyl 2-oxo-4,4-dimethylcyclopentylcarboxylate (1.1 g, 100%) as an oil MS $(M+H)^+$=171.

(7c) O-benzyl hydroxylamine hydrochloride (2.46 g, 15.4 mmol) was added to a solution of methyl 2-oxo-4,4-dimethylcyclopentylcarboxylate (1.1 g, 6.4 mmol) in methanol (30 mL) and potassium carbonate (4.25 g, 30.8 mmol). The reaction was stirred overnight, becoming a thick slurry. This was diluted with ethyl acetate filtered, washed with water, brine, dried over magnesium sulfate and concentrated to give an oil. The product was purified by flash chromatography on silica gel eluting hexane: ethyl acetate (90:10) to give the oxime (1.2 g, 68%) as an oil MS (M+H)$^+$=276.

(7d) The oxime (7c) was taken up in methanol (50 mL) and HCl conc. (2 mL) in a Parr shaker bottle. The reaction was degassed, 10% Pd/C (1 g) was added and charged to 60 psi hydrogen pressure. The reaction was shaken over night, filtered and concentrated to give the methyl 2-amino-4,4-dimethylcyclopentanecarboxylate (0.71 gm, 93%) as an oil MS (M+H)$^+$=172.

(7e) Following the procedures analogous to that used for the preparation of example (5), but using methyl 2-amino-4,4-dimethylcyclopentanecarboxylate for (4a) the title compound was prepared. The crude compound was purified by reverse phase HPLC on a Vydac C-18 semiprep column eluting an acetonitrile: water: TFA gradient, to give the title hydroxamic acid product (0.10 g, 37%) as a white amorphous solid MS (M+H)$^+$=503.

Example 8

(1S-cis)-1-[(3S)-3-amino-3-[4-[(2-methyl-4-quinolinyl) methoxy]phenyl]-2-oxo-1-pyrrolidinyl]-2,3-dihydro-N-hydroxy-1H-indene-2-carboxamide bis(trifluoroacetate) (salt)

(8a) Methyl acetoacetate (2.0 g, 15.3 mmol) was added to a solution of sodium ethoxide (3.1 g, 45.9 mmol) and ethanol (50 mL) under nitrogen at RT. The reaction was stirred for ½ h and the bromomethyl benzonitrile (3.0 g, 15.3 mmol) was added. The reaction was heated to reflux overnight, allowed to cool, concentrated, the residue was taken up in ethyl acetate washed with water, brine, dried over magnesium sulfate and concentrated to give an oil. The oil was purified by flash chromatography on silica gel eluting hexane: ethyl acetate (80:20) to give the olefin product (1.3 g, 43%) as an oil MS (M+H)$^+$=204.

(8b) The olefin compound (8a) (1.62 g, 7.97 mmol) was dissolved in methanol, degassed with nitrogen, 10% Pd/C was added and the reaction was charged to 55 psi hydrogen. The reaction was shaken for 4 days, was filtered and concentrated to give a colorless oil. The product was purified by flash chromatography on silca gel eluting methylene chloride: methanol (95:5) to give the amino compound (1.5 g, 94%) as an oil MS (M+H)$^+$=192.

(8c) Following the procedures analogous to that used for the preparation of example (5), but using the amino compound from (8b) the title compound was prepared. The crude compound was purified by reverse phase HPLC on a Vydac C-18 semiprep column eluting an acetonitrile: water: TFA gradient, to give the title hydroxamic acid product (0.05 g, 20%) as a white amorphous solid MS (M+H)$^+$=523.

Example 9

(3R-trans)-4-[(3S)-3-amino-3-[4-[(2-methyl-4-quinolinyl) methoxy]phenyl]-2-oxo-1-pyrrolidinyl]-tetrahydro-N-hydroxy-3-furancarboxamide bis(trifluoroacetate) (salt)

(9a) Dimethyl 3,4-furandicarboxylate (5.20 g, 28.0 mmol) was combined with 5% Rhodium/C in methanol (30 mL) and ethyl acetate (10 mL) in a Parr shaker bottle. The reaction was charged to 50 psi hydrogen and was shaken for 8.5 h. The reaction was filtered over celite, concentrated in vacuo to give the dimethyl 3,4-tetrahydrofuran dicarboxylate (5.2 g, 100%) as an oil MS (M−CH$_3$OH)$^+$=156.

(9b) Lithium hydroxide (1.32 g, 31.4 mmol) dissolved in water (20 mL) was added to a solution of dimethyl 3,4-tetrahydrofuran dicarboxylate (9a) (5.2 g, 28.0 mmol) in methanol (40 mL) at RT under a nitrogen atmosphere. The reaction was stirred for 4 h, concentrated, made acidic with 1N HCl and extracted with ethyl acetate (2×100 mL). The combined organic layer was washed with brine, dried over magnesium sulfate and concentrated to give the mono acid (3.75 g, 77%) as an oil MS (M+H)$^+$=175.

(9c) Diphenylphosphorylazide (5.9 g, 21.5 mmol) was added to a solution of the mono acid (9b) (3.75 g, 21.5 mmol) in toluene (50 mL) and triethyl amine (4.3 g, 43 mmol). The reaction was heated to 90° C. for 2 h and then benzyl alcohol (3.4 g, 32.2 mmol) was added. The reaction was heated to 90° C. overnight, cooled to RT, concentrated in vacuo, and partitioned between ethyl acetate and water. The combined organic layer was washed with brine, dried over magnesium sulfate and concentrated to give an oil. The product was purified by flash chromatography over silica gel eluting ethyl acetate:hexane (30:70) to give the N-protected methyl 3-amino-4-tetrahydrofurancarboxylate (3.30 g, 55%) as an oil MS (M+H)$^+$=280.

(9d) The N-protected methyl 3-amino-4-tetrahydrofurancarboxylate (9c)(3.30 g, 11.8 mmol) was taken up in methanol (50 mL) in a Parr shaker bottle. The reaction was degassed, 10% Pd/C (0.1 g) was added and charged to 60 psi hydrogen pressure. The reaction mixture was shaken for 1 h, filtered and concentrated to give the methyl 3-amino-4-tetrahydrofurancarboxylate (1.65 gm, 95%) as an oil MS (M+CH$_3$CN)$^+$=187.

(9e) Following the procedures analogous to that used for the preparation of example (1), but using methyl 3-amino-4-tetrahydrofurancarboxylate in step (1d) and procedures (2b–c) the title compound was prepared. The product was purified by reverse phase HPLC on a Vydac C-18 semiprep column eluting an acetonitrile:water:TFA gradient, to give the hydroxamic acid product (0.12 g, 65%) as a white amorphous solid. MS (M+H)$^+$=474.

Example 10

(βR)-3-amino-N-hydroxy-β-(2-methylpropyl)-3-[4-[(2-methyl-4-quinolinyl) methoxy]phenyl]-2-oxo-1-pyrrolidinepropanamide bis(trifluoroacetate) (salt)

(10a) Following the procedures analogous to that used for the preparation of example (9c,9d), but using mono t-butyl (D)-3-isopropylsuccinate in step (9c) and procedures (2b–c, 1f) the title compound was prepared. The product was purified by reverse phase HPLC on a Vydac C-18 semiprep column eluting an acetonitrile:water:TFA gradient, to give the hydroxamic acid product (0.05 g, 35%) as a white amorphous solid. MS (M+H)$^+$=491.

Example 11

(βR)-3-amino-β-(2-methylpropyl)-3-[4-[(2-methyl-4-quinolinyl) methoxy]phenyl]-2-oxo-1-pyrrolidinepropanoic acid bis(trifluoroacetate) (salt)

(11a) Following the procedures analogous to that used for the preparation of example (9c,9d), but using mono t-butyl (D)-3-isopropylsuccinate in step (9c) and procedures (2b–c)

the title compound was prepared. The product was purified by reverse phase HPLC on a Vydac C-18 semiprep column eluting an acetonitrile:water:TFA gradient, to give the carboxylic acid product (0.05 g, 35%) as a white amorphous solid. MS (M+H)$^+$=476.

Example 12

3-amino-N-hydroxy-α,α-dimethyl-3-[4-[(2-methyl-4-quinolinyl) methoxy]phenyl]-2-oxo-1-pyrrolidinepropanamide bis(trifluoroacetate) (salt)

(12a) Following the procedures analogous to that used for the preparation of example (9c,9d), but using methyl 3-amino-2,2-dimethylpropanoate in step (9c) and procedures (2b–c, 1f) the title compound was prepared. The product was purified by reverse phase HPLC on a Vydac C-18 semiprep column eluting an acetonitrile:water:TFA gradient, to give the hydroxamic acid product (0.03 g, 30%) as a white amorphous solid. MS (M+H)$^+$=463.

TABLE 1

$E = —CR^3R^{3a}CR^{3b}R^{3c}—$

| Ex | A' | E | R$^2$ | MS (M + H)$^+$ |
|---|---|---|---|---|
| 1 | NHOH | cyclohexyl (trans) | NH$_2$ | 489 |
| 2 | NHOH | cyclohexyl (cis) | NH$_2$ | 489 |
| 3 | OH | cyclohexyl (cis) | NH$_2$ | 474 |
| 4 | OH | cyclopentyl | NH$_2$ | 460 |
| 5 | NHOH | cyclopentyl | NH$_2$ | 475 |
| 6 | NHOH | dimethylcyclopentyl | NH$_2$ | 475 |
| 7 | NHOH | trimethylcyclopentyl | NH$_2$ | 503 |
| 8 | NHOH | indanyl | NH$_2$ | 523 |
| 9 | NHOH | tetrahydrofuranyl | NH$_2$ | 474 |
| 10 | NHOH | 2,4-dimethylpentyl | NH$_2$ | 491 |
| 11 | OH | 2,4-dimethylpentyl | NH$_2$ | 476 |
| 12 | NHOH | tert-butyl-ethyl | NH$_2$ | 463 |

The following tables contain representative examples of present invention. Each entry in each table is intended be paired with each formula at the start of the table. For example, in Table 2, example 1 is intended to be paired with each of formulae A1-HHH3.

TABLE 2
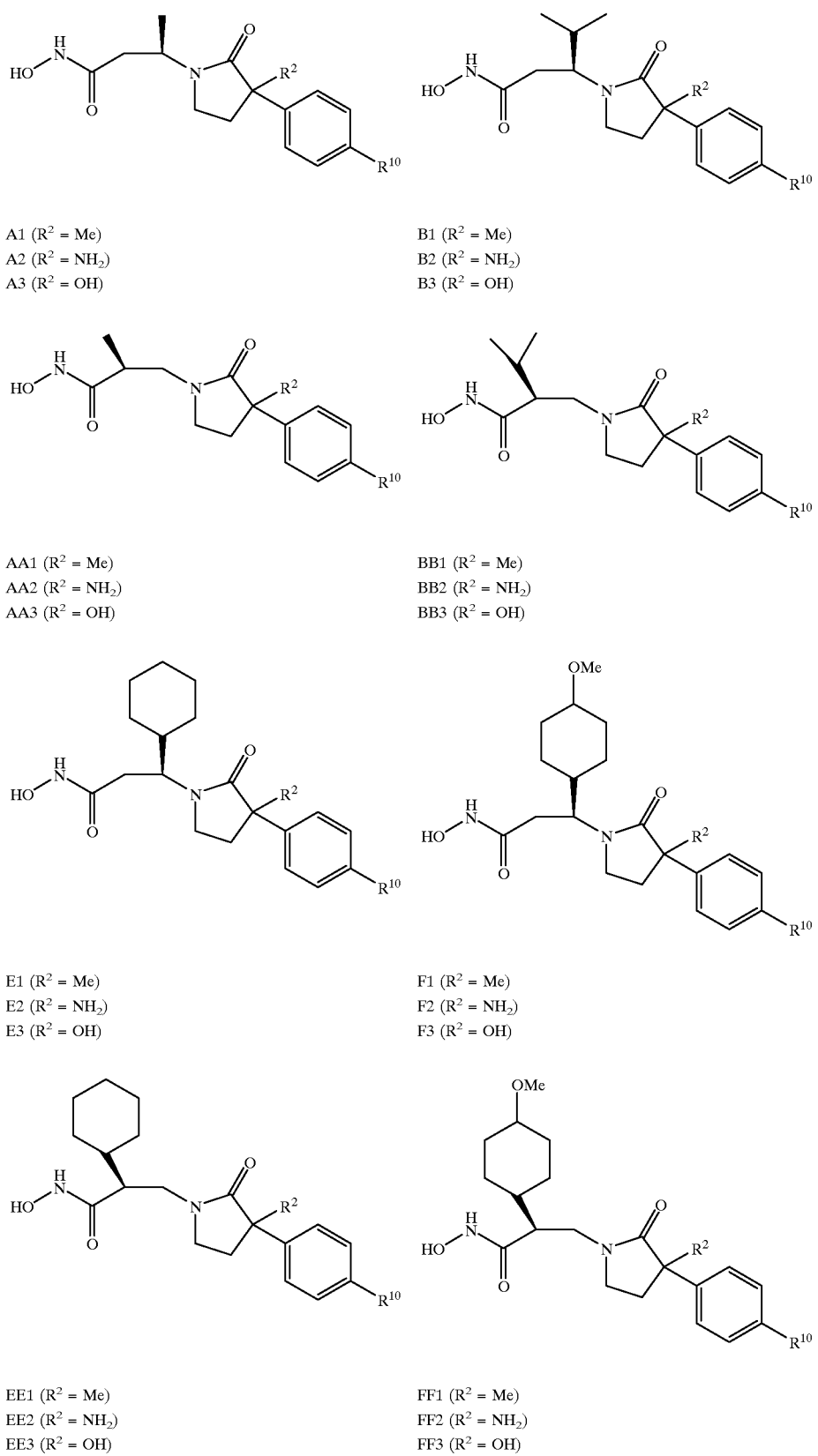
A1 (R² = Me)
A2 (R² = NH₂)
A3 (R² = OH)
B1 (R² = Me)
B2 (R² = NH₂)
B3 (R² = OH)
AA1 (R² = Me)
AA2 (R² = NH₂)
AA3 (R² = OH)
BB1 (R² = Me)
BB2 (R² = NH₂)
BB3 (R² = OH)
E1 (R² = Me)
E2 (R² = NH₂)
E3 (R² = OH)
F1 (R² = Me)
F2 (R² = NH₂)
F3 (R² = OH)
EE1 (R² = Me)
EE2 (R² = NH₂)
EE3 (R² = OH)
FF1 (R² = Me)
FF2 (R² = NH₂)
FF3 (R² = OH)

TABLE 2-continued
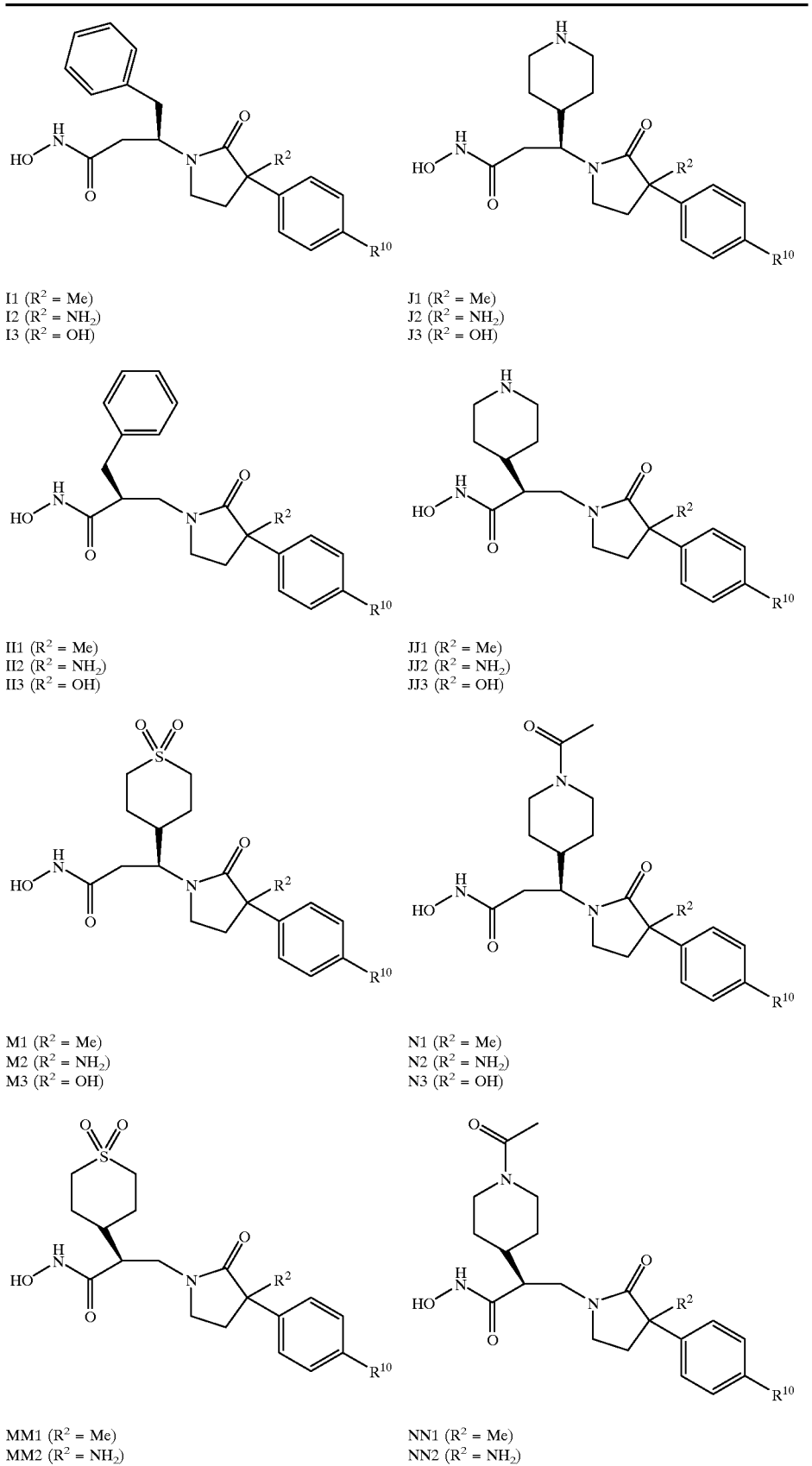
I1 ($R^2$ = Me)
I2 ($R^2$ = $NH_2$)
I3 ($R^2$ = OH)
J1 ($R^2$ = Me)
J2 ($R^2$ = $NH_2$)
J3 ($R^2$ = OH)
II1 ($R^2$ = Me)
II2 ($R^2$ = $NH_2$)
II3 ($R^2$ = OH)
JJ1 ($R^2$ = Me)
JJ2 ($R^2$ = $NH_2$)
JJ3 ($R^2$ = OH)
M1 ($R^2$ = Me)
M2 ($R^2$ = $NH_2$)
M3 ($R^2$ = OH)
N1 ($R^2$ = Me)
N2 ($R^2$ = $NH_2$)
N3 ($R^2$ = OH)
MM1 ($R^2$ = Me)
MM2 ($R^2$ = $NH_2$)
NN1 ($R^2$ = Me)
NN2 ($R^2$ = $NH_2$)

TABLE 2-continued
MM3 ($R^2$ = OH)  NN3 ($R^2$ = OH)
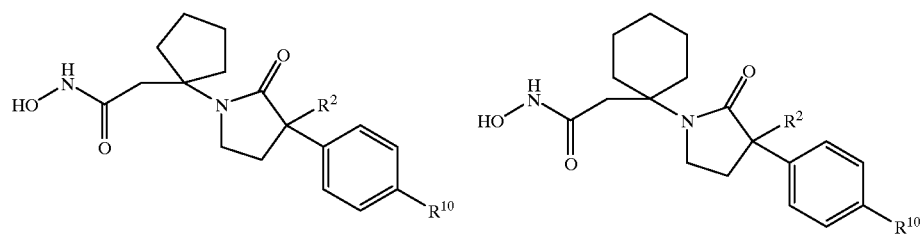
Q1 ($R^2$ = Me)  R1 ($R^2$ = Me)
Q2 ($R^2$ = $NH_2$)  R2 ($R^2$ = $NH_2$)
Q3 ($R^2$ = OH)  R3 ($R^2$ = OH)
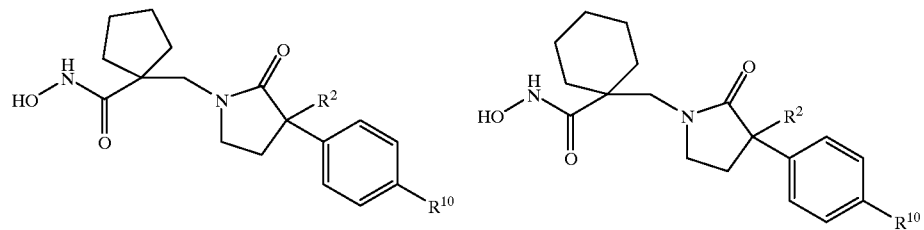
QQ1 ($R^2$ = Me)  RR1 ($R^2$ = Me)
QQ2 ($R^2$ = $NH_2$)  RR2 ($R^2$ = $NH_2$)
QQ3 ($R^2$ = OH)  RR3 ($R^2$ = OH)
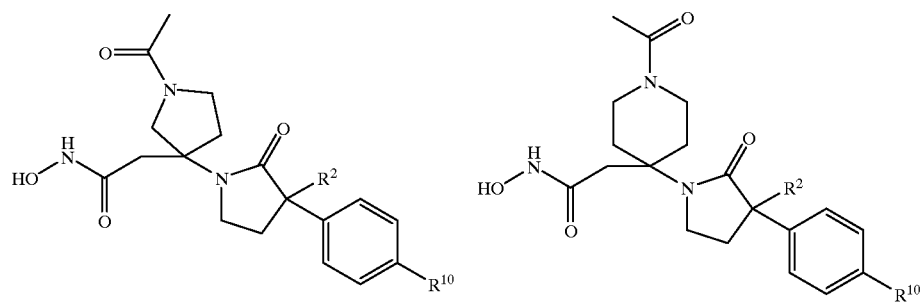
U1 ($R^2$ = Me)  V1 ($R^2$ = Me)
U2 ($R^2$ = $NH_2$)  V2 ($R^2$ = $NH_2$)
U3 ($R^2$ = OH)  V3 ($R^2$ = OH)
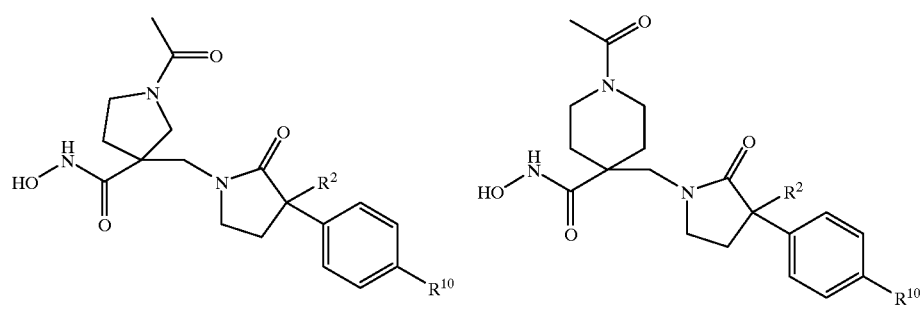
UU1 ($R^2$ = Me)  VV1 ($R^2$ = Me)
UU2 ($R^2$ = $NH_2$)  VV2 ($R^2$ = $NH_2$)
UU3 ($R^2$ = OH)  VV3 ($R^2$ = OH)

TABLE 2-continued
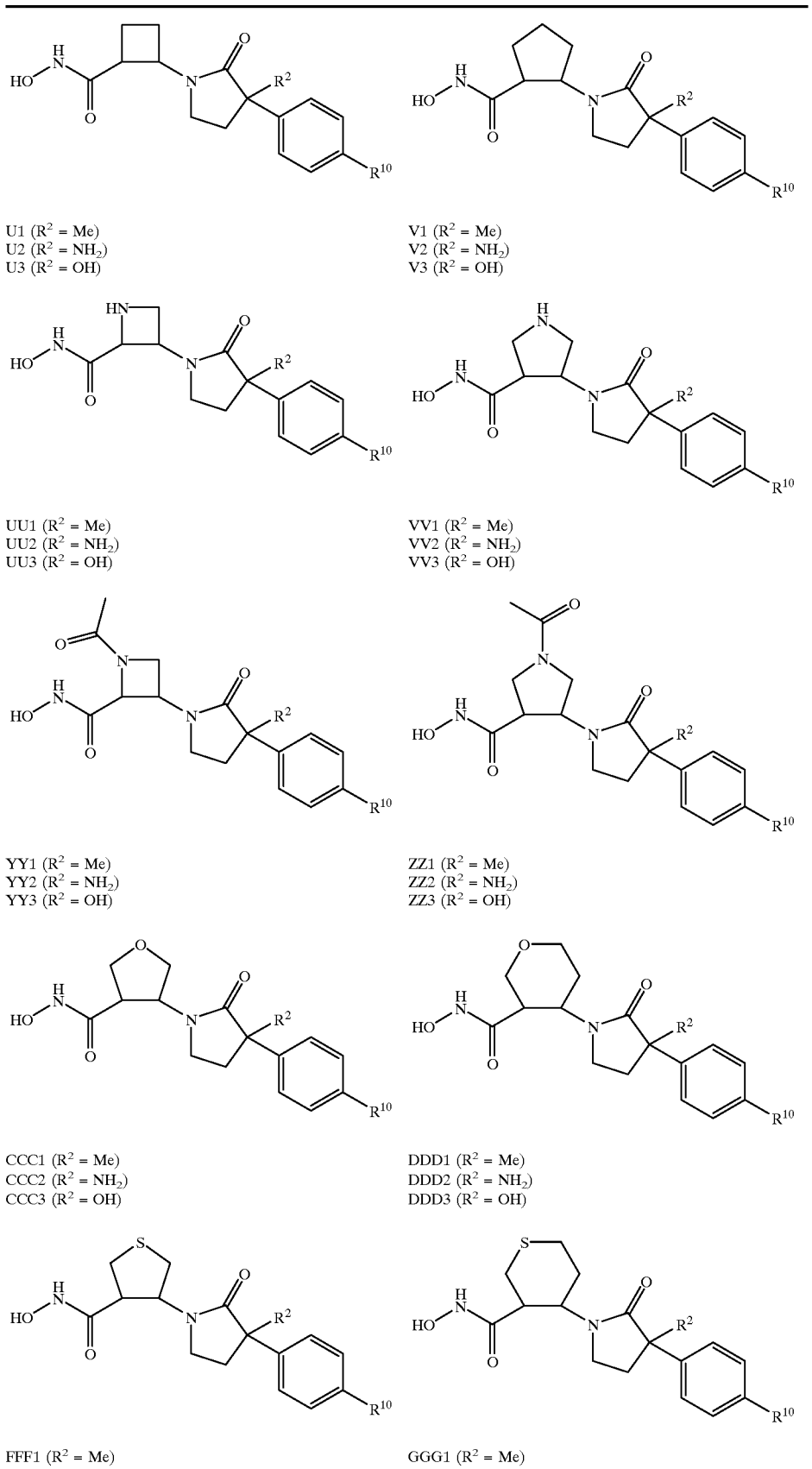
U1 (R² = Me)
U2 (R² = NH₂)
U3 (R² = OH)
V1 (R² = Me)
V2 (R² = NH₂)
V3 (R² = OH)
UU1 (R² = Me)
UU2 (R² = NH₂)
UU3 (R² = OH)
VV1 (R² = Me)
VV2 (R² = NH₂)
VV3 (R² = OH)
YY1 (R² = Me)
YY2 (R² = NH₂)
YY3 (R² = OH)
ZZ1 (R² = Me)
ZZ2 (R² = NH₂)
ZZ3 (R² = OH)
CCC1 (R² = Me)
CCC2 (R² = NH₂)
CCC3 (R² = OH)
DDD1 (R² = Me)
DDD2 (R² = NH₂)
DDD3 (R² = OH)
FFF1 (R² = Me)
GGG1 (R² = Me)

TABLE 2-continued
| | |
|---|---|
| FFF2 (R² = NH₂) | GGG2 (R² = NH₂) |
| FFF3 (R² = OH) | GGG3 (R² = OH) |
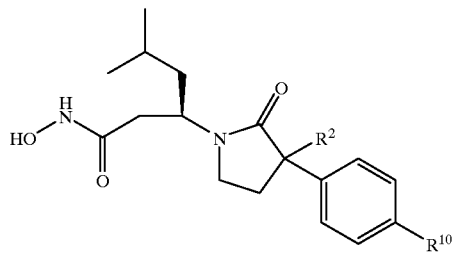
C1 (R² = Me)
C2 (R² = NH₂)
C3 (R² = OH)
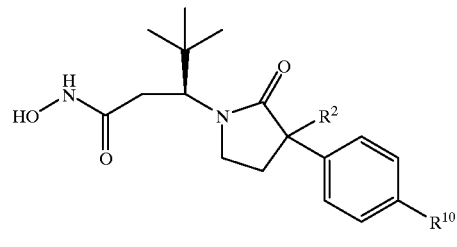
D1 (R² = Me)
D2 (R² = NH₂)
D3 (R² = OH)
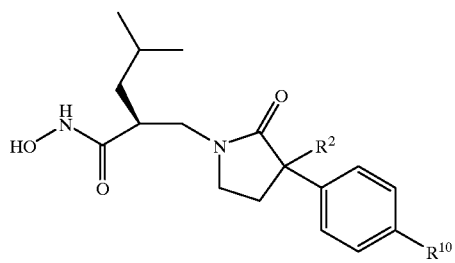
CC1 (R² = Me)
CC2 (R² = NH₂)
CC3 (R² = OH)
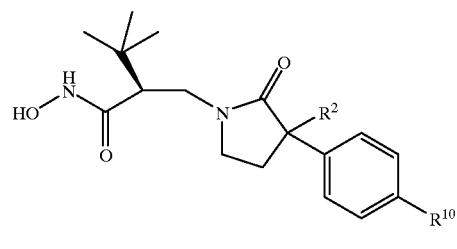
DD1 (R² = Me)
DD2 (R² = NH₂)
DD3 (R² = OH)
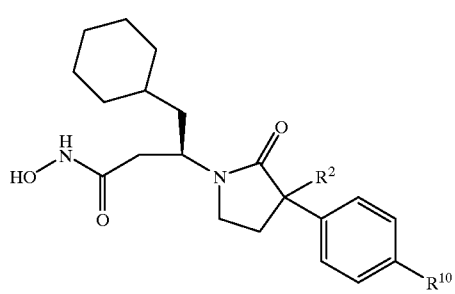
G1 (R² = Me)
G2 (R² = NH₂)
G3 (R² = OH)
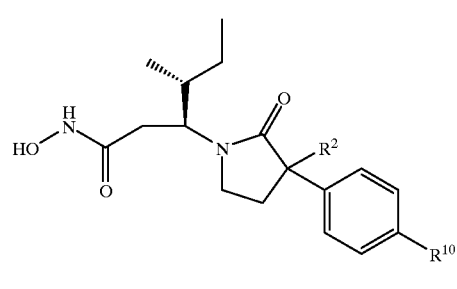
H1 (R² = Me)
H2 (R² = NH₂)
H3 (R² = OH)
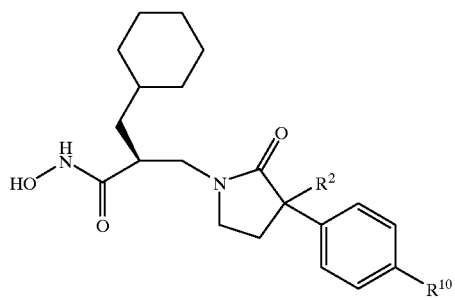
GG1 (R² = Me)
GG2 (R² = NH₂)
GG3 (R² = OH)
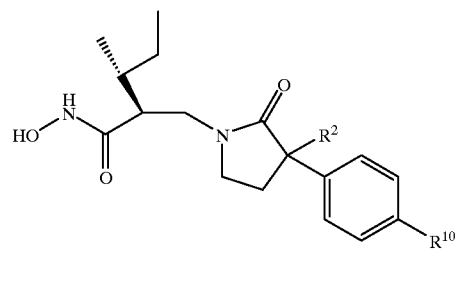
HH1 (R² = Me)
HH2 (R² = NH₂)
HH3 (R² = OH)

TABLE 2-continued
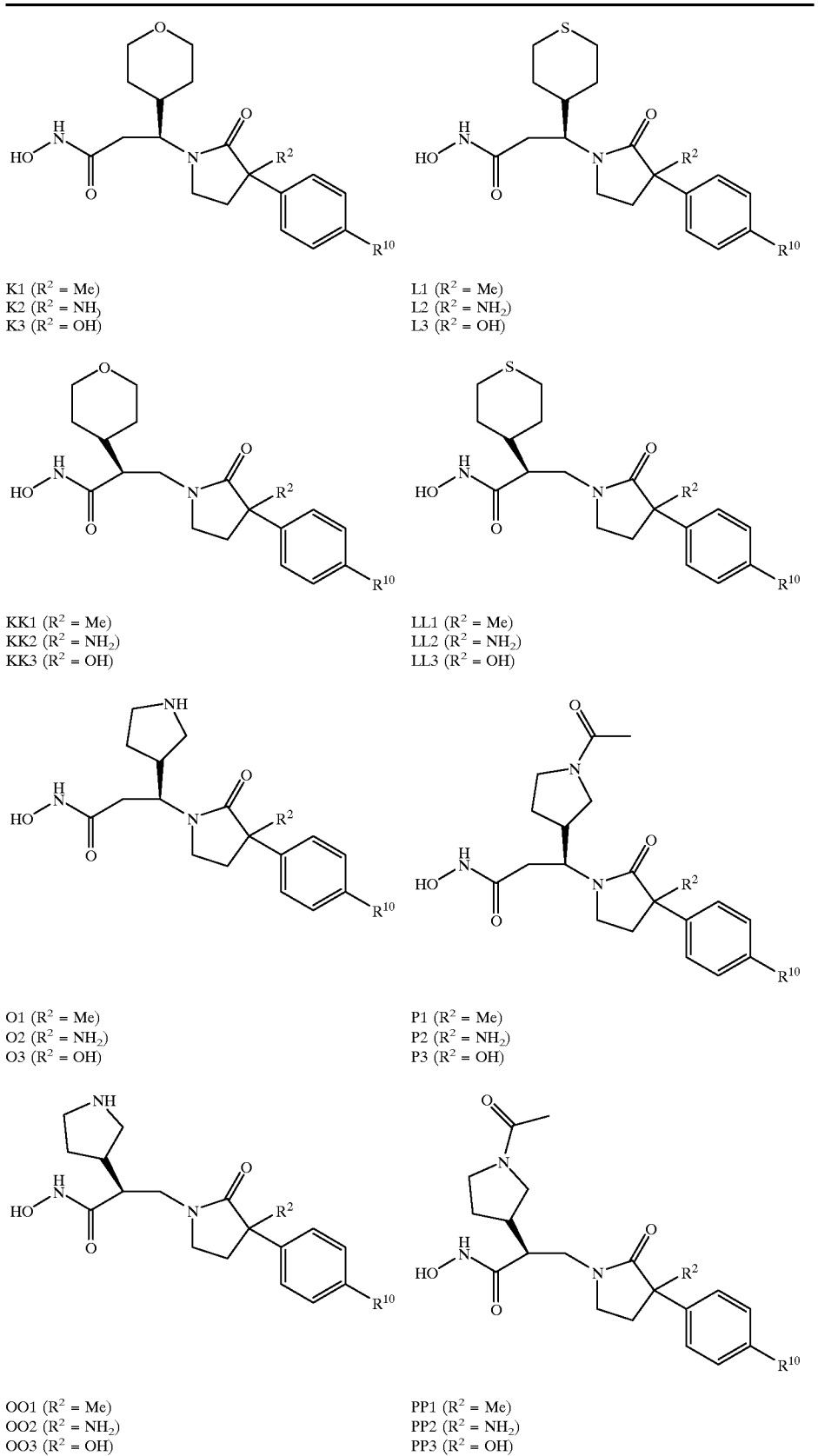
K1 (R² = Me)  
K2 (R² = NH₂)  
K3 (R² = OH)
L1 (R² = Me)  
L2 (R² = NH₂)  
L3 (R² = OH)
KK1 (R² = Me)  
KK2 (R² = NH₂)  
KK3 (R² = OH)
LL1 (R² = Me)  
LL2 (R² = NH₂)  
LL3 (R² = OH)
O1 (R² = Me)  
O2 (R² = NH₂)  
O3 (R² = OH)
P1 (R² = Me)  
P2 (R² = NH₂)  
P3 (R² = OH)
OO1 (R² = Me)  
OO2 (R² = NH₂)  
OO3 (R² = OH)
PP1 (R² = Me)  
PP2 (R² = NH₂)  
PP3 (R² = OH)

TABLE 2-continued
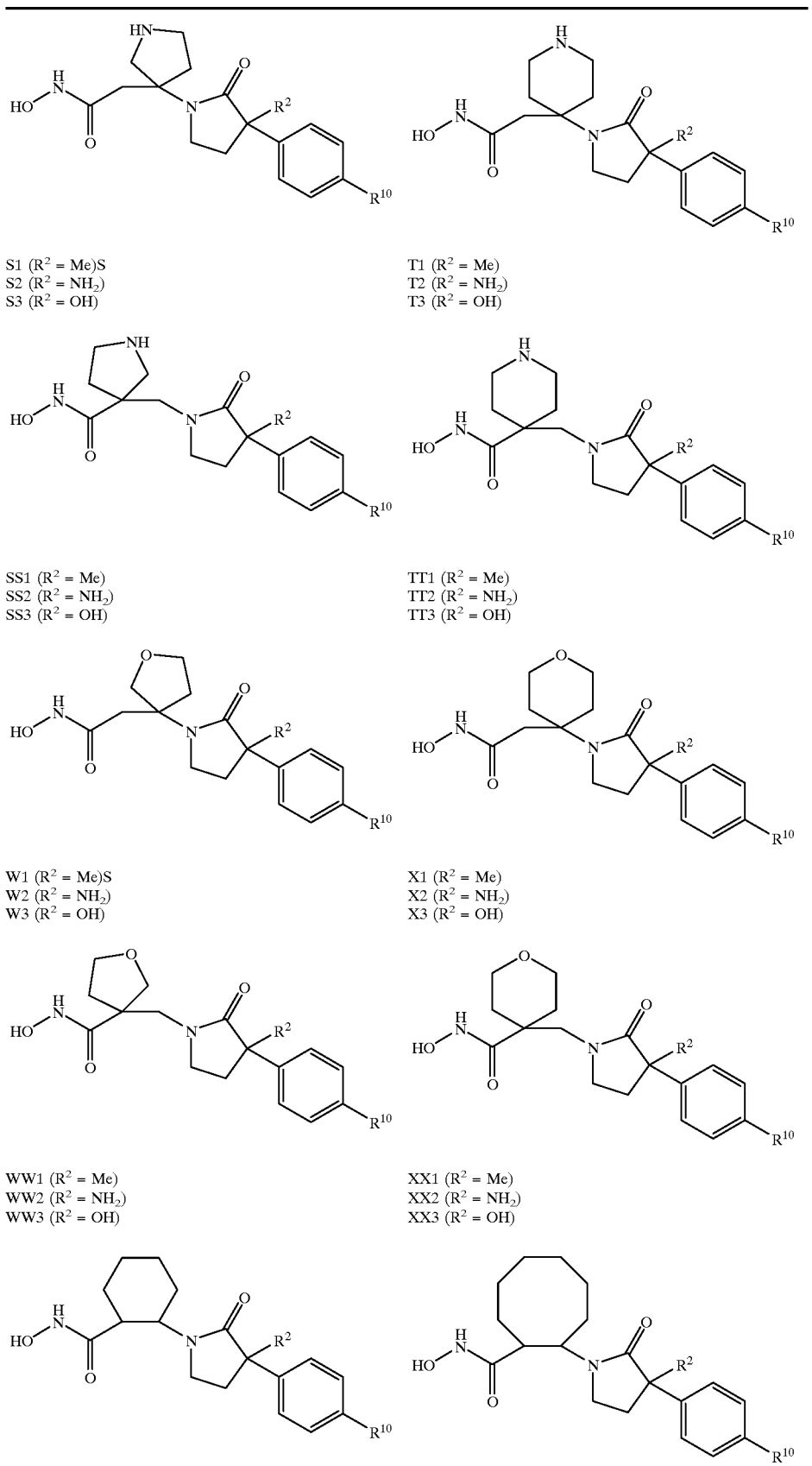
S1 (R² = Me)S
S2 (R² = NH₂)
S3 (R² = OH)
T1 (R² = Me)
T2 (R² = NH₂)
T3 (R² = OH)
SS1 (R² = Me)
SS2 (R² = NH₂)
SS3 (R² = OH)
TT1 (R² = Me)
TT2 (R² = NH₂)
TT3 (R² = OH)
W1 (R² = Me)S
W2 (R² = NH₂)
W3 (R² = OH)
X1 (R² = Me)
X2 (R² = NH₂)
X3 (R² = OH)
WW1 (R² = Me)
WW2 (R² = NH₂)
WW3 (R² = OH)
XX1 (R² = Me)
XX2 (R² = NH₂)
XX3 (R² = OH)

TABLE 2-continued
W1 (R² = Me)S
W2 (R² = NH₂)
W3 (R² = OH)
X1 (R² = Me)
X2 (R² = NH₂)
X3 (R² = OH)
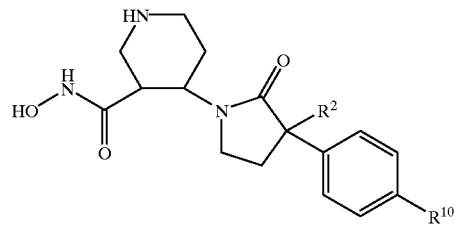
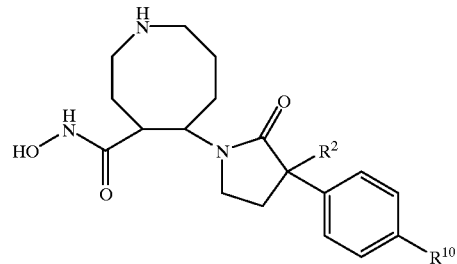
WW1 (R² = Me)
WW2 (R² = NH₂)
WW3 (R² = OH)
XX1 (R² = Me)
XX2 (R² = NH₂)
XX3 (R² = OH)
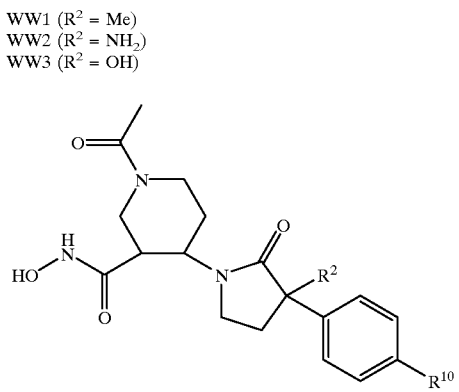
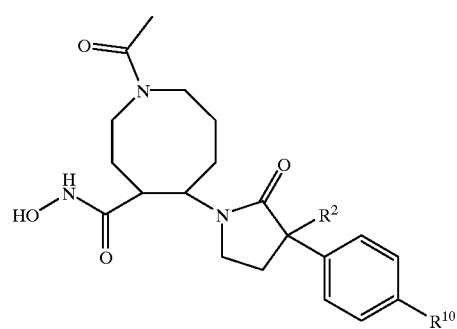
AAA1 (R² = Me)
AAA2 (R² = NH₂)
AAA3 (R² = OH)
BBB1 (R² = Me)
BBB2 (R² = NH₂)
BBB3 (R² = OH)
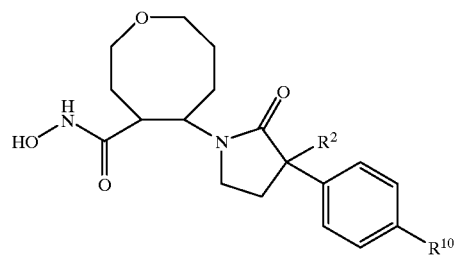
EEE1 (R² = Me)
EEE2 (R² = NH₂)
EEE3 (R² = OH)
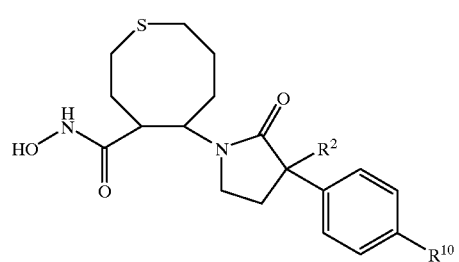
HHH1 (R² = Me)
HHH2 (R² = NH₂)
HHH3 (R² = OH)

| Ex# | R¹⁰ |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)methoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |
| 90 | (4,5-dimethyl-2-furanyl)methoxy |
| 91 | (4,5-dimethyl-2-thiazolyl)methoxy |
| 92 | 2-(2-oxazolyl)ethyl |

Utility

The compounds of formula I are expected to possess metalloproteinase and/or aggrecanase and/or TNF-α inhibitory activity. The MP inhibitory activity of the compounds of the present invention is demonstrated using assays of MP activity, for example, using the assay described below for assaying inhibitors of MP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, *Cancer and Metastasis Reviews* 1990, 9, 289–303). The compounds of the present invention should be useful for the prevention and treatment of invasive tumors by inhibition of this aspect of metastasis.

The compounds of the present invention should also have utility for the prevention and treatment of osteopenia associated with matrix metalloproteinase-mediated breakdown of cartilage and bone that occurs in osteoporosis patients.

Compounds that inhibit the production or action of TNF and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholism, anorexia, asthma, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride-stimulated mice, for example, using the assay for TNF Induction in Mice and in human whole blood as described below.

Some compounds of the present invention have been shown to inhibit aggrecanase, a key enzyme in cartilage breakdown, as determined by the aggrecanase assay described below.

As used herein "$\mu g$" denotes microgram, "mg" denotes milligram, "g" denotes gram, "$\mu L$" denotes microliter, "mL" denotes milliliter, "L" denotes liter, "nM" denotes nanomolar, "$\mu M$" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 $\mu M$ for the inhibition of a desired MP. Preferred compounds of the present invention have $K_i$'s or $IC_{50}$'s of $\leq 1$ $\mu M$. More preferred compounds of the present invention have $K_i$'s or $IC_{50}$'s of $\leq 0.1$ $\mu M$. Even more preferred compounds of the present invention have $K_i$'s or $IC_{50}$'s of $\leq 0.01$ $\mu M$. Still more preferred compounds of the present invention have $K_i$'s or $IC_{50}$'s of $\leq 0.001$ $\mu M$.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanase, time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNFα) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et. al. Trans. Ortho. Res. Soc. 20, 341, 1995). Therefore, in order to accumulate BNC aggrecanase in culture media, cartilage is first depleted of endogenous aggrecan by stimulation with 500 ng/mL human recombinant IL-β for 6 days with media changes every 2 days. Cartilage is then stimulated for an additional 8 days without media change to allow accumulation of soluble, active aggrecanase in the culture media. In order to decrease the amounts of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, CE, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/–0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/mL aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

PBMC Assay

Human peripheral blood mononuclear cells (PBMC) were obtained from normal donor blood by leukophoresis and isolated by Ficoll-Paque density separation. PBMCs were suspended in 0.5 mL RPMI 1640 with no serum at $2\times10^6$ cells/mL in 96 well polystyrene plates. Cells were pre incubated 10 minutes with compound, then stimulated with 1 $\mu g/mL$ LPS (Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 $\mu$M. The final concentration of DMSO does not exceed 0.5%. Compounds are preincubated for 15 minutes before the addition of 100 ng/mL LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction In Mice

Test compounds are administered to mice either I.P. or P.O. at time zero. Immediately following compound administration, mice receive an I.P. injection of 20 mg of D-galactosamine plus 10 $\mu$g of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Counterscreens

The enzymatic activities of recombinant MP-1, 2, 3, 9 and 13 were measured at 25° C. with a fluorometric assay (Copeland, R. A.; Lombardo, D.; Giannaras, J. and Decicco, C. P. *Bioorganic Med. Chem. Lett.* 1995, 5 , 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis,* Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values as previously described.

Compounds tested in the above assay are considered to be active if they exhibit a $K_i$ of $\leq$10 $\mu$M. Preferred compounds of the present invention have $K_i$'s of $\leq$1 $\mu$M. More preferred compounds of the present invention have $K_i$'s of $\leq$0.1 $\mu$M. Even more preferred compounds of the present invention have $K_i$'s of $\leq$0.01 $\mu$M. Still more preferred compounds of the present invention have $K_i$'s of $\leq$0.001 $\mu$M.

Using the methodology described above, a number of compounds of the present invention were found to exhibit $K_i$'s of $\leq$10 $\mu$M, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action, MP-3, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

By way of general guidance, the daily oral dosage of aeach active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformLy mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

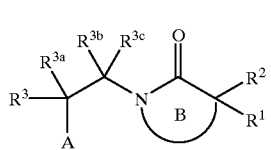

or a stereoisomer or pharmaceutically acceptable salt form thereof, wherein;

A is selected from $COR^5$, $-CO_2H$, $CH_2CO_2H$, $-CO_2R^6$, $-CONHOH$, $-CH_2CONHOH$, $-CONHOR^5$, $-CONHOR^6$, $-NHR^a$, $-N(OH)COR^5$, $-SH$, $-CH_2SH$, $-SO_2NHR^a$, $S(=NH)_2R^a$, $PO(OH)_2$, and $PO(OH)NHR^a$;

ring B is a pyrrolidinone;

$R^1$ is $U-X-Y-Z-U^a-X^a-Y^a-Z^a$;

U is absent;

X is absent;

Y is absent;

Z is selected from a $C_{3-13}$ carbocycle substituted with 0–5 $R^b$ and a 5–14 membered heterocycle comprising carbon atoms and from 1–4 heteroatoms selected from the group consisting of N, O, and S and substituted with 0–5 $R^b$;

$U^a$ is absent or is selected from: O, $NR^a$, $C(O)$, $C(O)O$, $OC(O)$, $C(O)NR^a$, $NR^aC(O)$, $OC(O)O$, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from $C_{1-10}$ alkylene, $C_{2-10}$ alkenylene, $C_{2-10}$ alkynylene;

$Y^a$ is absent or selected from O, $NR^a$, $S(O)_p$, and $C(O)$;

$Z^a$ is selected from H, a $C_{3-13}$ carbocycle substituted with 0–5 $R^c$ and a 5–14 membered heterocycle comprising carbon atoms and from 1–4 heteroatoms selected from the group consisting of N, O, and S and substituted with 0–5 $R^c$;

$R^2$ is selected from Q, $C_{1-10}$ alkylene-Q, $C_{2-10}$ alkenylene-Q, $C_{2-10}$ alkynylene-Q, $(CRR')_rO(CRR')_r-Q$, $(CRR')_rNR^a(CRR')_r-Q$, $(CRR')_r-Q$, $(CRR')_rNR^aC(O)(CRR')_r-Q$, $(CRR')_rC(O)NR^a(CRR')_r-Q$, $(CRR')_rC(O)(CRR')_r-Q$, $(CRR')_rC(O)O(CRR')_r-Q$, $(CRR')_rS(O)_p(CRR')_r-Q$, $(CRR')_rSO_2NR^a(CRR')_r-Q$, $(CRR')_rNR^aC(O)NR^a(CRR')_r-Q$, $(CRR')_rOC(O)NR^a(CRR')_r-Q$, and $(CRR')_rNR^aC(O)O(CRR')_r-Q$;

R, at each occurrence, is independently selected from H, $CH_3$, $CH_2CH_3$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

alternatively, $R^1$ and $R^2$ combine to form a $C_{3-13}$ carbocycle substituted with $R^{1'}$ and 0–3 $R^b$ or a 5–14 membered heterocycle comprising carbon atoms and from 1–4 heteroatoms selected from the group consisting of N, O, and S and substituted with $R^{1'}$ and 0–3 $R^b$;

Q is selected from H, a $C_{3-13}$ carbocycle substituted with 0–5 $R^b$ and a 5–14 membered heterocycle comprising carbon atoms and from 1–4 heteroatoms selected from the group consisting of N, O, and S and substituted with 0–5 $R^b$;

$R^{1'}$ is $U^a-X^a-Y^a-Z^a$;

$R^{3a}$ is selected from H, $C_{1-6}$ alkyl, phenyl, and benzyl;

R³ᶜ is selected from H, C₁₋₆ alkyl, phenyl, and benzyl;
alternatively one of R³ᵃ and R³ᶜ maybe independently selected from (CRR')ᵣORᵃ, (CRR')ᵣNRᵃRᵃ', (CRR')ᵣC(O)Rᵃ, (CRR')ᵣC(O)ORᵃ, (CRR')ᵣC(O)NRᵃRᵃ', (CRR')ᵣS(O)ₚRᵃ, and (CRR')ᵣS(O)ₚNRᵃRᵃ', provided that in the group (CRR')ᵣS(O)ₚRᵃ, Rᵃ is other than H;
R³ and R³ᵇ together with the carbon atoms to which they are attached combine to form a 3–10 membered carbocyclic or heterocyclic ring comprising carbon atoms and 0–3 ring heteroatoms selected from O, N, NRᵃ, and S(O)ₚ and substituted with 0–2 Rᵈ, provided that the cyclic moiety contains other than an N—S, O—S, O—O, or S—S bond;
Rᵃ, at each occurrence, is independently selected from H, C₁₋₄ alkyl, phenyl and benzyl;
Rᵃ', at each occurrence, is independently selected from H, C₁₋₄ alkyl, phenyl and benzyl;
Rᵃ", at each occurrence, is independently selected from H, C₁₋₄ alkyl, benzyl, C₃₋₇ carbocyclic group, or a 5–6 membered heteroaromatic ring containing 1–4 heteroatoms selected from the group consisting of N, O, and S;
alternatively, Rᵃ and Rᵃ' taken together with the nitrogen to which they are attached form a 5 or 6 membered ring comprising 0–1 additional heteroatoms selected from the group consisting of N, O, and S;
Rᵇ, at each occurrence, is independently selected from C₁₋₆ alkyl, ORᵃ, Cl, F, Br, I, =O, CN, NO₂, NRᵃRᵃ', C(O)Rᵃ", C(O)ORᵃ, C(O)NRᵃRᵃ', S(O)₂NRᵃRᵃ', S(O)ₚRᵃ, CF₃, and CF₂CF₃;
Rᶜ, at each occurrence, is independently selected from C₁₋₆ alkyl, ORᵃ, Cl, F, Br, I, =O, CN, NO₂, NRᵃRᵃ', C(O)Rᵃ, C(O)ORᵃ, C(O)NRᵃRᵃ', NRᵃC(O)NRᵃRᵃ', S(O)₂NRᵃRᵃ', S(O)ₚRᵃ, CF₃, CF₂CF₃, —CH(=NOH), —C(=NOH)CH₃, (CRR')ₛO(CRR')ₛRᵈ, (CRR')ₛS(O)ₚ(CRR')ₛRᵈ, (CRR')ₛNRᵃ(CRR')ₛRᵈ, phenyl, and a 5–14 membered heterocyclic group comprising 1–4 heteroatoms selected from the group consisting of N, O, and S;
Rᵈ, at each occurrence, is independently selected from C₁₋₆ alkyl, ORᵃ, Cl, F, Br, I, =O, CN, NO₂, NRᵃRᵃ', C(O)Rᵃ, C(O)ORᵃ, C(O)NRᵃRᵃ', NRᵃC(O)NRᵃRᵃ', S(O)₂NRᵃRᵃ', S(O)ₚRᵃ, CF₃, CF₂CF₃, phenyl, and a 5–6 membered heterocyclic group comprising 1–4 heteroatoms selected from the group consisting of N, O, and S;
alternatively, when two Rᵈs are attached to adjacent atoms on R³, R³ᵃ, R³ᵇ, or R³ᶜ, they combine to form a 5–6 membered carbocyclic ring or a 5–6 membered heterocyclic ring comprising 1–4 heteroatoms selected from the group consisting of NRᵃ, O, and S;
R⁵, at each occurrence, is selected from C₁₋₁₀ alkyl substituted with 0–2 Rᵇ, and C₁₋₈ alkyl substituted with 0–2 Rᵉ;
Rᵉ, at each occurrence, is independently selected from phenyl substituted with 0–3 Rᵇ, biphenyl substituted with 0–2 Rᵇ, naphthyl substituted with 0–3 Rᵇ and a 5–10 membered heteroaryl system comprising 1–4 heteroatoms selected from the group consisting of N, O, and S and substituted with 0–3 Rᵇ;
R⁶, at each occurrence, is selected from phenyl, naphthyl, C₁₋₁₀ alkyl-phenyl-C₁₋₆ alkyl-, C₃₋₁₁ cycloalkyl, C₁₋₆ alkylcarbonyloxy-C₁₋₃ alkyl-, C₁₋₆ alkoxycarbonyloxy-C₁₋₃ alkyl-, C₂₋₁₀ alkoxycarbonyl, C₃₋₆ cycloalkylcarbonyloxy-C₁₋₃ alkyl-, C₃₋₆ cycloalkoxycarbonyloxy-C₁₋₃ alkyl-, C₃₋₆ cycloalkoxycarbonyl, phenoxycarbonyl, phenyloxycarbonyloxy-C₁₋₃ alkyl-, phenylcarbonyloxy-C₁₋₃ alkyl-, C₁₋₆ alkoxy-C₁₋₆ alkylcarbonyloxy-C₁₋₃ alkyl-, [5-(C₁₋₅ alkyl)-1,3-dioxa-cyclopenten-2-one-yl]methyl, (5-aryl-1,3-dioxa-cyclopenten-2-one-yl)methyl, —C₁₋₁₀ alkyl-NR⁷R⁷ᵃ, —CH(R⁸)OC(=O)R⁹, —CH(R⁸)OC(=O)OR⁹, and

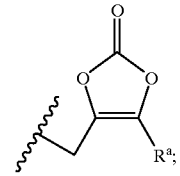

R⁷ is selected from H and C₁₋₁₀ alkyl, C₂₋₆ alkenyl, C₃₋₆ cycloalkyl-C₁₋₃ alkyl-, and phenyl-C₁₋₆ alkyl-;
R⁷ᵃ is selected from H and C₁₋₁₀ alkyl, C₂₋₆ alkenyl, C₃₋₆ cycloalkyl-C₁₋₃ alkyl-, and phenyl-C₁₋₆ alkyl-;
R⁸ is selected from H and C₁₋₄ linear alkyl;
R⁹ is selected from H, C₁₋₈ alkyl substituted with 1–2 Rᵉ, C₃₋₈ cycloalkyl substituted with 1–2 Rᵉ, and phenyl substituted with 0–2 Rᵇ;
Rᵉ, at each occurrence, is selected from C₁₋₄ alkyl, C₃₋₈ cycloalkyl, C₁₋₅ alkoxy, phenyl substituted with 0–2 Rᵇ;
p, at each occurrence, is selected from 0, 1, and 2;
r, at each occurrence, is selected from 0, 1, 2, 3, 4, and 5;
r', at each occurrence, is selected from 0, 1, 2, 3, 4, and 5;
s, at each occurrence, is selected from 0, 1, 2, and 3; and,
s', at each occurrence, is selected from 0, 1, 2, and 3.
2. A compound according to claim 1, wherein:
A is selected from —CO₂H, CH₂CO₂H, —CONHOH, —CONHOR⁵, —CONHOR⁶, —N(OH)COR⁵, —SH, and —CH₂SH;
R¹ is U—X—Y—Z—Uᵃ—Xᵃ—Yᵃ—Zᵃ;
Z is selected from a C₃₋₁₀ carbocycle substituted with 0–5 Rᵇ and a 5–10 membered heterocycle comprising carbon atoms and from 1–4 hetero atoms selected from the group consisting of N, O, and S and substituted with 0–5 Rᵇ;
Uᵃ is absent or is selected from: O, NRᵃ, C(O), C(O)O, OC(O), C(O)NRᵃ, NRᵃC(O), S(O)ₚ, and S(O)ₚNRᵃ;
Xᵃ is absent or selected from C₁₋₆ alkylene, C₂₋₆ alkenylene, C₂₋₆ alkynylene;
Yᵃ is absent or selected from O, NRᵃ, and C(O);
Zᵃ is selected from a C₅₋₁₀ carbocycle substituted with 0–5 Rᶜ and a 5–10 membered heterocycle comprising carbon atoms and from 1–4 heteroatoms selected from the group consisting of N, O, and S and substituted with 0–5 Rᶜ;
R² is selected from Q, C₁₋₆ alkylene-Q, C₂₋₆ alkenylene-Q, C₂₋₆ alkynylene-Q, (CRR')ᵣO(CRR')ᵣ—Q, (CRR')ᵣNRᵃ(CRR')ᵣ—Q, (CRR')ᵣNRᵃC(O)(CRR')ᵣ—Q, (CRR')ᵣC(O)NRᵃ(CRR')ᵣ—Q, (CRR')ᵣC(O)(CRR')ᵣ—Q, (CRR')ᵣC(O)O(CRR')ᵣ—Q, (CRR')ᵣS(O)ₚ(CRR')ᵣ—Q, and (CRR')ᵣSO₂NRᵃ(CRR')ᵣ—Q;
R, at each occurrence, is independently selected from H, CH₃, CH₂CH₃, and CH=CH₂;
R', at each occurrence, is independently selected from H, CH₃, and CH₂CH₃;
alternatively, R¹ and R² combine to form a C₃₋₁₀ carbocycle substituted with R¹' and 0–3 Rᵇ or a 5–10 membered heterocycle comprising carbon atoms and from 1–4 heteroatoms selected from the group consisting of N, O, and S and substituted with $R^{1'}$ and 0–3 $R^b$;

Q is selected from H, a $C_{5-10}$ carbocycle substituted with 0–5 $R^b$ and a 5–10 membered heterocycle comprising carbon atoms and from 1–4 heteroatoms selected from the group consisting of N, O, and S and substituted with 0–5 $R^b$;

$R^{1'}$ is $U^a$—$X^a$—$Y^a$—$Z^a$;

$R^{3a}$ is selected from H, $C_{1-6}$ alkyl, phenyl, and benzyl;

$R^{3c}$ is selected from H, $C_{1-6}$ alkyl, phenyl, and benzyl;

alternatively one of $R^{3a}$ and $R^{3c}$ maybe independently selected from $(CRR')_rOR^a$, $(CRR')_rNR^aR^{a'}$, $(CRR')_rC(O)R^a$, $(CRR')_rC(O)OR^a$, $(CRR')_rC(O)NR^aR^{a'}$, $(CRR')_{r'}S(O)_pR^a$, and $(CRR')_rS(O)_pNR^aR^{a'}$, provided that in the group $(CRR')_rS(O)_pR^a$, $R^a$ is other than H;

$R^3$ and $R^{3b}$ together with the carbon atoms to which they are attached combine to form a 4–10 membered carbocyclic or heterocyclic ring comprising carbon atoms and 0–3 ring heteroatoms selected from O, N, $NR^a$, and $S(O)_p$ and substituted with 0–2 $R^d$, provided that the cyclic moiety contains other than an N—S, O—S, O—O, or S—S bond;

$R^b$, at each occurrence, is independently selected from $C_{1-6}$ alkyl, $OR^a$, Cl, F, Br, I, =O, CN, $NO_2$, $NR^aR^{a'}$, $C(O)R^{a'}$, $C(O)OR^a$, $C(O)NR^aR^{a'}$, $S(O)_2NR^aR^{a'}$, $S(O)_p R^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, —CH(=NOH), —C(=NOH)CH_3, $(CRR')_sO(CRR')_sR^d$, $(CRR')_sS(O)_p(CRR')_sR^d$, $(CRR')_sNR^a(CRR')_sR^d$, phenyl, and a 5–10 membered heterocyclic group comprising 1–4 heteroatoms selected from the group consisting of N, O, and S;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, phenyl, and a 5–6 membered heterocyclic group comprising 1–4 heteroatoms selected from the group consisting of N, O, and S;

alternatively, when two $R^d$s are attached to adjacent atoms on $R^3$, $R^{3a}$, $R^{3b}$, or $R^{3c}$, they combine to form a 5–6 membered carbocyclic ring or a 5–6 membered heterocyclic ring comprising 1–4 heteroatoms selected from the group consisting of $NR^a$, O, and S;

r, at each occurrence, is selected from 0, 1, 2, 3, and 4;

r', at each occurrence, is selected from 0, 1, 2, 3, and 4;

s, at each occurrence, is selected from 0, 1, and 2; and, s', at each occurrence, is selected from 0, 1, and 2.

3. A compound according to claim 2, wherein:

A is selected from —$CO_2H$, $CH_2CO_2H$, —CONHOH, —$CONHOR^5$, and —$N(OH)COR^5$;

$R^1$ is U—X—Y—Z—$U^a$—$X^a$—$Y^a$—$Z^a$;

Z is selected from a $C_{5-6}$ carbocycle substituted with 0–3 $R^b$ and a 5–6 membered heterocycle comprising carbon atoms and from 1–4 heteroatoms selected from the group consisting of N, O, and S and substituted with 0–3 $R^b$;

$U^a$ is absent or is selected from: O, $NR^a$, C(O), $C(O)NR^a$, and $S(O)_p$;

$X^a$ is absent or selected from $C_{1-6}$ alkylene and $C_{2-6}$ alkenylene;

$Y^a$ is absent or selected from O and $NR^a$;

$Z^a$ is selected from a $C_{5-10}$ carbocycle substituted with 0–3 $R^c$ and a 5–10 membered heterocycle comprising carbon atoms and from 1–4 heteroatoms selected from the group consisting of N, O, and S and substituted with 0–3 $R^c$;

$R^2$ is selected from Q, $C_{1-6}$ alkylene-Q, $C_{2-6}$ alkenylene-Q, $(CRR')_rO(CRR')_r$—Q, $(CRR')_rNR^a(CRR')_r$—Q, and $(CRR')_rC(O)(CRR')_r$—Q;

R, at each occurrence, is independently selected from H, $CH_3$, and $CH_2CH_3$;

R', at each occurrence, is independently selected from H and $CH_3$;

alternatively, $R^1$ and $R^2$ combine to form a $C_{5-6}$ carbocycle substituted with $R^{1'}$ and 0–3 $R^b$ or a 5–6 membered heterocycle comprising carbon atoms and from 1–4 heteroatoms selected from the group consisting of N, O, and S and substituted with $R^{1'}$ and 0–3 $R^b$;

Q is selected from H, a $C_{5-6}$ carbocycle substituted with 0–5 $R^b$ and a 5–6 membered heterocycle comprising carbon atoms and from 1–4 heteroatoms selected from the group consisting of N, O, and S and substituted with 0–5 $R^b$;

$R^{1'}$ is $U^a$—$X^a$—$Y^a$—$Z^a$;

$R^{3a}$ is selected from H, $C_{1-6}$ alkyl, phenyl, and benzyl;

$R^{3c}$ is selected from H, $C_{1-6}$ alkyl, phenyl, and benzyl;

alternatively one of $R^{3a}$ and $R^{3c}$ is independently selected from $(CRR')_rOR^a$, $(CRR')_rNR^aR^{a'}$, $(CRR')_rC(O)R^a$, $(CRR')_rC(O)OR^a$, $(CRR')_rC(O)NR^aR^{a'}$, $(CRR')_rS(O)_pR^a$, and $(CRR')_rS(O)_pNR^aR^{a'}$, provided that in the group $(CRR')_rS(O)_pR^a$, $R^a$ is other than H;

$R^3$ and $R^{3b}$ together with the carbon atoms to which they are attached combine to form a 4–8 membered carbocyclic or heterocyclic ring comprising carbon atoms and 0–2 ring heteroatoms selected from O, N, $NR^a$, and $S(O)_p$ and substituted with 0–2 $R^d$, provided that the cyclic moiety contains other than an N—S, O—S, O—O, or S—S bond;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, —CH(=NOH), —C(=NOH)CH_3, and phenyl;

r, at each occurrence, is selected from 0, 1, 2, and 3; and, r', at each occurrence, is selected from 0, 1, 2, and 3.

4. A compound according to claim 3, wherein:

A is selected from —$CO_2H$, $CH_2CO_2H$, —CONHOH, —$CONHOR^5$, and —$N(OH)COR^5$;

$R^1$ is U—X—Y—Z—$U^a$—$X^a$—$Y^a$—$Z^a$;

Z is selected from phenyl substituted with 0–2 $R^b$ and a 5–6 membered heteroaryl comprising carbon atoms and from 1–4 heteroatoms selected from the group consisting of N, O, and S and substituted with 0–3 $R^b$;

$U^a$ is absent or is O;

$X^a$ is absent or selected from $C_{1-4}$ alkylene and $C_{2-4}$ alkenylene;

$Y^a$ is absent or is O;

$Z^a$ is selected from a $C_{6-10}$ aryl residue substituted with 0–3 $R^c$ and a 5–10 membered heteroaryl comprising carbon atoms and from 1–4 heteroatoms selected from the group consisting of N, O, and S and substituted with 0–3 $R^c$;

$R^2$ is selected from $C_{1-6}$ alkylene, $(CRR')_rOH$, and $(CRR')_rNR^aH$;

$R^{3a}$ is selected from H, $C_{1-6}$ alkyl, phenyl, and benzyl;

$R^{3c}$ is selected from H, $C_{1-6}$ alkyl, phenyl, and benzyl;

$R^3$ and $R^{3b}$ together with the carbon atoms to which they are attached combine to form a 4, 5, 6, 7 or 8 membered carbocyclic or heterocyclic ring comprising carbon atoms and 0–1 ring heteroatoms selected from O, N, $NR^a$, and $S(O)_p$ and substituted with 0–2 $R^d$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, and phenyl;

r, at each occurrence, is selected from 0, 1, and 2; and, r', at each occurrence, is selected from 0, 1, and 2.

5. A compound according to claim 1, wherein the compound is selected from the group:

(1S-cis)-2-[3-amino-3-[4-[2-methyl-4-quinolinyl)methoxy]phenyl]-2-oxo-1-pyrrolidinyl]-N-hydroxycyclohexanecarboxamide;

(1R-trans)-2-[3-amino-3-[4-[(2-methyl-4-quinolinyl)methoxy]phenyl]-2-oxo-1-pyrrolidinyl]-N-hydroxycyclohexanecarboxamide;

(1R-trans)-2-[3-amino-3-[4-[(2-methyl-4-quinolinyl)methoxy]phenyl]-2-oxo-1-pyrrolidinyl]cyclohexanecarboxylic acid;

(1S-cis)-2-[(3S)-3-amino-3-[4-[(2-methyl-4-quinolinyl)methoxy]phenyl]-2-oxo-1-pyrrolidinyl]cyclopentanecarboxylic acid;

(1S-cis)-2-[(3S)-3-amino-3-[4-[(2-methyl-4-quinolinyl)methoxy]phenyl]-2-oxo-1-pyrrolidinyl]-N-hydroxycyclopentanecarboxamide;

(1R-trans)-2-[(3S)-3-amino-3-[4-[(2-methyl-4-quinolinyl)methoxy]phenyl]-2-oxo-1-pyrrolidinyl]-N-hydroxycyclopentanecarboxamide;

(1S-cis)-2-[(3S)-3-amino-3-[4-[(2-methyl-4-quinolinyl)methoxy]phenyl]-2-oxo-1-pyrrolidinyl]-N-hydroxy-4,4-dimethylcyclopentanecarboxamide;

(1S-cis)-1-[(3S)-3-amino-3-[4-[(2-methyl-4-quinolinyl)methoxy]phenyl]-2-oxo-1-pyrrolidinyl]-2,3-dihydro-N-hydroxy-1H-indene-2-carboxamide; and, (3R-trans)-4-[(3S)-3-amino-3-[4-[(2-methyl-4-quinolinyl)methoxy]phenyl]-2-oxo-1-pyrrolidinyl]tetrahydro-N-hydroxy-3-furancarboxamide;

or a pharmaceutically acceptable salt form thereof.

6. A compound selected from the group:

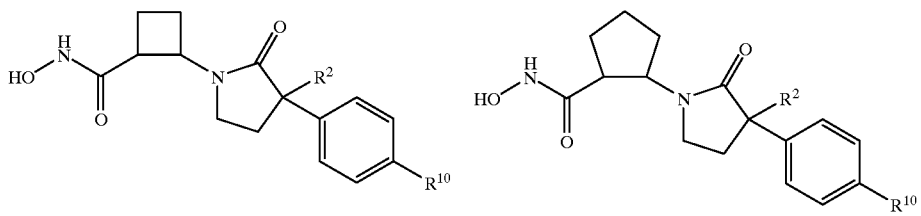

U1 ($R^2$ = Me)
U2 ($R^2$ = $NH_2$)
U3 ($R^2$ = OH)

V1 ($R^2$ = Me)
V2 ($R^2$ = $NH_2$)
V3 ($R^2$ = OH)

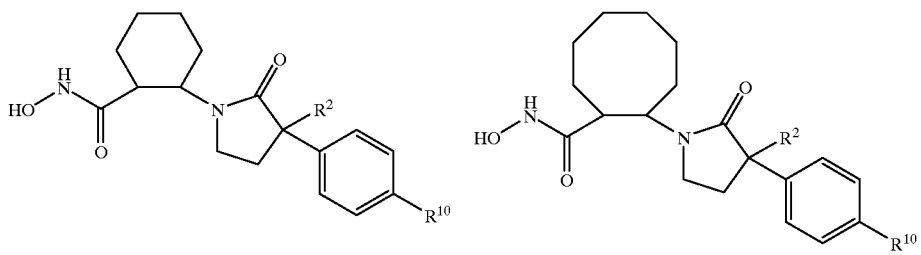

W1 ($R^2$ = Me)S
W2 ($R^2$ = $NH_2$)
W3 ($R^2$ = OH)

X1 ($R^2$ = Me)
X2 ($R^2$ = $NH_2$)
X3 ($R^2$ = OH)

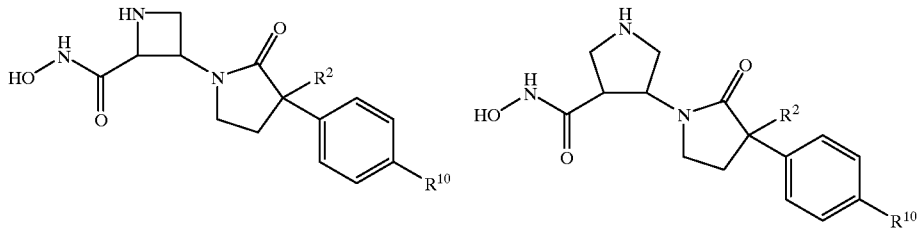

UU1 ($R^2$ = Me)
UU2 ($R^2$ = $NH_2$)
UU3 ($R^2$ = OH)

VV1 ($R^2$ = Me)
VV2 ($R^2$ = $NH_2$)
VV3 ($R^2$ = OH)

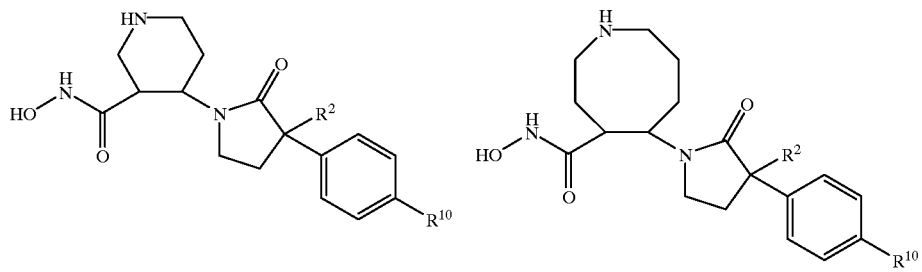
WW1 (R² = Me)
WW2 (R² = NH₂)
WW3 (R² = OH)
XX1 (R² = Me)
XX2 (R² = NH₂)
XX3 (R² = OH)
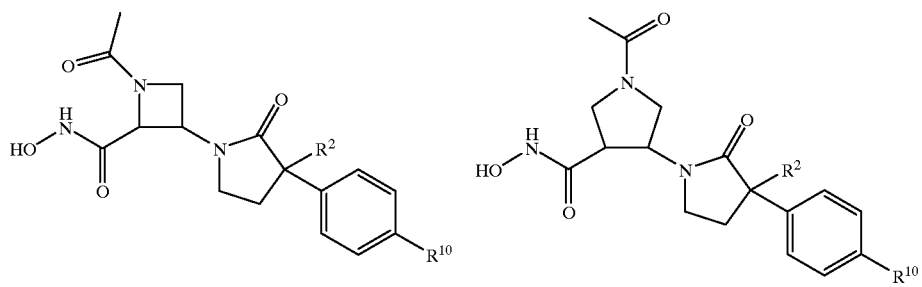
YY1 (R² = Me)
YY2 (R² = NH₂)
YY3 (R² = OH)
ZZ1 (R² = Me)
ZZ2 (R² = NH₂)
ZZ3 (R² = OH)
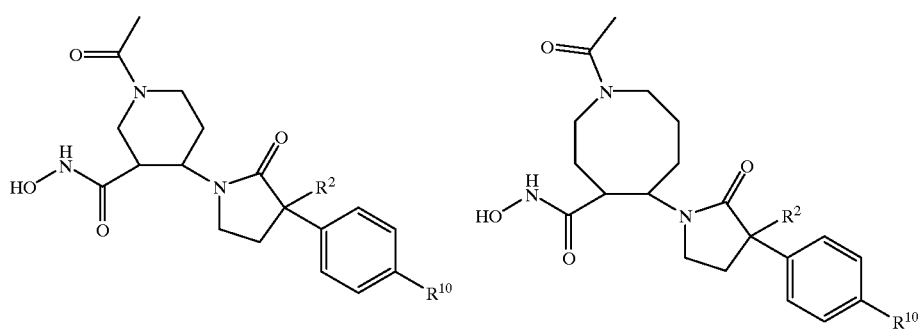
AAA1 (R² = Me)
AAA2 (R² = NH₂)
AAA3 (R² = OH)
BBB1 (R² = Me)
BBB2 (R² = NH₂)
BBB3 (R² = OH)
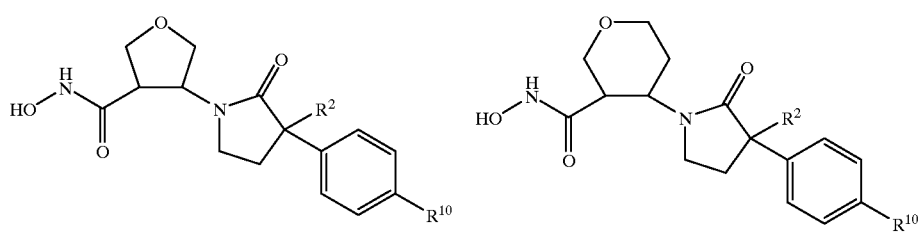
CCC1 (R² = Me)
CCC2 (R² = NH₂)
CCC3 (R² = OH)
DDD1 (R² = Me)
DDD2 (R² = NH₂)
DDD3 (R² = OH)

-continued

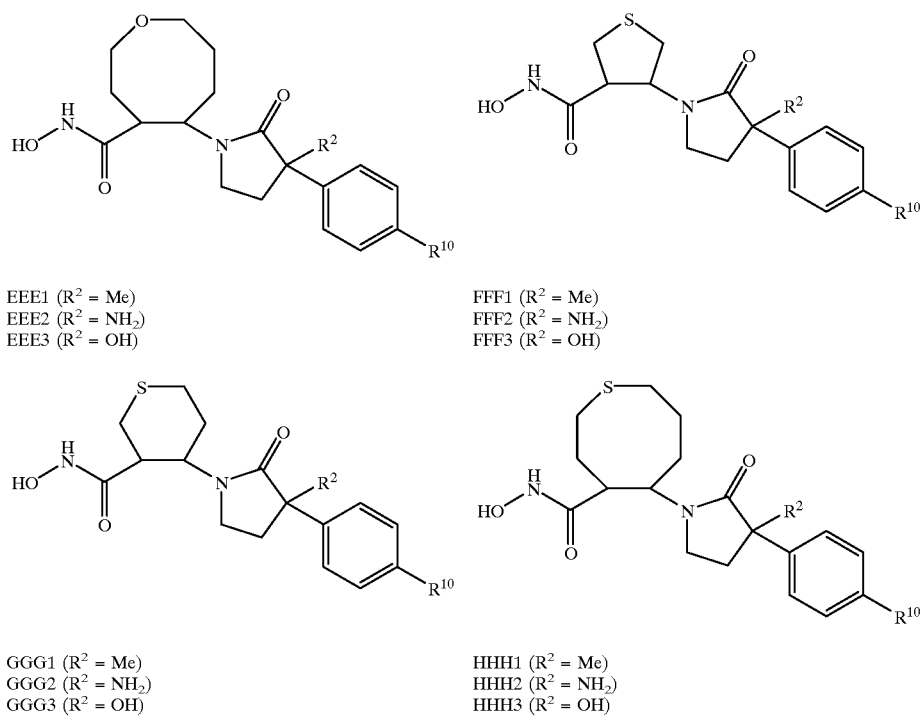

EEE1 (R² = Me)
EEE2 (R² = NH₂)
EEE3 (R² = OH)

FFF1 (R² = Me)
FFF2 (R² = NH₂)
FFF3 (R² = OH)

GGG1 (R² = Me)
GGG2 (R² = NH₂)
GGG3 (R² = OH)

HHH1 (R² = Me)
HHH2 (R² = NH₂)
HHH3 (R² = OH)

| Compound # | R¹⁰ |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)methoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |

-continued

| Compound # | R¹⁰ |
| --- | --- |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |
| 90 | (4,5-dimethyl-2-furanyl)methoxy |
| 91 | (4,5-dimethyl-2-thiazolyl)methoxy |
| 92 | 2-(2-oxazolyl)ethyl | or a pharmaceutically acceptable salt thereof.

7. A pharmaceutical composition, comprising: a pharmaceutically acceptable carrier and a therapeutically effective amount of a compound of claim 1 or a pharmaceutically acceptable salt form thereof.

8. A method of treating, a disease or condition in a mammal, comprising: administering to the mammal in need of such treatment a therapeutically effective amount of a compound of claim 1 or a pharmaceutically acceptable salt form thereof, wherein the disease or condition is selected from acute infection, acute phase response, age related macular degeneration, alcoholism, asthma, Bechet's disease, calcium pyrophosphate dihydrate deposition disease, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, Still's disease, shock, Sjogren's syndrome, skin inflammatory diseases, spondylitis, stroke, systemic lupus erythematosus, ulcerative colitis, uveitis, vasculitis, and Wegener's granulomatosis.

9. A pharmaceutical composition, comprising: a pharmaceutically acceptable carrier and a therapeutically effective amount of a compound of claim 2 or a pharmaceutically acceptable salt form thereof.

10. A pharmaceutical composition, comprising: a pharmaceutically acceptable carrier and a therapeutically effective amount of a compound of claim 3 or a pharmaceutically acceptable salt form thereof.

11. A pharmaceutical composition, comprising: a pharmaceutically acceptable carrier and a therapeutically effective amount of a compound of claim 4 or a pharmaceutically acceptable salt form thereof.

12. A pharmaceutical composition, comprising: a pharmaceutically acceptable carrier and a therapeutically effective amount of a compound of claim 5 or a pharmaceutically acceptable salt form thereof.

13. A pharmaceutical composition, comprising: a pharmaceutically acceptable carrier and a therapeutically effective amount of a compound of claim 6 or a pharmaceutically acceptable salt form thereof.

14. A method of treating, a disease or condition in a mammal. comprising: administering to the mammal in need of such treatment a therapeutically effective amount of a compound of claim 2 or a pharmaceutically acceptable salt form thereof, wherein the disease or condition is selected from acute infection, acute phase response, age related macular degeneration, alcoholism, asthma, Bechet's disease, calcium pyrophosphate dihydrate deposition disease, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, Still's disease, shock, Sjogren's syndrome, skin inflammatory diseases, spondylitis, stroke, systemic lupus erythematosus, ulcerative colitis, uveitis, vasculitis, and Wegener's granulomatosis.

15. A method of treating, a disease or condition in a mammal, comprising: administering to the mammal in need of such treatment a therapeutically effective amount of a compound of claim 3 or a pharmaceutically acceptable salt form thereof, wherein the disease or condition is selected from acute infection, acute phase response, age related macular degeneration, alcoholism, asthma, Bechet's disease, calcium pyrophosphate dihydrate deposition disease, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, Still's disease, shock, Sjogren's syndrome, skin inflammatory diseases, spondylitis, stroke, systemic lupus erythematosus, ulcerative colitis, uveitis, vasculitis, and Wegener's granulomatosis.

16. A method of treating, a disease or condition in a mammal, comprising: administering to the mammal in need of such treatment a therapeutically effective amount of a compound of claim 4 or a pharmaceutically acceptable salt form thereof, wherein the disease or condition is selected from acute infection, acute phase response, age related macular degeneration, alcoholism, asthma, Bechet's disease, calcium pyrophosphate dihydrate deposition disease, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scieroderma, Still's disease, shock, Sjogren's syndrome, skin inflammatory diseases, spondylitis, stroke, systemic lupus erythematosus, ulcerative colitis, uveitis, vasculitis, and Wegener's granulomatosis.

17. A method of treating, a disease or condition in a mammal, comprising: administering to the mammal in need of such treatment a therapeutically effective amount of a compound of claim 5 or a pharmaceutically acceptable salt form thereof, wherein the disease or condition is selected from acute infection, acute phase response, age related macular degeneration, alcoholism, asthma, Bechet's disease, calcium pyrophosphate dihydrate deposition disease, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperflision injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, Still's disease, shock, Sjogren's syndrome, skin inflammatory diseases, spondylitis, stroke, systemic lupus erythematosus, ulcerative colitis, uveitis, vasculitis, and Wegener's granulomatosis.

18. A method of treating, a disease or condition in a mammal, comprising: administering to the mammal in need of such treatment a therapeutically effective amount of a compound of claim 6 or a pharmaceutically acceptable salt form thereof, wherein the disease or condition is selected from acute infection, acute phase response, age related macular degeneration, alcoholism, asthma, Bechet's disease, calcium pyrophosphate dihydrate deposition disease, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperftision injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, Still's disease, shock, Sjogren's syndrome, skin inflammatory diseases, spondylitis, stroke, systemic lupus erythematosus, ulcerative colitis, uveitis, vasculitis, and Wegener's granulomatosis.

* * * * *